(12) United States Patent
Ng et al.

(10) Patent No.: US 11,493,508 B2
(45) Date of Patent: Nov. 8, 2022

(54) COMPOSITIONS AND METHODS FOR THE SIMULTANEOUS GENOMIC, TRANSCRIPTOMIC AND PROTEOMIC ANALYSIS OF SINGLE CELLS

(71) Applicant: IsoPlexis Corporation, Branford, CT (US)

(72) Inventors: Colin Ng, Branford, CT (US); Alaina Kaiser, West Haven, CT (US); Emily Bettini, Waterbury, CT (US); Patrick Paczkowski, East Haven, CT (US); Sean Mackay, New Haven, CT (US); Feimei Liu, Branford, CT (US); Maithreyan Srinivasan, Branford, CT (US)

(73) Assignee: IsoPlexis Corporation, Branford, CT (US)

( * ) Notice: Subject to any disclaimer, the term of this patent is extended or adjusted under 35 U.S.C. 154(b) by 544 days.

(21) Appl. No.: 16/349,183

(22) PCT Filed: Nov. 13, 2017

(86) PCT No.: PCT/US2017/061344
§ 371 (c)(1),
(2) Date: May 10, 2019

(87) PCT Pub. No.: WO2018/089910
PCT Pub. Date: May 17, 2018

(65) Prior Publication Data
US 2019/0285626 A1 Sep. 19, 2019

Related U.S. Application Data

(60) Provisional application No. 62/544,521, filed on Aug. 11, 2017, provisional application No. 62/421,031, filed on Nov. 11, 2016.

(51) Int. Cl.
| | | |
|---|---|---|
| *C12Q 1/00* | (2006.01) | |
| *G01N 33/543* | (2006.01) | |
| *C12Q 1/6813* | (2018.01) | |
| *G01N 33/531* | (2006.01) | |
| *G01N 33/68* | (2006.01) | |
| *C12Q 1/6806* | (2018.01) | |

(52) U.S. Cl.
CPC ..... *G01N 33/54386* (2013.01); *C12Q 1/6806* (2013.01); *C12Q 1/6813* (2013.01); *G01N 33/531* (2013.01); *G01N 33/6842* (2013.01)

(58) Field of Classification Search
CPC .............................................. G01N 33/54386
See application file for complete search history.

(56) References Cited

U.S. PATENT DOCUMENTS

| | | |
|---|---|---|
| 5,858,801 A | 1/1999 | Brizzolara |
| 6,039,897 A | 3/2000 | Lockhead et al. |
| 6,165,739 A | 12/2000 | Clatch |
| 6,377,721 B1 | 4/2002 | Walt et al. |
| 6,429,027 B1 | 8/2002 | Chee et al. |
| 6,524,790 B1 | 2/2003 | Kopf et al. |
| 6,699,665 B1 | 3/2004 | Kim et al. |
| 6,924,153 B1 | 5/2005 | Boehringer |
| 7,312,197 B2 | 12/2007 | Gong |
| 7,381,375 B2 | 6/2008 | Ravkin et al. |
| 7,491,498 B2 | 2/2009 | Lapidus et al. |
| 7,541,444 B2 | 6/2009 | Milton et al. |
| 7,666,593 B2 | 2/2010 | Lapidus |
| 7,785,796 B2 | 8/2010 | Balasubramanian et al. |
| 8,105,845 B2 | 1/2012 | Notcovich |
| 8,236,532 B2 | 8/2012 | Ronaghi et al. |
| 8,394,590 B2 | 3/2013 | Kwong et al. |
| 8,460,878 B2 | 6/2013 | Walt et al. |
| 8,492,165 B2 | 7/2013 | Van Pelt et al. |
| 8,753,816 B2 | 6/2014 | Rigatti et al. |
| 8,802,368 B2 | 8/2014 | Lapidus |
| 8,865,479 B2 | 10/2014 | Love et al. |

(Continued)

FOREIGN PATENT DOCUMENTS

| | | |
|---|---|---|
| CN | 102690786 | 9/2012 |
| DE | 10127221 | 11/2002 |

(Continued)

OTHER PUBLICATIONS

Yamanaka et al. (Integrative Biology 4(10): 1175) (Year: 2012).*
Adams et al. (2008) "Multitarget magnetic activated cell sorter", Proc Natl Acad Sci USA., 105(47):18165-18170.
Adler et al. (2005) "Detection of femtogram amounts of biogenic amines using self-assembled DNA-protein nanostructures," Nature Methods, 2(2):147-149.
Amir et al., (2013) "viSNE enables visualization of high dimensional single-cell data and reveals phenotypic heterogeneity of leukemia", Nat Biotechnol., 31(6):545-52.
Anderson et al. (2002) "The human plasma proteome: history, character, and diagnostic prospects," Mol. Cell. Proteomics, 1 :845-867.

(Continued)

*Primary Examiner* — Albert M Navarro
(74) *Attorney, Agent, or Firm* — Cooley LLP; Ivor R. Elrifi; Andrew Henderson

(57) ABSTRACT

Disclosed are compositions and methods for the multiplexed analysis of one or more intracellular targets of a single cell. Exemplary compositions of the disclosure comprise a surface comprising a plurality of capture agents operatively-linked thereto, wherein each capture agent specifically binds to a distinct intracellular target and wherein the plurality of capture agents form a repeating pattern; a substrate comprising a plurality of chambers, wherein the substrate releasably couples with the surface and wherein each chamber of the plurality of chambers comprises at least one repeat of the repeating pattern of the plurality of capture agents of the surface; a coating composition comprising a cell lysis composition; and a linker composition comprising a functionalization component and an extension component.

15 Claims, 28 Drawing Sheets

(56) References Cited

U.S. PATENT DOCUMENTS

| | | |
|---|---|---|
| 9,005,929 B2 | 4/2015 | Ronaghi et al. |
| 9,051,612 B2 | 6/2015 | Zhao et al. |
| 9,121,060 B2 | 9/2015 | Milton et al. |
| 9,188,586 B2 | 11/2015 | Fan et al. |
| 9,388,464 B2 | 7/2016 | Milton et al. |
| 9,409,987 B2 | 8/2016 | Toporik et al. |
| 9,453,258 B2 | 9/2016 | Kain et al. |
| 9,506,917 B2 | 11/2016 | Fan et al. |
| 9,567,645 B2 | 2/2017 | Fan et al. |
| 9,567,646 B2 | 2/2017 | Fan et al. |
| 9,598,736 B2 | 3/2017 | Fan et al. |
| 9,701,998 B2 | 7/2017 | Hindson et al. |
| 9,727,810 B2 | 8/2017 | Fodor et al. |
| 9,765,391 B2 | 9/2017 | Swerdlow |
| 9,824,870 B1 | 11/2017 | Straume |
| 9,845,502 B2 | 12/2017 | Fodor et al. |
| 9,953,209 B2 | 4/2018 | Adalsteinsson et al. |
| 10,002,316 B2 | 6/2018 | Fodor et al. |
| 10,131,958 B1 | 11/2018 | Fan et al. |
| 10,137,426 B2 | 11/2018 | Love et al. |
| 10,151,003 B2 | 12/2018 | Fan et al. |
| 10,190,965 B2 | 1/2019 | Handique et al. |
| 10,208,356 B1 | 2/2019 | Fan et al. |
| 10,253,375 B1 | 4/2019 | Fan et al. |
| 10,273,541 B2 | 4/2019 | Hindson et al. |
| 10,274,486 B2 | 4/2019 | Fan et al. |
| 10,337,063 B1 | 7/2019 | Brenner et al. |
| 10,378,051 B2 | 8/2019 | Meuleman et al. |
| 10,391,492 B2 | 8/2019 | Handique et al. |
| 10,391,493 B2 | 8/2019 | Handique et al. |
| 10,400,280 B2 | 9/2019 | Hindson et al. |
| 10,436,700 B1 | 10/2019 | Handique et al. |
| 10,513,731 B2 | 12/2019 | Milton et al. |
| 10,619,196 B1 | 4/2020 | Chee |
| 10,633,702 B2 | 4/2020 | Brenner et al. |
| 10,641,700 B2 | 5/2020 | Handique |
| 10,676,789 B2 | 6/2020 | Hindson et al. |
| 10,718,007 B2 | 7/2020 | Handique et al. |
| 10,746,648 B2 | 8/2020 | Handique |
| 10,752,950 B2 | 8/2020 | Hindson et al. |
| 10,774,374 B2 | 9/2020 | Frisen et al. |
| 10,793,904 B2 | 10/2020 | Swerdlow |
| 10,821,440 B2 | 11/2020 | Handique et al. |
| 10,921,237 B2 | 2/2021 | Handique |
| 10,927,419 B2 | 2/2021 | Fan et al. |
| 10,928,389 B2 | 2/2021 | Fan et al. |
| 10,941,396 B2 | 3/2021 | Fu et al. |
| 10,954,570 B2 | 3/2021 | Fan et al. |
| 11,021,749 B2 | 6/2021 | Hindson et al. |
| 11,066,689 B2 | 7/2021 | Paczkowski et al. |
| 2001/0016320 A1 | 8/2001 | He |
| 2002/0090649 A1 | 7/2002 | Chan |
| 2002/0100714 A1 | 8/2002 | Staats |
| 2002/0131974 A1 | 9/2002 | Segal |
| 2002/0146745 A1 | 10/2002 | Natan et al. |
| 2003/0013091 A1 | 1/2003 | Dmitrov |
| 2003/0082601 A1 | 5/2003 | Dill |
| 2003/0096232 A1 | 5/2003 | Kris et al. |
| 2003/0104486 A1 | 6/2003 | Selvan |
| 2003/0127610 A1 | 7/2003 | Gallagher |
| 2003/0190608 A1 | 10/2003 | Blackbum |
| 2003/0190689 A1 | 10/2003 | Crosby |
| 2004/0092032 A1 | 5/2004 | Winkler |
| 2004/0191124 A1 | 9/2004 | Noetzel |
| 2004/0224321 A1 | 11/2004 | Nicolau |
| 2004/0265889 A1 | 12/2004 | Durham |
| 2005/0032144 A1 | 2/2005 | Lombardi |
| 2005/0142033 A1 | 6/2005 | Glezer |
| 2005/0197311 A1 | 9/2005 | Cooper |
| 2005/0226779 A1 | 10/2005 | Oldham et al. |
| 2006/0246475 A1 | 11/2006 | Peterson et al. |
| 2006/0263818 A1 | 11/2006 | Scherer |
| 2006/0286549 A1 | 12/2006 | Sohn |
| 2007/0074972 A1 | 4/2007 | Nassef |
| 2007/0122819 A1 | 5/2007 | Wu |
| 2007/0202538 A1 | 8/2007 | Glezer et al. |
| 2007/0243535 A1 | 10/2007 | Harris |
| 2008/0200343 A1 | 8/2008 | Clemens |
| 2008/0207461 A1 | 8/2008 | Ermantraut et al. |
| 2008/0317627 A1 | 12/2008 | Shirai et al. |
| 2009/0017455 A1 | 1/2009 | Kwong |
| 2009/0036324 A1 | 2/2009 | Fan et al. |
| 2009/0053732 A1 | 2/2009 | Vermesh et al. |
| 2009/0137413 A1 | 5/2009 | Mehta et al. |
| 2009/0227043 A1 | 9/2009 | Huang |
| 2010/0009335 A1 | 1/2010 | Joseph |
| 2010/0152054 A1 | 6/2010 | Love et al. |
| 2010/0213063 A1 | 8/2010 | Zenhausen et al. |
| 2010/0279882 A1 | 11/2010 | Ronaghi et al. |
| 2010/0297145 A1 | 11/2010 | Tsujikawa et al. |
| 2011/0034908 A1 | 2/2011 | Hyde et al. |
| 2011/0048952 A1 | 3/2011 | Van Pelt et al. |
| 2011/0177537 A1 | 7/2011 | Nissum et al. |
| 2011/0224913 A1 | 9/2011 | Cui et al. |
| 2012/0015824 A1 | 1/2012 | Love et al. |
| 2012/0156675 A1 | 6/2012 | Luerssen et al. |
| 2012/0316074 A1 | 12/2012 | Saxonov |
| 2013/0274117 A1 | 10/2013 | Church et al. |
| 2013/0338047 A1 | 12/2013 | Love et al. |
| 2014/0128281 A1 | 5/2014 | Zhang et al. |
| 2014/0170642 A1 | 6/2014 | Huang et al. |
| 2014/0307931 A1 | 10/2014 | Gierahn et al. |
| 2015/0078999 A1 | 3/2015 | Heath et al. |
| 2015/0086424 A1 | 3/2015 | Putnam et al. |
| 2015/0204862 A1 | 7/2015 | Fan et al. |
| 2015/0204864 A1 | 7/2015 | Fan et al. |
| 2016/0129445 A1 | 5/2016 | Corey et al. |
| 2016/0160169 A1 | 6/2016 | Paczkowski et al. |
| 2016/0167049 A1 | 6/2016 | Narahara et al. |
| 2016/0238594 A1 | 8/2016 | Xue et al. |
| 2017/0067887 A1 | 3/2017 | Fan et al. |
| 2017/0138942 A1 | 5/2017 | Fan et al. |
| 2018/0105855 A1 | 4/2018 | Paczkowski et al. |
| 2018/0335419 A1 | 11/2018 | Love et al. |
| 2019/0024153 A1 | 1/2019 | Frisen et al. |
| 2019/0144936 A1 | 5/2019 | Gierahn et al. |
| 2019/0195869 A1 | 6/2019 | Fan et al. |
| 2019/0285626 A1 | 9/2019 | Ng et al. |
| 2019/0324028 A1 | 10/2019 | Fan et al. |
| 2019/0376898 A1 | 12/2019 | Tsiomplikas et al. |
| 2020/0166518 A1 | 5/2020 | Mackay et al. |
| 2020/0239926 A1 | 7/2020 | Paczkowski et al. |
| 2021/0388446 A1 | 12/2021 | Abate et al. |
| 2022/0017858 A1 | 1/2022 | Zheng et al. |

FOREIGN PATENT DOCUMENTS

| | | |
|---|---|---|
| EP | 1816476 A1 | 8/2007 |
| EP | 2336348 A1 | 6/2011 |
| EP | 3241913 A1 | 11/2017 |
| EP | 3480321 B1 | 5/2019 |
| JP | 2010-066146 | 3/2010 |
| WO | WO 96/28538 A1 | 9/1996 |
| WO | WO 02/077259 A2 | 10/2002 |
| WO | WO 2003/048736 A2 | 6/2003 |
| WO | WO 2005/007892 A1 | 1/2005 |
| WO | WO 2005/081867 A2 | 9/2005 |
| WO | WO 2005/090972 | 9/2005 |
| WO | WO 2006/117541 A1 | 11/2006 |
| WO | WO 2007/014267 A2 | 2/2007 |
| WO | WO 2007/035633 A2 | 3/2007 |
| WO | WO 2008/016680 A1 | 2/2008 |
| WO | WO 2009/012340 A2 | 1/2009 |
| WO | WO 2009/012343 A2 | 1/2009 |
| WO | WO 2010/065929 A2 | 6/2010 |
| WO | WO 2010/117620 A2 | 10/2010 |
| WO | WO 2012/083225 A2 | 6/2012 |
| WO | WO 2013/090404 A2 | 6/2013 |
| WO | WO 2013/130674 A1 | 9/2013 |
| WO | WO 2013/148448 A1 | 10/2013 |
| WO | WO 2014/031997 A1 | 2/2014 |
| WO | WO 2014/052989 A2 | 4/2014 |
| WO | WO 2015/031691 A1 | 3/2015 |
| WO | WO 2016/009446 A2 | 1/2016 |

(56) References Cited

FOREIGN PATENT DOCUMENTS

| WO | WO 2016/057552 A1 | 4/2016 |
|---|---|---|
| WO | WO 2016/057705 A1 | 4/2016 |
| WO | WO 2016/090148 A1 | 6/2016 |
| WO | WO 2016/090320 A1 | 6/2016 |
| WO | WO 2016/118915 A1 | 7/2016 |
| WO | WO 2016/130704 A2 | 8/2016 |
| WO | WO 2016/138496 A1 | 9/2016 |

OTHER PUBLICATIONS

Arenkov et al. (2000) "Protein microchips: use for immunoassays and enzymatic reactions," Anal. Biochem., 278:123-131.
Armstrong et al. (2000) "Suspension arrays for high throughput, multiplexed single nucleotide polymorphism genotyping," 40(2):102-108.
Ashton et al. (1973) "Smoking and carboxhemoglobin," Lancet. 2:857-858.
Balaban et al., (2004) "Bacterial persistence as a phenotypic switch", Science, 305(5690): 1622-5.
BD Biosciences (2007) "Purified Mouse Anti-Human IL-2," Accessible on the Internet at URL: http://www.bdbiosciences.com/ptProduct.jsp?prodid=6725.
BD Pharmingen (2003) "Technical data sheet: Purified mouse anti-human IL-2 monoclonal antibody (ELISA capture)," BD Biosciences. Accessible on the Internet at URL: http://www.bdbiosciences.com/ds/pm/tds/555051.pdf.
Becker et al. (2005) "Direct readout of protein-protein interactions by mass spectrometry from protein-DNA microarrays," Angew. Chemie. Int. Ed. 44:7635-7639.
Bend All et al., (2012) "From single cells to deep phenotypes in cancer", Nat Biotechnol., 30(7):639-47.
Bendall et al., (2011) "Single-cell mass cytometry of differential immune and drug responses across a human hematopoietic continuum", Science, 332(6030):687-96.
Bernard et al. (2001) "Micromosaic immunoassays," Analytical Chemistry. 73:8-12.
Betensky et al. (2002) "Influence of unrecognized molecular heterogeneity on randomized clinical trials," J. Clin. Oncol. 20:2495-2499.
Boozer et al. (2004) "DNA directed protein immobilization on mixed ssDNA/oligo(ethylene glycol) self-assembled monolayers for sensitive biosensors," Anal. Chem. 76:6967-6972.
Boozer et al. (2006) "DNA-Directed Protein Immobilization for Simultaneous Detection of Multiple Analytes by Surface Plasmon Resonance Biosensor," Analytical Chemistry. 78:1515-1519.
Breslauer et al. (2006) "Microfluidic-based systems biology," Mol. Biosyst. 2:97-112.
Bunimovich et al. (2006) "Quantitative Real-Time Measurements of DNA Hybridization with Alkylated Nonoxidized Silicon Nanowires in Electrolyte Solution," J. Am. Chem. Soc. 128:16323-16331.
Chattopadhyay, P. et al. (2014) "Single-cell technologies for monitoring immune systems," Nature Immunology, 15(2):128-135.
Chen et al. (2002) "Discordant protein and mRNA expression in lung adenocarcinomas," Mol. Cell. Proteomics. 1:304-313.
Chen et al. (2004) "Plasma proteome of severe acute respiratory syndrome analyzed by two-dimensional gel electrophoresis and mass spectrometry," Proc. Natl. Acad. Sci. USA. 101:17039-17044.
Chen et al. (2005) "Marked Differences in Human Melanoma Antigen-Specific T Cell Responsiveness after Vaccination Using a Functional Microarray," PLoS Medicine, 2(10):1018-1030.
Chen et al., (2007) "Multiplexed analysis of glycan variation on native proteins captured by antibody microarrays", Nat Methods, 4(5):437-44.
Chen X. et al. (2012) "Microfluidic Devices Targeting Blood Cell Lysis", On-Chip Pretreatment of Whole Blood by Using MEMS Technology, p. 64-83.
Cheong et al. (2009) "Using a microfluidic device for high-content analysis of cell signaling", Sci Signal, 2(75), p. 12.
Choi et al., (2011) "Immuno-hybridization chain reaction for enhancing detection of individual cytokinesecreting human peripheral mononuclear cells", Anal Chem, 83(17):6890-5.
Chou et al. (2000) "Sorting biomolecules with microdevices," Electrophoresis. 21:81-90.
Coussens et al. (2002) "Inflammation and cancer," Nature. 420:860-867.
Crowley et al. (2005) "Isolation of plasma from whole blood using planar microfilters for lab-on-a-chip applications," Lab on a Chip. 5:922-929.
Dandy et al. (2007) "Array feature size influences nucleic acid surface capture in DNA microarrays," Proc Natl. Acad. Sci. USA, 104:8223-8228.
Das S. et al., (2015) "A General Synthetic Approach for Designing Epitope Targeted Macrocyclic Peptide Ligands", Angewandte Chemie, 54:13219-13224.
De Marzo et al. (2007) "Inflammation in prostate carcinogenesis," Nature Reviews Cancer. 7:256-269.
Degenaar et al. (2001) "A method for micrometer resolution patterning of primary culture neurons for SPM analysis,"!. Biochem, 130:367-376.
Dehqanzada et al. (2005) "Assessing serum cytokine profiles in breast cancer patients receiving a HER2/neu vaccine using Luminex technology," Annals of Surgical Oncology, 12:S47-S48.
Delamarche et al. (1997) "Patterned delivery of immunoglobulins to surfaces using microfluidic networks," Science, 76:779-781.
Deyle, Kaycie M. et al. (2015) "Protein-targeting strategy used to develop a selective inhibitor of the E17K point mutation in the PH domain of Akt1"; Nat. Chem., 7(5), p. 455-462.
Dirks et al. (2004) "Paradigms for computational nucleic acid design," Nucleic Acids Research. 32(4): 1392-1403.
Downward, J., (2003) "Targeting RAS Signalling Pathways in Cancer Therapy", Nature Reviews, vol. 3, 22 pages.
Elitas, Meltem et al. (2014) "A microchip platform for interrogating the single-cell level", Lab on a Chip, vol. 14, No. 18, p. 3582.
Engvall et al. (1972) "Enzyme-linked immunosorbent assay, Elisa. 3. Quantitation of specific antibodies by enzymeabeled anti-immunoglobulin in antigen-coated tubes," J. Immunol. 109:129-135.
Erickson et al. (2003) "Modeling of DNA hybridization kinetics for spatially resolved biochips," Anal. Biochem. 317:186-200.
Eyer K. et al. (2013) "Implementing Enzyme-Linked Immunosorbent Assays on a Microfluidic Chip To Quantify Intracellular Molecules in Single Cells", Analytical Chemistry, vol. 85, No. 6, pp. 3280-3287.
Fainerman et al. (1998) "Adsorption of surfactants and proteins at fluid interfaces," Colloids and Surfaces, 143:141-165.
Fan et al., (2008) "Integrated barcode chips for rapid, multiplexed analysis of proteins in microliter quantities of blood", Nature Biotechnology, vol. 26, p. 1373-1378.
Fan et al., (2008) "Integrated blood barcode chips", Nature Biotechnology, vol. 26, No. 12, p. 1373-1378.
Fuji et al. (2005) "Clinical-scale high-throughput human plasma proteome analysis: lung adenocarcinoma," Droteomics. 5:1150-1159.
Fung (1973) "Stochastic flow in capillary blood vessels," Microvasc. Res. 5:34-38.
Galbraith, W. et al. (1993) "Remapping disparate images for conincidence", Journal of Microscopy, vol. 172, No. 2, pp. 163-176.
Gorelik et al. (2005) "Multiplexed immunobead-based cytokine profiling for early detection of ovarian cancer," Cancer Epidemiol, Biomarkers Prev. 14:981-987.
Green et al. (2006) "Capturing the uncultivated majority", Current Opinion in Biotechnology, 17(3), p. 250-255.
Groves et al. (1995) "In vitro maturation of clonal CD4+CD8+ cell lines in response to TCR engagement," J. Immunol, 154:5011-5022.
Guan et al. (2004) "Recombinant protein-based enzyme-linked immunosorbent assay and immunochromatographic tests for detection of immunoglobulin G antibodies to severe acute respiratory syndrome (SARS) coronavirus in SARS patients," Clinical and Diagnostics Laboratory Immunology, 11(2):287-291.

(56) References Cited

OTHER PUBLICATIONS

Hainfeld et al. (2002) "Silver and Gold-Based Autometallography of Nanogold," Ch. 3, Gold and Silver Staining, CRC Press. Washington, DC. pp. 29-46.
Han et al., (2010) "Multidimensional analysis of the frequencies and rates of cytokine secretion from single cells by quantitative microengraving", Lab Chip, 10(11):1391-400.
Han et al., (2012) "Polyfunctional responses by human T cells result from sequential release of cytokines", Proc Natl Acad Sci USA, 109(5):1607-12.
Heath et al. (2007) "Nanotechnology and cancer," Annual Review of Medicine. 59:251-265.
Henshall et al. (2007) "Assay: Validating biomarkers with VeraCode", Genet Eng Biotechnol News, 27(17): 1-3.
Holland et al. (1991) "Detection of specific polymerase chain reaction product by utilizing the 5'—3' exonuclease activity of Thermus aquaticus DNA polymerase" Proc. Natl. Acad. Sci. USA. 88:7276-7280.
Hong et al. (2003) "Integrated nanoliter systems," Nature Biotechnology, 21 :1179-1183.
Hong et al. (2004) "A nanoliter-scale nucleic acid processor with parallel architecture," Nature Biotechnology, 22 (4): 435-439.
Hsieh et al. (2006) "Systematical evaluation of the effects of sample collection procedures on low-molecular-weight serum/plasma proteome profiling," Proteomics. 6:3189-3198.
Huang et al. (2001) "Detection of multiple proteins in an antibody-based protein microarray system," Journal of Immunological Methods. 255:1-13.
Huang et al. (2004) "Continuous particle separation through deterministic lateral displacement," Science, 304:987-990.
Huang et al. (2007) "Counting low-copy number proteins in a single cell," Science. 315:81-84.
Huber et al. (2004) "Comparison of proteomic and genomic analyses of the human breast cancer cell line T47D and the antiestrogen-resistant derivative T47D-r," Molec. Cell. Proteomics. 3:43-55.
Hughes et al. (2003) "Molecular Monitoring of Chronic Myeloid Leukemia," Seminars in Hematology, 40(2):62-68.
Hughes, A. et al. (2014) "Single-cell western blotting", Nat Methods, 1 (7):749-55.
Iannone et al. (1999) "Multiplexed single nucleotide polymorphism genotyping by oligonucleotide ligation and flow cytometry," Cytometry, 39(2):131-140.
Inerowicz et al. (2002) "Multiprotein immunoassay arrays fabricated by microcontact printing," Langmuir, 18:5263-5268.
Ivanova et al. (2002) "Polymer Microstructures Fabricated via Laser Ablaton Used for Multianalyte Protein Microassay", Langmuir, vol. 18, p. 9539-9546.
Jeon et al. (1991) "Protein-surface interactions in the presence of polyethylene oxide: II. Effect of protein size," Journal of Colloid and Interface Science. 142(1): 159-166.
Kim et al. (1979) "Establishment and characterization of BALB/c lymphoma lines with B cell properties," J. Immunol, 122:549-554.
Kiyonaka et al. (2004) "Semi-wet peptide/protein array using supramolecular hygrogel," Nature Materials. 3:58-64.
Kochenderfer et al. (2012) B-cell depletion and remissions of malignancy along with cytokine-associated toxicity in a clinical trial of anti-CD19 chimeric-antigen-receptor-transduced T-cells Blood, vol. 119, No. 12, p. 2709-2720.
Kozlov et al. (2004) "Efficient strategies for the conjugation of oligonucleotides to antibodies enabling highly sensitive protein detection," Biopolymers. 73:621-630.
Krzywinski M. et al. (2009) "Circos: An information aesthetic for comparative genomics"; Genome Res., 19, p. 1639-1645.
Kwak, M. et al. (2013) "Single-cell protein secretomic signatures as potential correlates to tumor cell lineage evolution and cell-cell interaction", Frontiers in Oncology, 3, Art. 10, p. 1-8.
Kwon et al. (2004) "Antibody arrays prepared by cutinase-mediated immobilization on self-assembled monolayers,"Anal Chem, 76:5713-5720.

Kwong et al. (2005) "Synchronous global assessment of gene and protein expression in colorectal cancer progression," Genomics. 86:142-158.
Lamb et al. (2006) "The Connectivity Map: using gene-expression signatures to connect small molecules, genes, and disease," Science. 313(5795): 1929-1935.
Lambeck et al. (2007) "Serum cytokine profiling as a diagnostic and prognostic tool in ovarian cancer: a potential role or interleukin 7," Clinical Cancer Research, 13:2385-2391.
Lange et al. (2004) "Microcontact printing of DNA molecules," Analytical Chemistry. 76:1641-1647.
Lathrop (2003) "Therapeutic potential of the plasma proteome," Current Opinion in Molecular Therapeutics, 5:250-257.
Lecault et al., (2011) "High-throughput analysis of single hematopoietic stem cell proliferation in microfluidic cell culture arrays", Nat Methods, 8(7):581-586.
Lee et al. (2001) "SPR Imaging Measurements of 1-D and 2-D Dna Microarrays Created from Microfluidic Channels on Gold Thin Films," Analytical Chemistry, 73(22):5525-5531.
Lee et al., (2012) "Quantitative and dynamic assay of single cell chemotaxis", Integr Biol (Camb). 4(4):381-390.
Lin et al. (2005) "Evidence for the Presence of Disease-Perturbed Networks in Prostate Cancer Cells by Genomic and Droteomic Analyses: A Systems Approach to Disease," Cancer Res. 65:3081-3091.
Lin et al. (2007) "A cytokine-mediated link between innate immunity, inflammation, and cancer," Journal of Clinical Investigation, 117:1175-1183.
Liotta et al. (2003) "Protein microarrays: meeting analytical challenges for clinical applications", Cancer Cell, 3(4):317-325.
Liu et al. (2000) "Photopatterning of antibodies on biosensors," Bioconjugate Chem. 11 :755-761.
Love et al. (2006) "A microengraving method for rapid selection of single cells producing antigenspecific antibodies", Nat Biotechnol, 24(6):703-707.
Lu, Yao et al. (2013) "High-Throughout Secretomic Analysis of Single Cells to Assess Functional Cellular Heterogeneity", vol. 85, No. 4, pp. 2548-2556.
Ma, Chao et al. (2011) "A clinical microchip for evaluation of single immune cells reveals phenotypically similar T cells", Nature Medicine, vol. 17, No. 6, pp. 738-743.
MacBeath et al. (2000) "Printing proteins as microarrays for high-throughput function determination," Science, 289:1760-1763.
Madoz-Gurpide et al. (2001) "Protein based microarrays: A tool for probing the proteome of cancer cells and issues," Proteomics, 1(10):1279-1287.
Martin et al. (2006) "Molecular biology of breast cancer," Clin. Trans. Oneel. 8(1):7-14.
Mellinghoff et al. (2006) "Molecular determinants of the response of glioblastomas to EGFR kinase inhibitors," N. Engl. J, Med. 353:2012-2024.
Michel et al. (2002) "Printing meets lithography: Soft approaches to high-resolution patterning," Chimia. 56:527-542.
Michor et al. (2010) "The origins and implications of intratumor heterogeneity", Cancer Prev Res (Phila), 3(11):1361-1364.
Mischel et al. (2004) "DNA-microarray analysis of brain cancer: molecular classification for therapy," Nature Rev. Neurosci. 5:782-794.
Nagrath et al. (2007) "Isolation of rare circulating tumour cells in cancer patients by microchip technology," Nature, 450:1235-1239.
Nam et al. (2003) "Nanoparticle-based bio-bar codes for the ultrasensitive detection of proteins," Science, 301 :1884-1886.
Nam et al. (2003) "Nanoparticle-based bio-bar codes for the ultrasensitive detection of proteins," Science, 301:1884-1886,—Supporting Material pp. 1 to 12.
Nathanson et al. (2014) "Co-targeting of convergent nucleotide biosynthetic pathways for leukemia eradication", J. Exp. Med., vol. 211(3), p. 473-486.
Niemeyer (2007) "Functional devices from DNA and proteins," Nano Today, 2:42-52.
Niemeyer et al. (2005) "Immuno-PCR: high sensitivity detection of proteins by nucleic acid amplification," Trends in Biotechnology, 23:208-216.

(56) References Cited

OTHER PUBLICATIONS

Ostrem, J.M. et al. (2013) "K-Ras(G12C) inhibitors allosterically control GTP affinity and effector interactions", Nature, vol. 503, 14 pages.

Ottesen et al. (2006) "Microfluidic digital PCR enables multigene analysis of individual environmental bacteria," Science, 314:1464-1467.

Pal et al. (2006) "Differential Phosphoprotein Mapping in Cancer Cells Using Protein Microarrays Produced from 2-D Liquid Fractionation," Anal. Chem. 78:702-710.

Park et al. (2002) "Array-Based Electrical Detection of DNA with Nanoparticle Probes," Science. 295:1503-1506.

Peluso et al. (2003) "Optimizing antibody immobilization strategies for the construction of protein arrays," Anal. Biochem, 312:113-124.

Phillips (2004) "Rapid analysis of inflammatory cytokines in cerebrospinal fluid using chip-based immunoaffinity electrophoresis," Electrophoresis. 25:1652-1659.

Pirrung (2002) "How to make a DNA chip," Angew. Chem. Int. Ed. 41:1276-1289.

Prados et al. (2003) "Temozolomide + OS1-774," Proc. Am. Soc. Clin. Oncology, 22:99.

Prime et al. (1991) "Self-assembled organic monolayers: model systems for studying adsorption of proteins at Urfaces," Science, 252:1164-1167.

Prime et al. (1993) "Adsorption of proteins onto surfaces containing end-attached oligo(ethylene oxide): a model system using self-assembled monolayers," J. Am. Chem. Soc.115(23):10714-10721.

Quake et al. (2000) "From Micro—to Nanofabrication with Soft Materials," Science, 290:1536-1540.

Radich et al. (2006) "Gene expression changes associated with progression and response in chronic myeloid leukemia," Proc. Natl. Acad. Sci. USA, 103(8):2794-2799.

Ramsden (1995) "Puzzles and Paradox in Protein Adsorption," J. Chem. Soc. Rev. 24:73-78.

Rich et al. (2004) "Phase II trial of gefitinib in recurrent glioblastoma," J. Clin.Oncology 22:133-142.

Rowat et al., (2009) "Tracking lineages of single cells in lines using a microfluidic device", Proc Natl Acad Sci USA, 106(43): 18149-54.

Sachdeva et al., (2007) "Cytokine quantitation: technologies and applications", Front Biosci. M12:4682-95, Review.

Sano et al. (1992) "Immuno-PCR: very sensitive antigen detection by means of specific antibody-DNA conjugates," Science, 258:120-122.

Sarkar A. et al. (2014) "Microfluidic probe for single-cell analysis in adherent tissue culture", Nature Communications, vol. 5, 8 pages.

Schena et al. (1995) "Quantitative monitoring of gene expression patterns with a complementary DNA microarray," Science, 270:467-470.

Schubert, S. et al. (2007) Hyperactive Ras in developmental disorders and cancer, Nature Reviews, vol. 7, 14 pages.

Schweitzer et al. (2002) "Multiplexed protein profiling on microarrays by rolling-circle amplification," Nature Biotechnology, 20:359-365.

Sedgwick H. et al. (2008) "Lab-on-a-chip technologies for proteomic analysis from isolated cells", A Journal of the Royal Society, vol. 5, No. 2, pp. S123-S130.

Shi Q. et al. (2011) "Single-cell proteomic chip for profiling intracellular signaling pathways in single tumor cells", Proceedings National Academy of Sciences PNAS, vol. 109, No. 2, pp. 419-424.

Shin Y. et al. (2010) "Chemistries for Patterning Robust DNA MicroBarcodes Enable Multiplex Assays of Cytoplasm Proteins from Single Cancer Cells", ChemPhysChem, vol. 11, No. 14, pp. 3063-3069.

Shin et al., (2011) "Protein signaling networks from single cell fluctuations and information theory profiling", Biophys J., 100(10):2378-86.

Sia et al. (2003) "Microfluidic devices fabricated in poly(dimethylsiloxane) for biological studies," Electrophoresis, 24:3563-3576.

Soen et al. (2003) "Detection and characterization of cellular immune responses using peptide-MHC microarrays," PLoS Biology, 1 (3):429-438.

Sorger, P. (2008) "Microfluidics closes in on point-of-care assays", Nature Biotechnology, vol. 26, p. 1345-1346.

Spiro et al. (2000) "A bead-based method for multiplexed identification and quantitation of DNA sequences using flow cytometry," 66(10):425 8-4265.

Svanes et al. (1968) "Variations in small blood vessel hematocrits produced in hypthermic rats by micro-occlusion," Microvascular Research, 1:210-220.

Taton et al. (2000) "Scanometric DNA array detection with nanoparticle probes," Science, 289:1757-1760.

Thirumalapura et al. (2005) "Lipopolysaccharide microarrays for the detection of antibodies," Journal of Immunological Methods. 298:73-81.

Thorsen et al. (2002) "Microfluidic large-scale integration," Science. 298:580-584.

Thuillier et al. (2005) "Development of a low-cost hybrid Si/PDMS multi-layered pneumatic microvalve," Microsystem Technologies. 12(1): 180-185.

Tian et al. (2004) "Integrated genomic and proteomic analyses of gene expression in mammalian cells," Mol. Cell. Proteomics. 3:960-969.

Toner et al. (2005) "Blood-on-a-chip," Annual Review of Biomedical Engineering. 7:77-103.

Toure, M. et al., (2016) "Small-Molecule PROTACS: New Approaches to Protein Degradation", Angew. Chem, Int. Ed., vol. 55, 9 pages.

Unger et al., (2000) "Monolithic microfabricated valves and pumps by multilayer soft lithography", Science, 288(5463): 113-6.

Van Duijn et al. (2002) "Detection of genetically modified organisms in foods by protein-and DNA-based techniques: bridging the methods," JAOAC Int. 85(3):787-791.

Wacker (2004) "DD1-microFIA-A readily configurable microarray-fluorescence immunoassay based on DNA-direcled immobilization of proteins," Chembiochem, 5:453-459.

Wang et al., (2010) "Single cell analysis: the new frontier in 'omics'", Trends Biotechnol., 28(6):281-90.

Wei et al., (2013) "Microchip platforms for multiplex single-cell functional proteomics with applications to immunology and cancer research", Genome Med., 5(8):75.

Wegner et al. (2003) "Fabrication of Histidine-Tagged Fusion Protein Arrays for Surface Plasmon Resonance maging Studies of Protein-Protein and Protein-DNA Interactions," Analytical Chemistry, 75:4740-4746.

Whitesides et al. (2001) "Soil lithography in biology and biochemistry," Annual Review of Biomedical Engineering, 3:335-373.

Wysocki et al. (1978) "Panning for lymphocytes: a method for cell selection," Proc. Nall. Acad. Sci. USA. 75(6):2844-2848.

Yamanaka Y. J. et al. (2012) "Single-cell analysis of the dynamics and functional outcomes of interactions between human natural killer cells and target cells" Integrative Biology, vol. 4, No. 10, p. 1175-1184.

Yang et al. (2006) "A microfluidic device for continuous, real lime blood plasma separation," Lab on a Chip, 5:871-880.

Yang et al., (2007) "Using a cross-flow microfluidic chip and external crosslinking reaction for monodisperse TPP-chitosan microparticles", Sensors and Acuators, 124:510-516.

Yu et al. (2005) "Contextual interactions determine whether the Drosophila homeodomain protein, Vnd, acts as a repressor or activator," Nucleic Acids Research, 33(8): 1-11.

Yu Y. et al. (2015) "Analysis of the surface, secreted, and intracellular proteome of Propionibacterium acnes", EUPA Open Proteonomics, vol. 9, pp. 1-7.

Yu J. et al. (2014) "Microfluidics-Based Single-Cell Functional Proteomics for Fundamental and Applied Biomedical Applications," Annual Review of Analytical Chemistry, vol. 7, p. 275-295.

Zhang, K. et al. (2006) "Sequencing genomes from single cells by polymerase cloning", Nature Biotechnology 24(6):680-686.

(56) References Cited

OTHER PUBLICATIONS

Zhao et al. (2007) "High-Affinity TCRs Generated by Phage Display Provide $CD4^+T$ Cells with the Ability to Recognize and Kill Tumor Cell Lines", The Journal of Immunology, vol. 179, No. 9, p. 5845-5854.

Zimmermann et al. (2005) "Modeling and optimization of high-sensitivity, low-volume microfluidic-based surface immunoassays," Biomedical Microdevices. 7(2):99-110.

* cited by examiner

FIGURE 5
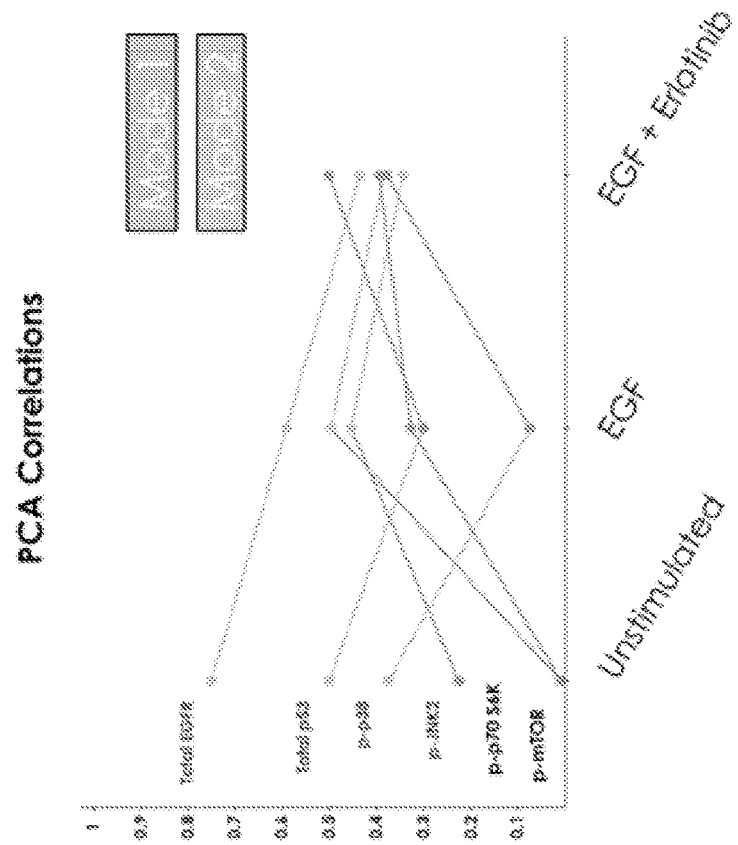
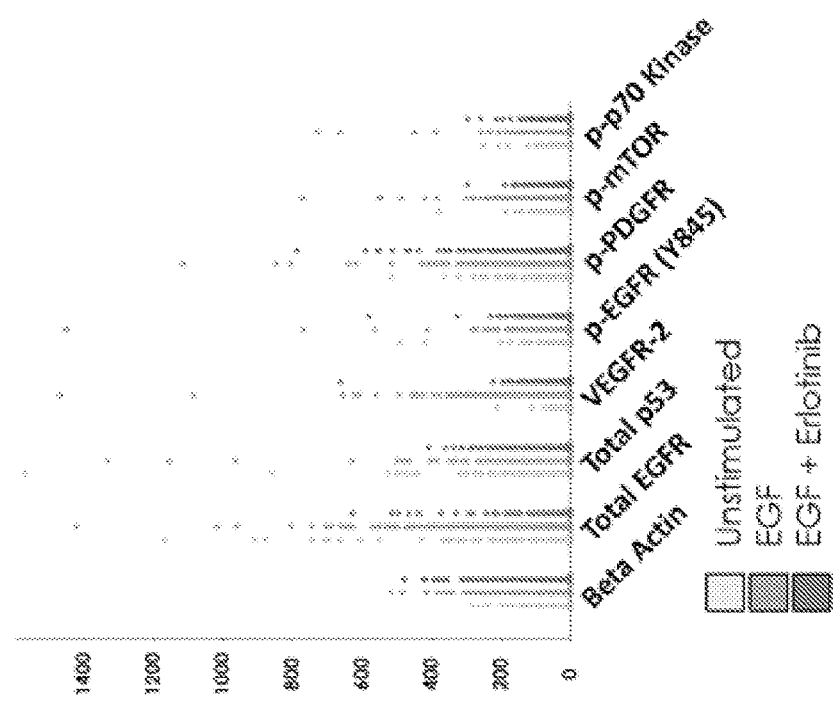

FIGURE 6
A. Total Capture Variability: Inter-assay CV: 21%
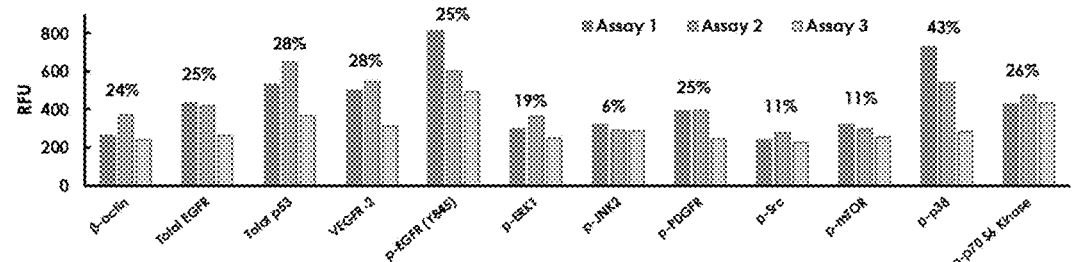
B. Signal Coordination: Very precise (>75%) with all abs on 15-plex Panel
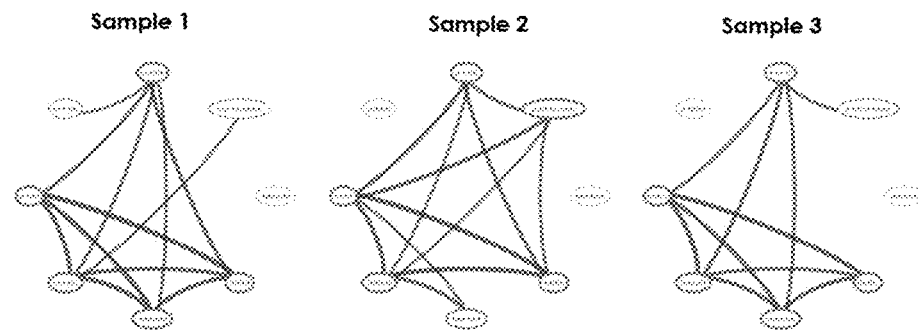
C. Target Inhibitor Signal Coordination: Easily detect changes signal coordination with EGFR target inhibitor (Erlotinib)
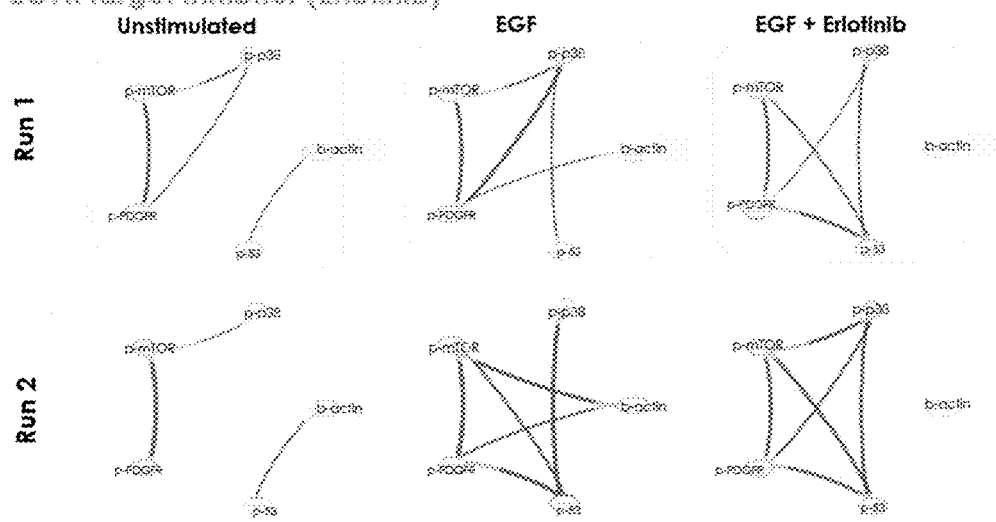

Optimization of manufacturing parameters

All manufacturing parameters analyzed to date with their effect on sCBC lysis device. APTES concentration, PVA molecular weight, PVA hydrolysis, temperature and storage time have not been explored. Current optimized conditions enable single cell lysis on Isoplexis's sCBC platform

| | Concentration | Thickness | Drug Release | Percent Sealing | Cross Linking Time | Current Best Conditions |
|---|---|---|---|---|---|---|
| PVA | ← | ← | ← | → | → | 5% |
| Triton X-100 | ← | ? | ← | → | ← | 0.2% |
| GA Coat | ← | = | → | ← | ? | 1% |
| HCl | ← | → | = | ← | → | 10% |
| GA Solution | ← | ? | → | ← | → | 0.1% |
| RPM | ← | → | → | ← | → | 3000 RPM |

Strong sealing between the cb slide and the coated PDMS chambers requires a fully cross linked hydrogel on the PDMS chambers (does not dissolve in water), a sufficiently low viscosity homogenous solution to permeate into the microchambers and an evenly coated sample devoid of bumps or bubbles post crosslinking Tuned Triton X-100 release to allow for single cell imaging prior to complete cell lysis. PVA crosslinking density dictates total drug release, higher cross linking densities lead to less total Triton X-100 release

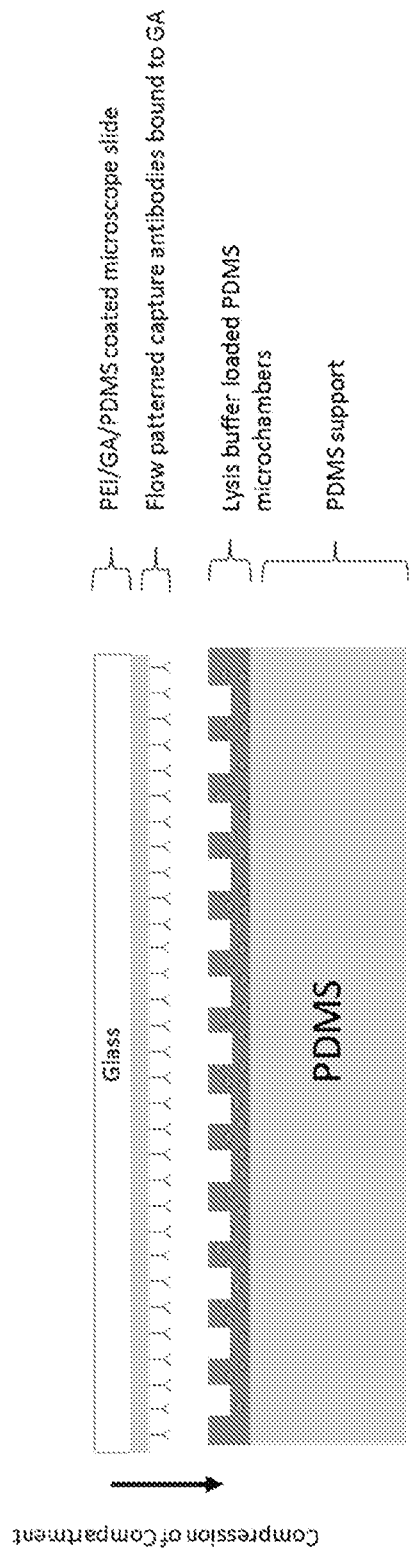

FIGURE 17
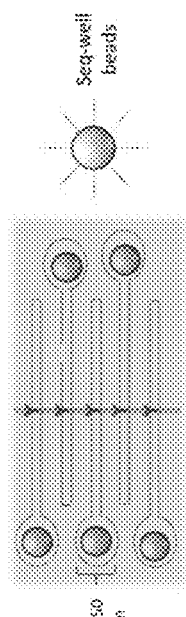
A. Spin coat of UV-crosslinkable PVA-SbQ onto microfluidic chip
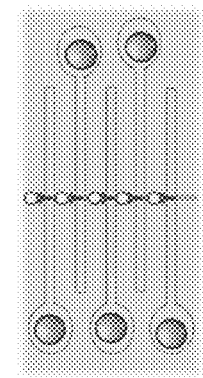
B. Regionally specific hydrogel formation by UV photolithography
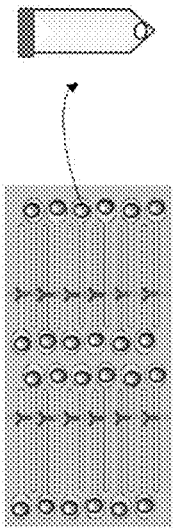
C. Antibody deposition
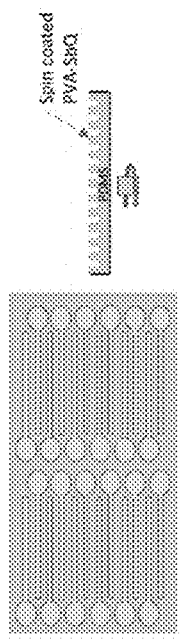
D. Bead loading into seclusion wells of microchambers.
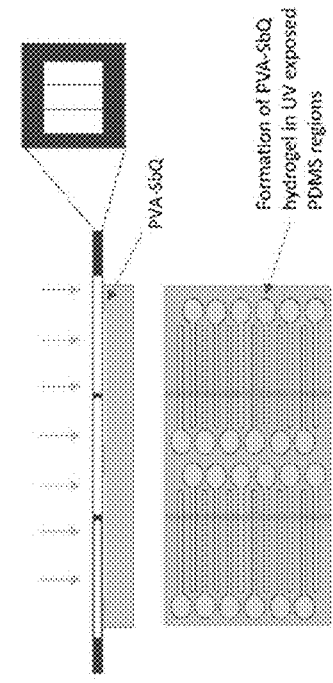
E. Cells are loaded and captured on functionalized antibody band.
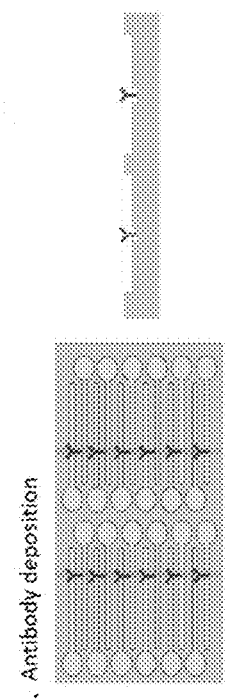
F. Beads are collected to build single cell transcriptome library for NGS.

COMPOSITIONS AND METHODS FOR THE SIMULTANEOUS GENOMIC, TRANSCRIPTOMIC AND PROTEOMIC ANALYSIS OF SINGLE CELLS

RELATED APPLICATIONS

This application is a 35 U.S.C. § 371 national stage entry of PCT International Application No.: PCT/US2017/061344, filed Nov. 13, 2017, which claims the benefit of provisional application USSN 62/421,031, filed Nov. 11, 2016, and USSN 62/544,521, filed Aug. 11, 2017, the contents of each of which are herein incorporated by reference in its entirety.

FIELD OF THE DISCLOSURE

The disclosure is directed to molecular biology, and more, specifically, to compositions and methods for the multiplexed analysis of intracellular protein components, interactions and signaling within a single cell.

BACKGROUND

There have been long-felt but unmet needs in the art for a compositions and methods for the multiplexed analysis of intracellular protein interactions and signaling within a single cell, as well as secreted protein signals blocked within cells, in a high-throughput format that can simultaneously capture and analyze hundreds of intracellular components, including DNA, RNA, metabolite, and protein levels, of each of a plurality of thousands of cells in parallel. The disclosure provides a system and methods to solve these long-felt but unmet needs.

SUMMARY

The systems of the disclosure provides compositions and methods for the multiplexed analysis of intracellular protein interactions and signaling within a single cell in a high-throughput format that can simultaneously analyze hundreds of intracellular components of each of a plurality of thousands of cells in parallel. In certain embodiments, the disclosure provides a composition for the controlled release a lysing composition, which upon contacting a cell, disrupts the membrane of the cell and exposes the intracellular components of the cell to a single repeat of a repeating pattern of capture agents. Capture agents of the disclosure specifically bind at least one intracellular component of the cell to form at least one complex. Visualization of the at least one complex (comprising a capture agent and an intracellular component), may indicate or demonstrate protein expression, protein regulation, protein-protein interactions, protein activation, and/or protein signaling events within the cell.

The disclosure provides a composition comprising: a surface comprising a plurality of capture agents operatively-linked thereto, wherein each capture agent specifically binds to a distinct intracellular target and wherein the plurality of capture agents form a repeating pattern; a substrate comprising a plurality of chambers, wherein the substrate releasably couples with the surface and wherein each chamber of the plurality of chambers comprises at least one repeat of the repeating pattern of the plurality of capture agents of the surface; a coating composition comprising a cell lysis composition; and a linker composition comprising a functionalization component and an extension component.

The disclosure provides a composition comprising: a bead comprising a plurality of capture agents operatively-linked thereto, wherein each capture agent specifically binds to a distinct intracellular target; a substrate comprising a plurality of chambers, wherein the substrate releasably couples with the surface and wherein each chamber of the plurality of chambers comprises at least one bead; a coating composition comprising a cell lysis composition; and a linker composition comprising a functionalization component and an extension component. In certain embodiments, each chamber of the plurality of chambers comprises a single bead.

In certain embodiments of the compositions of the disclosure, the plurality of capture agents comprises between 2 and 200 distinct capture agents. In certain embodiments, the plurality of capture agents comprises between 2 and 100 distinct capture agents. In certain embodiments, the plurality of capture agents comprises between 2 and 50 distinct capture agents. In certain embodiments, the plurality of capture agents comprises between 2 and 25 distinct capture agents.

In certain embodiments of the compositions of the disclosure, the plurality of chambers comprises between 2 and 20,000 chambers. In certain embodiments, the plurality of chambers comprises between 2 and 12,000 chambers. In certain embodiments, the plurality of chambers comprises between 2 and 10,000 chambers. In certain embodiments, the plurality of chambers comprises between 2 and 5,000 chambers. In certain embodiments, the plurality of chambers comprises between 2 and 2,500 chambers. In certain embodiments, the plurality of chambers comprises between 2 and 1,000 chambers. In certain embodiments, the plurality of chambers comprises between 2 and 500 chambers.

In certain embodiments of the compositions of the disclosure, each chamber of the plurality of chambers has an identical shape. In certain embodiments of the compositions of the disclosure, each chamber of the plurality of chambers has an equal value for at least one dimension. In certain embodiments, each chamber of the plurality of chambers has an equal value for each dimension. In certain embodiments of the compositions of the disclosure, at least one chamber, or each chamber of the plurality of chambers is round. In certain embodiments, at least one chamber, or each chamber of the plurality of chambers has a diameter of at least 10 μm. In certain embodiments, at least one chamber, or each chamber of the plurality of chambers has a diameter of at least 50 μm. In certain embodiments, at least one chamber, or each chamber of the plurality of chambers has a diameter of at least 100 μm. In certain embodiments, at least one chamber, or each chamber of the plurality of chambers has a depth of at least 10 μm. In certain embodiments, at least one chamber, or each chamber of the plurality of chambers has a depth of at least 50 μm. In certain embodiments, at least one chamber, or each chamber of the plurality of chambers has a depth of at least 100 μm. In certain embodiments of the compositions of the disclosure, at least one chamber, or each chamber of the plurality of chambers is rectangular. In certain embodiments, at least one chamber, or each chamber of the plurality of chambers has a length of a first side of at least 10 μm. In certain embodiments, at least one chamber, or each chamber of the plurality of chambers has a length of a first side of at least 50 μm. In certain embodiments, at least one chamber, or each chamber of the plurality of chambers has a length of a first side of at least 100 μm. In certain embodiments, at least one chamber, or each chamber of the plurality of chambers has a length of a second side of at least 10 μm. In certain embodiments, at least one chamber, or each chamber of the plurality of chambers has a length of a second side of at least 50 μm. In certain embodiments, at least one chamber, or each chamber of the plurality of chambers has a length of a second side of at least 100 μm. In certain embodiments, at least one chamber, or each chamber of the plurality of chambers has a depth of at least 10 μm. In certain embodiments, at least one chamber, or each chamber of the plurality of chambers has a depth of at least 50 μm. In certain embodiments, at least one chamber, or each chamber of the plurality of chambers has a depth of at least 100 μm.

In certain embodiments of the compositions of the disclosure, each chamber of the plurality of chambers has an equal value for at least one dimension. In certain embodiments, each chamber of the plurality of chambers has an equal value for each dimension.

In certain embodiments of the compositions of the disclosure, at least one chamber, or each chamber of the plurality of chambers is round. In certain embodiments, at least one chamber, or each chamber of the plurality of chambers has a diameter of at least 10 μm. In certain embodiments, at least one chamber, or each chamber of the plurality of chambers has a diameter of at least 50 μm. In certain embodiments, at least one chamber, or each chamber of the plurality of chambers has a diameter of at least 100 μm. In certain embodiments, at least one chamber, or each chamber of the plurality of chambers has a depth of at least 10 μm. In certain embodiments, at least one chamber, or each chamber of the plurality of chambers has a depth of at least 50 μm. In certain embodiments, at least one chamber, or each chamber of the plurality of chambers has a depth of at least 100 μm.

In certain embodiments of the compositions of the disclosure, at least one chamber, or each chamber of the plurality of chambers is rectangular. In certain embodiments, at least one chamber, or each chamber of the plurality of chambers has a length of a first side of at least 10 μm. In certain embodiments, at least one chamber, or each chamber of the plurality of chambers has a length of a first side of at least 50 μm. In certain embodiments, at least one chamber, or each chamber of the plurality of chambers has a length of a first side of at least 100 μm. In certain embodiments, at least one chamber, or each chamber of the plurality of chambers has a length of a second side of at least 10 μm. In certain embodiments, at least one chamber, or each chamber of the plurality of chambers has a length of a second side of at least 50 μm. In certain embodiments, at least one chamber, or each chamber of the plurality of chambers has a length of a second side of at least 100 μm. In certain embodiments, at least one chamber, or each chamber of the plurality of chambers has a depth of at least 10 μm. In certain embodiments, at least one chamber, or each chamber of the plurality of chambers has a depth of at least 50 μm. In certain embodiments, at least one chamber, or each chamber of the plurality of chambers has a depth of at least 100 μm.

In certain embodiments of the compositions of the disclosure, the substrate comprises a polymer. In certain embodiments, the substrate has an oxidized surface.

In certain embodiments of the compositions of the disclosure, the substrate comprises a polymer. In certain embodiments, the substrate has an oxidized surface. In certain embodiments, the polymer comprises polydimethylsiloxane (PDMS). In certain embodiments, the PDMS substrate was formed from a PDMS pre-polymer mixed with a surfactant prior to manufacture by injection molding, and, optionally, the surfactant comprises Triton-X-100.

In certain embodiments of the compositions of the disclosure, the surface comprises a glass.

In certain embodiments of the compositions of the disclosure, at least one capture agent of the plurality of capture agents comprises an oligonucleotide, an aptamer, an antibody, a functional fragment of an antibody, or an antibody mimetic.

In certain embodiments of the compositions of the disclosure, at least one capture agent of the plurality of capture agents comprises an antibody. In certain embodiments, each capture agent of the plurality of capture agents comprises an antibody.

In certain embodiments of the compositions of the disclosure, the coating composition further comprises a crosslinking composition. In certain embodiments, the crosslinking composition comprises a biocompatable polymer. For example, the biocompatable polymer may comprise poly(vinyl alcohol) (PVA). In certain embodiments, the crosslinking composition comprises poly(vinyl alcohol) (PVA). In certain embodiments, the crosslinking composition comprises 3% v/v PVA. In certain embodiments, the crosslinking composition further comprises a glutaraldehyde composition and a hydrochloric acid (HCl) composition. In certain embodiments, the glutaraldehyde composition comprises 0.1% glutaraldehyde. In certain embodiments, the HCl composition comprises 10% HCl. In certain embodiments, the crosslinking composition further comprises a glutaraldehyde composition comprising 0.1% glutaraldehyde and a hydrochloric acid (HCl) composition comprising 10%° HCl.

In certain embodiments of the compositions of the disclosure, the cell lysis composition comprises a detergent. For example, the detergent may comprise Triton-X-100. In certain embodiments, the cell lysis composition comprises Triton-X-100. In certain embodiments, the cell lysis composition comprises 0.2% Triton-X-100.

In certain embodiments of the compositions of the disclosure, the coating composition comprises a crosslinking composition comprising 3% v/v PVA and a cell lysis composition comprising 0.2% Triton-X-100. In certain embodiments, the crosslinking composition further comprises a glutaraldehyde composition comprising 0.1% glutaraldehyde and a hydrochloric acid (HCl) composition comprising 10%, HCl.

In certain embodiments of the compositions of the disclosure, the coating composition comprises a lysis composition, a signaling agent, and at least one crosslinking composition. The crosslinking composition may be optimized for a controlled release of the lysis composition, either alone, or in combination with, a signaling agent. For example, coating compositions of the disclosure may comprise a signaling agent that activates, inhibits, or alters a signaling pathway of the cell in the chamber. Lysis compositions of the disclosure may comprise a signaling agent that activates, inhibits, or alters a signaling pathway of the cell in the chamber. For example, in a coating composition of the disclosure, a lysis composition may be combined with a first crosslinking composition and a signaling agent may be combined with a second crosslinking composition, wherein the first and second crosslinking compositions are either identical or are uniquely formulated for release of either the lysis composition or the signaling agent at distinct times and/or distinct rates. In certain embodiments of a coating composition of the disclosure, a lysis composition is combined with a first crosslinking composition and a signaling agent is combined with a second crosslinking composition, wherein the first crosslinking composition is added to the substrate as a bottom layer that directly contacts the substrate and the second crosslinking composition is added on top of the first crosslinking composition as a top layer that does not directly contact the substrate. Upon contacting a cell suspension, the top layer (i.e. second crosslinking composition) of the coating composition may degrade or release the signaling agent before the bottom layer (i.e. first crosslinking composition) of the coating composition may degrade or release the lysis composition. The result of this stratified coating composition is a sequential contacting of the cell with the signaling agent followed by a contacting of the cell with the lysis composition. Without requiring moving parts or multiple channels, the compositions of the disclosure can be used to first affect cell signaling and then lyse the cell to expose the intracellular components for immediate analysis.

Exemplary signaling agents of the disclosure include, but are not limited to, ligands for cell surface and transmembrane receptors, antigens, growth factors (nerve growth factor (NGF), epidermal growth factor (EGF), platelet-derived growth factor (PDGF), interleukin-2, erythropoietin), cytokines (chemokines, interferons, interleukins, lymphokines, and tumour necrosis factors, interleukin-1 (IL-1), interleukin-2 (IL-2), interleukin-4 (IL-4), interleukin-7 (IL-7), interleukin-9 (IL-9), interleukin-15 (IL-15), interleukin-21 (IL-21), interleukin-10 (IL-10), interleukin-17 (IL-17), interleukin-18 (IL-18), interleukin-19 (IL-19), interleukin-20 (IL-20), interleukin-22 (IL-22), interleukin-24 (IL-24), interleukin-26 (IL-26), interferon (IFN) types I-III, interferon-alpha (IFN-$\alpha$), interferon-beta (IFN-$\beta$), interferon-epsilon (IFN-$\varepsilon$), interferon-kappa (IFN-$\kappa$), interferon-delta (IFN-6), interferon-tau (IFN-$\tau$), interferon-omega (IFN-$\omega$), interferon-zeta (IFN-$\zeta$), interferon-gamma (IFN-$\gamma$), interferon-lamba (IFN-$\lambda$), transforming growth factor beta 1 (TGF-$\beta 1$), transforming growth factor beta 2 (TGF-$\beta 2$) and transforming growth factor beta 3 (TGF-$\beta 3$) hormones (including, but not limited to thyroid hormone, vitamin D3, retinoic acid, testosterone, estrogen, progesterone, corticosteroids, ectysone, insulin, glucagon, growth hormone, follicle-stimulating hormone (FSH), prolactin), lipids (prostaglandins, prostacyclin, thromboxanes, and leukotrienes), peptides (insulin, glucagon, growth hormone, follicle-stimulating hormone (FSH), prolactin, substance P, oxytocin, vasopressin, enkephalins, $\beta$-endorphin, nerve growth factor (NGF), epidermal growth factor (EGF), platelet-derived growth factor (PDGF), interleukin-2, erythropoietin), pain peptides (Neurokinin A, glutamate, substance P, steroids, physiological stressors (adrenaline, noradrenaline, cortisol, adrenocorticotropic hormone, corticotropin-releasing hormone, serotonin, neuropeptide Y), neurotransmitters (acetylcholine, dopamine, epinephrine (adrenaline), serotonin, histamine, glutamate, glycine, $\gamma$-aminobutyric acid (GABA), substance P, oxytocin, vasopressin, enkephalins, $\beta$-endorphin), small molecules, ions (calcium, potassium, and sodium) gas particles (including, but not limited to nitric oxide, carbon monoxide, carbon dioxide, and oxygen ($O_2$)), synthetic ligands, synthetic agonists of cell surface and transmembrane receptors, synthetic antagonists of cell surface and transmembrane receptors, and competitive ligands of cell surface and transmembrane receptors (reversible and irreversible).

In certain embodiments of the compositions of the disclosure, the composition comprises water.

In certain embodiments of the compositions of the disclosure, the composition does not comprise water.

In certain embodiments of the compositions of the disclosure, the linker composition does not degrade at room temperature for at least 1 week. In certain embodiments, the linker composition does not degrade at room temperature for at least 1 month. In certain embodiments, the linker composition does not degrade at room temperature for at least 6 months. In certain embodiments, the linker composition does not degrade at room temperature for at least 1 year. In certain embodiments, the linker composition is "shelf stable" at a temperature range from above freezing to below boiling (adjusted as needed according to altitude) for a period of time extending from end of the manufacturing to use by the consumer. Compositions of the disclosure may be temporarily sealed for a period of time extending from end of the manufacturing to use by the consumer. As long as a composition of the disclosure is not contaminated, opened (the surface and substrate separated from one another prior to use), unsealed, boiled, frozen and/or broken, compositions of the disclosure may remain stable and efficacious for a period of time extending from end of the manufacturing to use by the consumer, which may be at least 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours or any hourly increment in between. As long as that a composition of the disclosure is not contaminated, opened (the surface and substrate separated from one another prior to use), unsealed, boiled, frozen and/or broken, compositions of the disclosure may remain stable and efficacious for a period of time extending from end of the manufacturing to use by the consumer, which may be at least 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or any daily increment in between. As long as that a composition of the disclosure is not contaminated, opened (the surface and substrate separated from one another prior to use), unsealed, boiled, frozen and/or broken, compositions of the disclosure may remain stable and efficacious for a period of time extending from end of the manufacturing to use by the consumer, which may be at least 1 week, 2 weeks, 3 weeks, 4 weeks, 5 weeks, 6 weeks, 7 weeks, 8 weeks, 9 weeks, 10 weeks, 11 weeks, 12 weeks or any weekly increment in between. As long as that a composition of the disclosure is not contaminated, opened (the surface and substrate separated from one another prior to use), unsealed, boiled, frozen and/or broken, compositions of the disclosure may remain stable and efficacious for a period of time extending from end of the manufacturing to use by the consumer, which may be at least 1 month, 2 months, 3 months, 4 months, 5 months, 6 months, 7 months, 8 months, 9 months, 10 months, 11 months, 12 months or any monthly increment in between. As long as that a composition of the disclosure is not contaminated, opened (the surface and substrate separated from one another prior to use), unsealed, boiled, frozen and/or broken, compositions of the disclosure may remain stable and efficacious for a period of time extending from end of the manufacturing to use by the consumer, which may be at least 1 year, 2 years, 3 years, 4 years, 5 years, 6 years or any yearly increment in between.

The linker component comprises a functionalization component and an extension component. In certain embodiments of the compositions of the disclosure, upon contact with the substrate, the functionalization component covalently bonds at least one functional group to a surface of the substrate. In certain embodiments, the surface comprises an interior surface of each chamber of the plurality of chambers. In certain embodiments, the surface comprises each interior surface of each chamber of the plurality of chambers.

The linker component comprises a functionalization component and an extension component. In certain embodiments of the compositions of the disclosure, upon contact with the substrate, the functionalization component covalently bonds at least one functional group to a surface of the substrate. In certain embodiments, the at least one functional group is a silane group. In certain embodiments, the functionalization component comprises an organofunctional alkoxysilane. For example, the organofunctional alkoxysilane may comprise an aminosilane. In certain embodiments, the functionalization component comprises an aminosilane. For example, the aminosilane may comprise (3-Aminopropyl)triethoxysilane (APTES). In certain embodiments, the functionalization component comprises (3-Aminopropyl)triethoxysilane (APTES). In certain embodiments, the functionalization component comprises 1% APTES.

The linker component comprises a functionalization component and an extension component. In certain embodiments of the compositions of the disclosure, the extension component comprises an organic polymer that covalently binds to the functionalization component at a first end. In certain embodiments, the organic polymer comprises an aldehyde at a second end. In certain embodiments, the extension component binds to the crosslinking composition. In certain embodiments, the extension component comprises glutaraldehyde. In certain embodiments, the extension component comprises 1% glutaraldehyde.

In certain embodiments of the compositions of the disclosure, the repeating pattern comprises a plurality of parallel lines. In certain embodiments of the compositions of the disclosure, the repeating pattern comprises a plurality of dots. In every embodiment of the repeating pattern of the plurality of capture agents, each repeat of the pattern comprises at least one of each distinct capture agent. For example, and by means of illustration, if the plurality of capture agents comprise "A", "B" and "C" which specifically bind to intracellular targets "a", "b" and "c", respectively, then each repeat of the repeating pattern of the plurality of capture agents comprises at least one "A", at least one "B" and at least one "C".

In certain embodiments of the compositions of the disclosure, the intracellular target is a DNA molecule, an RNA molecule, a peptide, a polypeptide, a protein, a protein complex, a channel, an organelle, a lipid, an oligosaccharide, a cytoskeletal element. Alternatively, or in addition, the intracellular target may be a transcript of an oncogene, an oncoprotein, transcript of a tumor suppressor gene, a tumor suppressor protein, a regulator of an oncogene, a regulator of an oncoprotein or a regulator of a tumor suppressor gene. Alternatively, or further in addition, the intracellular target may be a receptor, an enzyme, a transcription factor, or a growth factor. Alternatively, or further in addition, the intracellular target is a phosphorylized receptor or a phosphorylized enzyme. In certain embodiments, the enzyme is a kinase.

In certain embodiments of the compositions of the disclosure, the intracellular target is a DNA molecule, an RNA molecule, a peptide, a polypeptide, a protein, a protein complex, a channel, an organelle, a lipid, an oligosaccharide, a cytoskeletal element. In certain embodiments, the intracellular target comprises a transcript of an oncogene, an oncoprotein, a transcript of a tumor suppressor gene, a tumor suppressor protein, a regulator of an oncogene, a regulator of an oncoprotein or a regulator of a tumor suppressor gene. In certain embodiments, the intracellular target comprises a receptor, an enzyme, a transcription factor, or a growth factor. In certain embodiments, the intracellular target comprises a phosphorylized receptor or a phosphorylized enzyme. In certain embodiments, the enzyme is a kinase.

In certain embodiments of the compositions of the disclosure, including those wherein at least one chamber comprises a bead, the at least one chamber of the plurality of chambers further comprises a functionalized band. In certain embodiments of the compositions of the disclosure, including those wherein at least one chamber comprises a bead, each chamber of the plurality of chambers further comprises a functionalized band.

In certain embodiments of the compositions of the disclosure, the functionalized band captures a bead. In certain embodiments, the functionalized band captures at least one bead. In certain embodiments, the functionalized band captures at most one bead. In certain embodiments, the functionalized band captures only a single bead.

In certain embodiments of the compositions of the disclosure, including those wherein at least one chamber comprises a bead, the functionalized band captures a cell. In certain embodiments, the functionalized band captures at least one cell. In certain embodiments, the functionalized band captures at most one cell. In certain embodiments, the functionalized band captures only a single cell.

In certain embodiments of the compositions of the disclosure, the functionalized band captures one bead and one cell. In certain embodiments, the functionalized band captures at most one bead and at most one cell.

In certain embodiments of the compositions of the disclosure, at least one chamber of the plurality of chambers has one or more dimensions that prevents a second bead from entering the chamber or from contacting the functionalized band. In certain embodiments of the compositions of the disclosure, each chamber of the plurality of chambers has one or more dimensions that prevents a second bead from entering the chamber or from contacting the functionalized band. In certain embodiments, the one or more dimensions of the chamber is greater than any dimension of a first bead, thereby allowing the first bead to enter the chamber or contact the functionalized band. In certain embodiments, the one or more dimensions of the chamber is lesser than the sum of any dimension of the first bead and any dimension of the second bead, thereby preventing the second bead from entering the chamber or from contacting the functionalized band. In certain embodiments, the one or more dimensions of the chamber is a diameter and wherein the diameter is or is about 50 μm. In certain embodiments, the first bead has a diameter of between 30 and 40 μm, inclusive of the endpoints, thereby allowing the first bead to enter the chamber or contact the functionalized band. In certain embodiments, the sum of the diameter of the first bead and the diameter of the second bead is between 60 and 80 μm, thereby preventing the second bead from entering the chamber or from contacting the functionalized band.

In certain embodiments of the compositions of the disclosure, including those wherein at least one chamber comprises a bead, the functionalized band has a width of or of about 10 μm.

In certain embodiments of the compositions of the disclosure, including those wherein at least one chamber comprises a bead, the chamber comprising the functionalized band is prepared according to a method comprising the steps of: contacting at least one surface of the chamber with a coating composition to produce at least one coated surface, passivating of the at least one coated surface of the chamber to produce at least one passivated surface; covering a portion of the at least one passivated surface with a photomask, wherein the photomask comprises a pattern, to produce at least one masked surface; exposing the at least one masked surface to a UV light; depositing a capture antibody composition on the at least one masked surface of the chamber to produce at least one functionalized surface, contacting a bead composition to the chamber, wherein the at least one functionalized surface captures the bead, introducing a cell lysis composition to the chamber, and introducing a cell to the chamber. In certain embodiments, the chamber comprising the functionalized band is prepared according to a method further comprising the step of: removing the bead from the chamber. In certain embodiments, the chamber comprising the functionalized band is prepared according to a method further comprising the steps of: depositing a streptavidin composition in the chamber, wherein the streptavidin composition is deposited in the chamber after depositing the capture antibody composition and wherein the streptavidin composition is deposited in the chamber before introducing the bead to the chamber.

In certain embodiments of the compositions of the disclosure, including those wherein at least one chamber comprises a bead, the coating composition comprises a PVA-SbQ composition.

In certain embodiments of the compositions of the disclosure, including those wherein at least one chamber comprises a bead, the antibody composition comprises a capture antibody.

In certain embodiments of the compositions of the disclosure, including those wherein at least one chamber comprises a bead, prior to depositing the antibody composition, at least one masked surface is prepared according to a method comprising: contacting the at least one masked surface with a linker composition. In certain embodiments, the linker composition comprises an extension component. In certain embodiments, the extension component comprises an APTES composition. In certain embodiments, the linker composition comprises a functionalization component. In certain embodiments, the functionalization component comprises a protein G composition.

In certain embodiments of the compositions of the disclosure, including those wherein at least one chamber comprises a bead, the chamber comprising the functionalized band is prepared according to a method comprising the steps of: passivating of at least one surface of the chamber; covering a portion of the at least one passivated surface with a photomask, wherein the photomask comprises a pattern, to produce at least one masked surface; exposing the at least one masked surface to a UV light; depositing a capture antibody composition in the chamber; and introducing a cell to the chamber. In certain embodiments, the passivating step comprises: contacting the at least one surface of the chamber and oxygen plasma to produce at least one functionalized surface; contacting the at least one functionalized surface with pretreatment composition to produce a pretreated surface, and contacting the at least one pretreated surface with a biotin composition. In certain embodiments, the pretreatment composition comprises N-(3-Dimethylaminopropyl)-N'-ethylcarbodiimide hydrochloride (EDC) and N-Hydroxysulfosuccinimide sodium salt (Sulfo-NHS). In certain embodiments, the pretreatment composition further comprises a buffer comprising 0.05 M MES and 0.5 M NaCl. In certain embodiments, the biotin composition comprises PLL(20)-g[3.5]-PEG(2): poly-L-lysine-g-poly(ethyleneglycol)-biotin (PLL-g-PEG-biotin). In certain embodiments, the biotin composition further comprises a HEPES buffer. In certain embodiments, the pretreatment composition comprises 11.5 mg/ml of N-(3-Dimethylaminopropyl)-N'-ethylcarbodiimide hydrochloride (EDC), 19.2 mg/ml of N-Hydroxysulfosuccinimide sodium salt (Sulfo-NHS) and a buffer comprising 0.05 M MES and 0.5 M NaCl buffer. In certain embodiments, the biotin composition comprises 0.5 mg/ml of PLL(20)-g[3.5]-PEG(2): poly-L-lysine-g-poly(ethyleneglycol)-biotin (PLL-g-PEG-biotin) and a 10 mM HEPES buffer. In certain embodiments, the passivating step comprises: contacting the at least one surface of the chamber and oxygen plasma to produce at least one functionalized surface; contacting the at least one functionalized surface with pretreatment composition for 15 minutes to produce a pretreated surface, and contacting the at least one pretreated surface with a biotin composition for at least 3 hours.

In certain embodiments of the compositions of the disclosure, including those wherein at least one chamber comprises a bead, the bead comprises a composition comprising a biotinylated oligonucleotide.

In certain embodiments of the compositions of the disclosure, including those wherein at least one chamber comprises a bead, the cell composition comprises an RNAse inhibitor solution.

In certain embodiments of the compositions of the disclosure, including those wherein at least one chamber comprises a bead, the bead composition comprises a bead and nucleic acid sequence encoding a barcode, wherein the barcode comprises a sequence encoding a barcode and a sequence encoding a barcode handle. In certain embodiments, the nucleic acid sequence encoding the barcode further comprises one or more of a sequence encoding a PCR handle, a sequence encoding a unique molecular identifier (UMI), a sequence encoding a template switching oligonucleotide (TSO) handle, and a sequence encoding a TSO hybridization site. In certain embodiments, the nucleic acid sequence encoding the barcode further comprises a sequence encoding a PCR handle, a sequence encoding a unique molecular identifier (UMI), a sequence encoding a template switching oligonucleotide (TSO) handle, and a sequence encoding a TSO hybridization site. In certain embodiments, the nucleic acid sequence encoding the barcode comprises, from 5' to 3', a sequence encoding a PCR handle, a sequence encoding a barcode, a sequence encoding a barcode handle, a sequence encoding a unique molecular identifier (UMI), a sequence encoding a template switching oligonucleotide (TSO) handle, and a sequence encoding a TSO hybridization site. In certain embodiments, the sequence encoding a TSO hybridization site comprises a polyguanine (polyG) sequence. In certain embodiments, the sequence encoding a TSO hybridization site consists of a polyguanine (polyG) sequence.

In certain embodiments of the compositions of the disclosure, including those wherein at least one chamber comprises a bead, each bead of a bead composition comprises a unique barcode. In certain embodiments, each bead of each chamber comprises a unique barcode. In certain embodiments, each bead of the plurality of chambers comprises a unique barcode. In certain embodiments, the bead substrate may be interchanged with a glass slide as substrate, utilizing the same slide positioned over the chambers to capture both the mRNA as well as the protein.

In certain embodiments of the compositions of the disclosure, including those wherein at least one chamber comprises a bead, the sequence encoding the barcode comprises 12 nucleotides. In certain embodiments, the sequence encoding the barcode consists of 12 nucleotides.

In certain embodiments of the compositions of the disclosure, including those wherein at least one chamber comprises a bead, the sequence encoding the barcode comprises at least one modified nucleotide. In certain embodiments, the modified nucleotide comprises a label. In certain embodiments, the label comprises a fluorophore or a chromaphore. In certain embodiments, the label is a fluorescent label. In certain embodiments, each nucleotide of the sequence encoding the barcode comprises a label. In certain embodiments, each adenine comprise a first label, wherein each cytosine comprises a second label, each guanine comprises a third label, and each thymine comprises a fourth label. In certain embodiments, the first label, the second label, the third label, and the fourth label are distinct labels. In certain embodiments, the first label, the second label, the third label, and the fourth label are spectrally-distinguishable fluorescent labels.

In certain embodiments of the compositions of the disclosure, including those wherein at least one chamber comprises a bead, the composition further comprises a template switching oligo (TSO). In certain embodiments, the TSO comprises a sequence complementary to the sequence encoding the UMI, a sequence complementary to the sequence encoding the TSO handle, a sequence complementary to the sequence encoding the sequence encoding a TSO hybridization site, and a sequence complementary to an intracellular target RNA. In certain embodiments, the intracellular target RNA is an mRNA. In certain embodiments, the sequence complementary to the sequence encoding the sequence encoding a TSO hybridization site of the TSO hybridizes to the sequence encoding a TSO hybridization site of the nucleic acid encoding the barcode.

In certain embodiments of the compositions of the disclosure, including those wherein at least one chamber comprises a bead, the composition further comprises an intracellular target RNA. In certain embodiments, the intracellular target RNA hybridizes with the TSO.

In certain embodiments of the compositions of the disclosure, including those wherein at least one chamber comprises a bead, the composition further comprises a forward primer and a reverse primer, wherein the forward primer comprises a sequence complementary to the sequence encoding the PCR handle and wherein the second primer comprises a sequence complementary to a sequence of the intracellular target RNA. In certain embodiments, the reverse primer further comprises a primer-specific identification sequence.

In certain embodiments of the compositions of the disclosure, including those wherein at least one chamber comprises a bead, the intracellular target RNA encodes a component of a T-cell receptor (TCR). In certain embodiments, the intracellular target RNA encodes an α-chain of a TCR (TCRα). In certain embodiments, the intracellular target RNA encodes a β-chain of a TCR (TCRβ).

In certain embodiments of the compositions of the disclosure, including those wherein at least one chamber comprises a bead, the intracellular target RNA encodes a non-naturally occurring RNA or mRNA. In certain embodiments, the non-naturally occurring RNA or mRNA comprises a synthetic, modified, recombinant or chimeric sequence. In certain embodiments, the non-naturally occurring RNA or mRNA comprises a mutation when compared to a wild type version of the sequence. In certain embodiments, the mutation comprises a substitution, an insertion, a deletion, an inversion, or a transposition. In certain embodiments, the non-naturally occurring RNA or mRNA encodes a component of a TCR. In certain embodiments, the intracellular target RNA encodes an α-chain of a TCR (TCRα). In certain embodiments, the intracellular target RNA encodes a β-chain of a TCR (TCRβ).

In certain embodiments of the compositions of the disclosure, including those wherein at least one chamber comprises a bead, the intracellular target RNA encodes a non-naturally occurring RNA or mRNA. In certain embodiments, the non-naturally occurring RNA or mRNA comprises a synthetic, modified, recombinant or chimeric sequence. In certain embodiments, the non-naturally occurring RNA or mRNA comprises a mutation when compared to a wild type version of the sequence. In certain embodiments, the mutation comprises a substitution, an insertion, a deletion, an inversion, or a transposition. In certain embodiments, the non-naturally occurring RNA or mRNA encodes a fusion protein. In certain embodiments, the non-naturally occurring RNA or mRNA encodes a chimeric antigen receptor (CAR). In certain embodiments, the CAR is released from a modified cell. In certain embodiments, the modified cell is a modified T-cell.

The disclosure provides a method for the multiplexed analysis of one or more intracellular targets of a single cell, comprising contacting a biological sample and a composition of the disclosure under conditions sufficient to cause cell lysis to produce a cell lysate within each chamber of the plurality of chambers of the substrate, wherein each chamber of the plurality of chambers comprises a single cell of the biological sample, wherein the biological sample comprises a plurality of cells and a fluid, and wherein within each chamber of the plurality of chambers the biological sample is in fluid communication with the surface; incubating the cell lysate within each chamber of the plurality of chambers for a sufficient time to allow at least one capture agent of the plurality of capture agents to specifically bind to at least one intracellular target to produce a capture agent:target complex; and visualizing at least one capture agent:target complex to identify one or more intracellular targets of a single cell in a multiplexed analysis.

The disclosure provides a method for the multiplexed analysis of one or more intracellular targets of a single cell, comprising contacting a biological sample and the composition of the disclosure under conditions sufficient to cause cell lysis to produce a cell lysate within each chamber of the plurality of chambers of the substrate, wherein each chamber of the plurality of chambers comprises a single cell of the biological sample, wherein the biological sample comprises a plurality of cells and a fluid, wherein within each chamber of the plurality of chambers the biological sample is in fluid communication with a bead, and wherein the bead comprises a plurality of capture agents to specifically bind to at least one intracellular target to produce a capture agent:target complex; incubating the cell lysate within each chamber of the plurality of chambers for a sufficient time to allow at least one capture agent of the plurality of capture agents to specifically bind to at least one intracellular target to produce a capture agent:target complex; and visualizing at least one capture agent:target complex or sequencing a target of the at least one capture agent:target complex to identify one or more intracellular targets of a single cell in a multiplexed analysis. In certain embodiments, the method comprises visualizing at least one capture agent:target complex and sequencing a target of the at least one capture agent:target complex to identify one or more intracellular targets of a single cell in a multiplexed analysis.

In certain embodiments of the methods of the disclosure, including methods for the multiplexed analysis of one or more intracellular targets of a single cell, the method comprises visualizing at least one capture agent:target complex or sequencing a target of the at least one capture agent:target complex to identify one or more intracellular targets of a single cell in a multiplexed analysis.

In certain embodiments of the methods of the disclosure, including methods for the multiplexed analysis of one or more intracellular targets of a single cell, the method comprises sequencing a target of the at least one capture agent: target complex to identify one or more intracellular targets of a single cell in a multiplexed analysis.

In certain embodiments of the methods of the disclosure, including methods for the multiplexed analysis of one or more intracellular targets of a single cell, the method comprises sequencing a target of the at least one capture agent: target complex to identify one or more intracellular targets of a single cell in a multiplexed analysis.

In certain embodiments of the methods of the disclosure, including methods for the multiplexed analysis of one or more intracellular targets of a single cell, the bead composition comprises a bead and nucleic acid sequence encoding a barcode, wherein the barcode comprises a sequence encoding a barcode and a sequence encoding a barcode handle and wherein the method comprises sequencing the barcode by synthesizing a cDNA barcode sequence. In certain embodiments, synthesizing the barcode comprises contacting the sequence encoding the barcode handle, a primer comprising a sequence complementary to a portion of the sequence encoding the barcode handle and a polymerase, under conditions sufficient for hybridization and cDNA synthesis, wherein the contacting produces a cDNA barcode sequence. In certain embodiments, the sequencing step is performed in the chamber. In certain embodiments, the nucleic acid sequence encoding the barcode further comprises one or more of a sequence encoding a PCR handle, a sequence encoding a unique molecular identifier (UMI), a sequence encoding a template switching oligonucleotide (TSO) handle, and a sequence encoding a TSO hybridization site. In certain embodiments, the nucleic acid sequence encoding the barcode further comprises a sequence encoding a PCR handle, a sequence encoding a unique molecular identifier (UMI), a sequence encoding a template switching oligonucleotide (TSO) handle, and a sequence encoding a TSO hybridization site. In certain embodiments, the nucleic acid sequence encoding the barcode comprises, from 5' to 3', a sequence encoding a PCR handle, a sequence encoding a barcode, a sequence encoding a barcode handle, a sequence encoding a unique molecular identifier (UMI), a sequence encoding a template switching oligonucleotide (TSO) handle, and a sequence encoding a TSO hybridization site. In certain embodiments, the sequence encoding a TSO hybridization site comprises a polyguanine (polyG) sequence. In certain embodiments, the sequence encoding a TSO hybridization site consists of a polyguanine (polyG) sequence. In certain embodiments, each bead of a bead composition comprises a unique barcode. In certain embodiments, each bead of each chamber comprises a unique barcode. In certain embodiments, each bead of the plurality of chambers comprises a unique barcode. In certain embodiments, the sequence encoding the barcode comprises 12 nucleotides.

In certain embodiments of the methods of the disclosure, including methods for the multiplexed analysis of one or more intracellular targets of a single cell, the sequence encoding the barcode consists of 12 nucleotides. In certain embodiments, the conditions sufficient for hybridization and cDNA synthesis comprise a plurality of deoxynucleotides (dNTPs). In certain embodiments, at least one dNTP of the plurality of deoxynucleotides (dNTPs) comprises a modification. In certain embodiments, each dNTP of the plurality of deoxynucleotides (dNTPs) comprises a modification. In certain embodiments, the modification comprises a label. In certain embodiments, the label comprises a fluorophore or a chromaphore. In certain embodiments, the label is a fluorescent label. In certain embodiments, each adenine comprise a first label, wherein each cytosine comprises a second label, each guanine comprises a third label, and each thymine comprises a fourth label. In certain embodiments, the first label, the second label, the third label, and the fourth label are distinct labels. In certain embodiments, the first label, the second label, the third label, and the fourth label are spectrally-distinguishable fluorescent labels.

The disclosure provides a cDNA barcode sequence produced according to the method of the disclosure.

The disclosure provides composition comprising the cDNA barcode sequence of the disclosure.

In certain embodiments of the methods of the disclosure, including methods for the multiplexed analysis of one or more intracellular targets of a single cell, the methods further comprise contacting the nucleic acid sequence encoding the barcode of the bead and a TSO under conditions sufficient for hybridization of the TSO to a portion of the nucleic acid encoding the barcode to produce a nucleic acid/TSO duplex. In certain embodiments, the TSO comprises a sequence complementary to the sequence encoding the UMI, a sequence complementary to the sequence encoding the TSO handle, a sequence complementary to the sequence encoding the sequence encoding a TSO hybridization site, and a sequence complementary to an intracellular target RNA. In certain embodiments, the intracellular target RNA is an mRNA. In certain embodiments, the sequence complementary to the sequence encoding a TSO hybridization site of the TSO hybridizes to the sequence encoding a TSO hybridization site of the nucleic acid encoding the barcode. In certain embodiments, the TSO hybridizes with an intracellular target RNA to form a nucleic acid:TSO:intracellular target RNA triplex.

In certain embodiments of the methods of the disclosure, including methods for the multiplexed analysis of one or more intracellular targets of a single cell, the methods further comprise contacting the nucleic acid:TSO:intracellular target RNA triplex, a forward primer, a reverse primer, and a polymerase, under conditions sufficient for hybridization and amplification, wherein the forward primer comprises a sequence complementary to the sequence encoding the PCR handle of the nucleic acid encoding the barcode and wherein the second primer comprises a sequence complementary to a sequence of the intracellular target RNA to produce an amplification product. In certain embodiments, the amplification product comprises a sequence encoding the barcode, a sequence encoding the barcode handle, a sequence encoding a UMI, a sequencing encoding the TSO handle, a sequence encoding a TSO hybridization site, and a sequence encoding the intracellular target RNA.

In certain embodiments of the methods of the disclosure, including methods for the multiplexed analysis of one or more intracellular targets of a single cell, the methods further comprise contacting the amplification product with a second forward primer, a second reverse primer, and a polymerase, under conditions sufficient for hybridization and amplification, wherein the second forward primer comprises a sequence complementary to the sequence encoding the PCR handle of the amplification product and wherein the second reverse primer comprises a sequence complementary to a sequence of the intracellular target RNA of the amplification product to produce a first sequencing product. In certain embodiments, the second reverse primer further comprises a primer-specific identification sequence.

In certain embodiments of the methods of the disclosure, including methods for the multiplexed analysis of one or more intracellular targets of a single cell, the intracellular target RNA encodes a component of a T-cell receptor (TCR). In certain embodiments, the intracellular target RNA encodes an α-chain of a TCR (TCRα). In certain embodiments, the intracellular target RNA encodes a β-chain of a TCR (TCRβ).

In certain embodiments of the methods of the disclosure, including methods for the multiplexed analysis of one or more intracellular targets of a single cell, the intracellular target RNA encodes a non-naturally occurring RNA or mRNA. In certain embodiments, the non-naturally occurring RNA or mRNA comprises a synthetic, modified, recombinant or chimeric sequence. In certain embodiments, the non-naturally occurring RNA or mRNA comprises a mutation when compared to a wild type version of the sequence. In certain embodiments, the mutation comprises a substitution, an insertion, a deletion, an inversion, or a transposition. In certain embodiments, the non-naturally occurring RNA or mRNA encodes a component of a TCR. In certain embodiments, the intracellular target RNA encodes an α-chain of a TCR (TCRα). In certain embodiments, the intracellular target RNA encodes a β-chain of a TCR (TCRβ).

In certain embodiments of the methods of the disclosure, including methods for the multiplexed analysis of one or more intracellular targets of a single cell, the intracellular target RNA encodes a non-naturally occurring RNA or mRNA. In certain embodiments, the non-naturally occurring RNA or mRNA comprises a synthetic, modified, recombinant or chimeric sequence. In certain embodiments, the non-naturally occurring RNA or mRNA comprises a mutation when compared to a wild type version of the sequence. In certain embodiments, the mutation comprises a substitution, an insertion, a deletion, an inversion, or a transposition. In certain embodiments, the non-naturally occurring RNA or mRNA encodes a fusion protein. In certain embodiments, the non-naturally occurring RNA or mRNA encodes a chimeric antigen receptor (CAR). In certain embodiments, the CAR is released from a modified cell. In certain embodiments, the modified cell is a modified T-cell.

In certain embodiments of the methods of the disclosure, the single cell is a healthy cell. In certain embodiments, the single cell is genetically-modified.

In certain embodiments of the methods of the disclosure, the single cell is not a healthy cell. In certain embodiments, the single cell is isolated, purified, or derived from an infected or diseased tissue. In certain embodiments, the single cell is isolated, purified, or derived from an infected or diseased tissue or fluid. In certain embodiments, the single cell contains a genetic or epigenetic marker that is causative, predictive, or correlated with an undesirable state of health, disease or disorder. In certain embodiments, the single cell contains a genetic or epigenetic marker that is causative, predictive, or correlated with a significantly increased risk of developing an undesirable state of health, disease, or disorder compared to the risk in the absence of the genetic or epigenetic marker. In certain embodiments, the single cell is genetically-modified.

In certain embodiments of the methods of the disclosure, the single cell is a tumor cell. In certain embodiments, the tumor cell is benign. In certain embodiments, the tumor cell is malignant. In certain embodiments, the tumor cell is a cancer cell. In certain embodiments, the single cell is a malignant cell. In certain embodiments, the single cell is a cancer cell. Cancer cells of the disclosure may be isolated, purified, derived and/or cultured from any tissue of the body, including, but not limited to, a solid tissue or a biological fluid.

In certain embodiments of the methods of the disclosure, the single cell is a neuronal cell. For example, the single cell is a may be a neuron, a neural precursor, a neural stem cell, or a cell capable of differentiating into a neural cell. In certain embodiments, the neuronal cell may be isolated, purified, or derived from a tissue or fluid of the central nervous system. In certain embodiments, the neuronal cell may be isolated, purified, or derived from a tissue or fluid of the peripheral nervous system. In certain embodiments, the single cell is genetically-modified.

In certain embodiments of the methods of the disclosure, the single cell is a glial cell. In certain embodiments, the glial cell may support a neuronal cell (e.g. a neuroglial cell, a radial glial cell, an astrocyte, an oligodendrocyte, a microglial cell, an ependymal cell, a Schwann cell or a satellite cell). In certain embodiments, the glial cell may be isolated, purified, or derived from a tissue or fluid of the central nervous system. In certain embodiments, the glial cell may be isolated, purified, or derived from a tissue or fluid of the peripheral nervous system. In certain embodiments, the glial cell may maintain a homeostatic state of a neuronal cell. In certain embodiments, the glial cell may produce, form and/or maintain a myelin or a myelin sheath around an axon. In certain embodiments, the glial cell may clear one or more signaling molecules from a synaptic cleft. In certain embodiments, the glial cell may provide one or more supportive factors or growth factors for a neuronal cell or a local microenvironment. In certain embodiments, the glial cell may facilitate removal of waste products from an intercellular space in proximity to a neuronal cell. In certain embodiments, the single cell is genetically-modified.

In certain embodiments of the methods of the disclosure, the single cell is an immune cell. In certain embodiments, the single cell is a B-lymphocyte. In certain embodiments, the single cell is a leukocyte. Exemplary leukocytes include, but are not limited to, phagocytes (macrophages, neutrophils, and dendritic cells), lymphoid cells (e.g. lymphocytes), mast cells, eosinophils, basophils, and natural killer cells. In certain embodiments, the single cell is a lymphocyte. In certain embodiments, the single cell is a T-lymphocyte or a B-lymphocyte. In certain embodiments, the single cell is a T-lymphocyte. In certain embodiments, the single cell is genetically-modified.

In certain embodiments of the methods of the disclosure, the single cell is a bacterium. Exemplary bacterium may be of any species. Exemplary bacterium may be isolated, purified, derived or cultured from a biofilm. Exemplary bacterium may have a mutualistic or symbiotic association with a host. Exemplary bacterium may have a pathogenic association with a host. In certain embodiments, the host is a vertebrate. In certain embodiments, the host is a mammal. In certain embodiments, the host is a human. In certain embodiments, the single cell is genetically-modified.

In certain embodiments of the methods of the disclosure, the single cell is an archaeon. Exemplary archaeon may be of any species. Exemplary archaeon may be isolated, purified, derived or cultured from a plurality or population of archaea. In certain embodiments, the single cell is genetically-modified.

In certain embodiments of the methods of the disclosure, the single cell is a yeast cell. Exemplary yeast cell may be of any species. Exemplary yeast cell may be isolated, purified, derived or cultured from a plurality or population of yeast cells. In certain embodiments, the single cell is genetically-modified.

In certain embodiments of the methods of the disclosure, the single cell is an alga. Exemplary alga may be of any species. Exemplary alga may be isolated, purified, derived or cultured from a plurality or population of algae. In certain embodiments, the single cell is genetically-modified.

In certain embodiments of the methods of the disclosure, the single cell is genetically-modified. In certain embodiments, the single cell is genetically-modified for use as a cellular therapy to treat a disease or disorder of the disclosure.

In certain embodiments of the methods of the disclosure, the biological sample comprises any bodily fluid. In certain embodiments, the biological sample comprises blood, cerebral spinal fluid (CSF), lymph fluid, plural effusion, urine or saliva. In certain embodiments, the biological sample is obtained from a single subject or donor. In certain embodiments, the biological sample is obtained from at least one subject or donor. In certain embodiments, the biological sample is obtained from one or more subject(s) or donor(s). In certain embodiments, the biological sample is obtained from a plurality of subject(s) or donor(s).

In certain embodiments of the methods of the disclosure, the biological sample comprises a cell culture media. In certain embodiments, the biological sample comprises a biopsy obtained from a subject and maintained as a primary culture. In certain embodiments, the biological sample comprises a biopsy obtained from a subject and maintained as an immortalized culture.

In certain embodiments of the methods of the disclosure, the biological sample comprises a tissue sample or a tissue biopsy. In certain embodiments, the tissue sample or tissue biopsy is obtained from any tissue of a vertebrate body. In certain embodiments, the tissue sample or tissue biopsy is obtained from any tissue of a mammalian body. In certain embodiments, the tissue sample or tissue biopsy is obtained from any tissue of a human body. In certain embodiments, the tissue sample or tissue biopsy is obtained from any organ, including, those organs extracted from a body as well as any organ synthesized in vitro. In certain embodiments, the tissue sample or tissue biopsy is obtained from any tissue synthesized in vitro (e.g. grown or printed in vitro).

In certain embodiments of the methods of the disclosure, the biological sample comprises a bodily fluid or fluid biopsy. In certain embodiments, the bodily fluid or fluid biopsy is obtained from any fluid of a vertebrate body. In certain embodiments, the bodily fluid or fluid biopsy is obtained from any fluid of a mammalian body. In certain embodiments, the bodily fluid or fluid biopsy is obtained from any fluid of a human body. In certain embodiments, the bodily fluid or fluid biopsy is obtained from any fluid, including, those fluids extracted from a body as well as any fluid synthesized in vitro.

In certain embodiments of the methods of the disclosure, the subject is healthy.

In certain embodiments of the methods of the disclosure, the subject not healthy. In certain embodiments, the subject has an infection, disease, or disorder. In certain embodiments, the subject has an infected or diseased tissue or fluid. In certain embodiments, the subject has a genetic or epigenetic marker that is causative, predictive, or correlated with an undesirable state of health, disease or disorder. In certain embodiments, the subject has a genetic or epigenetic marker that is causative, predictive, or correlated with a significantly increased risk of developing an undesirable state of health, disease, or disorder compared to the risk in the absence of the genetic or epigenetic marker. In certain embodiments in which the subject is not a human embryo, the subject may comprise one or more genetically-modified cells.

In certain embodiments of the methods of the disclosure, the subject has a tumor. In certain embodiments, the tumor cell is benign. In certain embodiments, the tumor cell is malignant. In certain embodiments, the tumor cell is a cancer cell. In certain embodiments, the subject has cancer. In certain embodiments, the subject has at least one cancer. In certain embodiments, the subject has one or more cancers. In certain embodiments, the subject has an aggressive form of cancer. In certain embodiments, the subject has a rare cancer or a rare form of a cancer (e.g. a cancer or a form of cancer affecting less than 10%, 5%, 2%, 1% or any percentage in between of any population defined by age, gender, genetic and/or epigenetic disposition, exposure to risk factors and/or family history). In certain embodiments, the subject has metastatic cancer. Subjects of the disclosure may have a tumor or a cancer cell located in or derived from any tissue of the body, including, but not limited to, a solid tissue or a biological fluid.

In certain embodiments of the methods of the disclosure, the subject has a cancer. The cancer may be adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and/or Wilm's Tumor.

In certain embodiments of the methods of the disclosure, the subject has an infection. In certain embodiments, the infection is bacterial. In certain embodiments, the infection is viral. In certain embodiments, the infection is fungal. In certain embodiments, the infection is microbial. Infectious agents of the disclosure may be of any species.

In certain embodiments of the methods of the disclosure, the subject has an immune disorder. In certain embodiments of the methods of the disclosure, the subject has an immunodeficiency disorder. In certain embodiments, the subject has a primary or congenital immunodeficiency disorder. Exemplary primary or congenital immunodeficiency disorders include, but are not limited to, ataxia-telangiectasia, Chediak-Higashi syndrome, combined immunodeficiency disease, complement deficiencies, DiGeorge syndrome, hypogammaglobulinemia, Job syndrome, leukocyte adhesion defects, panhypogammaglobulinemia, Bruton's disease, congenital agammaglobulinemia, selective deficiency of IgA, and Wiskott-Aldrich syndrome. In certain embodiments, the subject has a secondary or acquired immunodeficiency disorder. Exemplary secondary or acquired immunodeficiency disorders include, but are not limited to, a weakening of the immune system as a result of an infection (e.g. HIV and AIDS), a cancer of the immune system (e.g. leukemia), a cancer of the blood plasma cells (e.g. multiple myeloma), an immune-complex disorder (e.g. viral hepatitis), a severe burn, a medical therapy (e.g. chemotherapy and radiation), exposure to radiation or a toxic chemical, and malnutrition.

In certain embodiments of the methods of the disclosure, the subject has an autoimmune disorder. In certain embodiments, the disorder is congenital. In certain embodiments, the disorder has a genetic and/or epigenetic cause. Exemplary autoimmune disorders include, but are not limited to, alopecia areata, autoimmune hemolytic anemia, autoimmune hepatitis, dermatomyositis, diabetes (type 1), some forms of juvenile idiopathic arthritis, glomerulonephritis, Graves' disease, Guillain-Barre syndrome, idiopathic thrombocytopenic purpura, myasthenia gravis, some forms of myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus erythematosus, some forms of thyroiditis, some forms of uveitis, vitiligo and granulomatosis with polyangiitis (Wegener's).

In certain embodiments of the methods of the disclosure, the subject has an inflammatory disorder. In certain embodiments, the disorder is congenital. In certain embodiments, the disorder has a genetic and/or epigenetic cause. Exemplary inflammatory disorders include, but are not limited to, a disease resulting from long-term oxidative stress, Alzheimer's disease, ankylosing spondylitis, arthritis (osteoarthritis, rheumatoid arthritis (RA), psoriatic arthritis), asthma, atherosclerosis, Crohn's disease, colitis, dermatitis, diverticulitis, fibromyalgia, hepatitis, irritable bowel syndrome (IBS), systemic lupus erythematous (SLE), nephritis, Parkinson's disease and ulcerative colitis.

In certain embodiments of the methods of the disclosure, the subject has a neurological disorder. In certain embodiments, the disorder is congenital. In certain embodiments, the disorder has a genetic and/or epigenetic cause. In certain embodiments, the neurological disorder affects the central nervous system. In certain embodiments, the neurological disorder affects the peripheral nervous system. In certain embodiments, the neurological disorder affects the autonomic nervous system. In certain embodiments, the neurological disorder affects the sympathetic nervous system. In certain embodiments, the neurological disorder affects the parasympathetic nervous system. In certain embodiments, the neurological disorder is congenital. In certain embodiments, the neurological disorder is progressive. In certain embodiments, the neurological disorder is degenerative. In certain embodiments, the neurological disorder affects older adults (e.g. adults of at least 70 years, 80 years, 90 years, 100 years or any age in between). In certain embodiments, the neurological disorder affects voluntary or involuntary movement. In certain embodiments, the neurological disorder affects one or more senses including, but not limited to vision, hearing, olfaction, touch and taste. In certain embodiments, the neurological disorder affects language processing, including, but not limited to, language comprehension, ideation and communication (verbal and/or written). In certain embodiments, the neurological disorder affects memory. In certain embodiments, the neurological disorder affects communication and control of pain signals. In certain embodiments, the neurological disorder affects movement and/or coordination of the muscles of the heart and/or vasculature. In certain embodiments, the neurological disorder affects sleep. Exemplary neurological diseases include, but are not limited to, Alzheimer's Disease, Parkinson's Disease, Amyotrophic Lateral Sclerosis (ALS), autonomic dysfunction, ataxia, dementia, neuropathy, paralysis, Huntington's Disease, epilepsy, migraine, motor neuron disease, multiple sclerosis, muscular dystrophy, narcolepsy, neurodegeneration, and traumatic injury (brain and/or spinal cord). In certain embodiments, the neurological disorder is secondary to a medical treatment, another medical condition or a traumatic injury (e.g. concussion).

In certain embodiments of the methods of the disclosure, the subject has a metabolic disorder. In certain embodiments, the disorder is congenital. In certain embodiments, the disorder has a genetic and/or epigenetic cause. In certain embodiments, the disorder is acquired or secondary to another medical condition. Exemplary metabolic disorders of the disclosure include, but are not limited to, acid-base imbalance disorders, metabolic brain diseases, calcium metabolism disorders, DNA repair-deficiency disorders, glucose metabolism disorders, hyperlactatemia, iron metabolism disorders, lipid metabolism disorders, malabsorption syndromes, metabolic syndrome X, mitochondrial diseases, phosphorus metabolism disorders, porphyrias and proteostasis deficiency.

In certain embodiments of the methods of the disclosure, the subject has a degenerative disorder. Exemplary degenerative disorders of the disclosure increase damage to cells, tissue, and organs. Often this damage accumulates, leading to an increase in severity of one or more symptoms over time.

In certain embodiments of the methods of the disclosure, the subject has a progressive disorder. Exemplary progressive disorders of the disclosure increase in severity as a function of time. Severity includes both the quality and quantity of a symptom as well as the physical spread of a disease. An increase in the severity of a disease may also include an increasingly negative prognosis.

In certain embodiments of the methods of the disclosure, the subject has a genetic mutation and/or an epigenetic modification associated with a disease or disorder. The genetic mutation and/or epigenetic modification may be a biomarker for the disease or disorder. The genetic mutation and/or epigenetic modification may be correlated with an increased or decreased occurrence of the disease or disorder. The genetic mutation and/or epigenetic modification may be predictive of an increased or decreased occurrence of the disease or disorder. The genetic mutation and/or epigenetic modification may be causative of an increased or decreased occurrence of the disease or disorder.

In certain embodiments of the methods of the disclosure, the visualizing comprises contacting the at least one capture agent:target complex with a labeled secondary antibody that binds the capture agent and detecting the labeled secondary antibody. In certain embodiments of the visualizing step, the labeled secondary antibody comprises a fluorescent, gold or silver label. In certain embodiments, the visualizing comprises contacting a first capture agent:target complex with a first labeled secondary antibody that binds the first capture agent, contacting a second capture agent:target complex with a second labeled secondary antibody that binds the second capture agent, and detecting the first labeled secondary antibody and the second labeled secondary antibody, wherein the first labeled secondary antibody and the second labeled secondary antibody each comprise a distinct label.

In certain embodiments of the methods of the disclosure, the method further comprises quantifying the at least one intracellular target. In certain embodiments, the quantifying step comprises measuring an intensity and/or a density of the labeled secondary antibody. In certain embodiments, the intracellular target is a phosphoprotein.

BRIEF DESCRIPTION OF THE DRAWINGS

This patent or application file contains at least one drawing executed in color. Copies of this patent or patent application publication with color drawings(s) will be provided by the Office upon request and payment of the necessary fee.

FIG. 5A is a scatter plot demonstrating total protein capture following single cell lysis produced by the controlled lysis composition and/or signaling agent release by the coating compositions of the disclosure. Utilizing the protein intensities from each cell, protein to protein correlations can be elicited to determine signal coordination.

FIG. 5B is a graph demonstrating how adaptive resistance can be evaluated to target inhibitors by detecting the activation of secondary pathways. This data can be used for selection and optimization of drug combinations for target therapy in, for example, glioblastoma.

FIG. 6A-C is a series of graphs demonstrating the sample-to-sample consistency of analysis using a composition of the disclosure comprising U87 glioblastoma tumor cells. Panel A shows an inter-assay coefficient of variation (CV) of 21% for the total protein capture which meets the current pharma standards for a single cell device (CV<25 to 30%). Panel B shows a consistent analysis of protein-protein correlation with a precision of >75% between all proteins and all samples. Panel C shows consistent and differential analysis of unstimulated, EGF and EGF/Erlotinib treated U87 cells.

Figure 10:
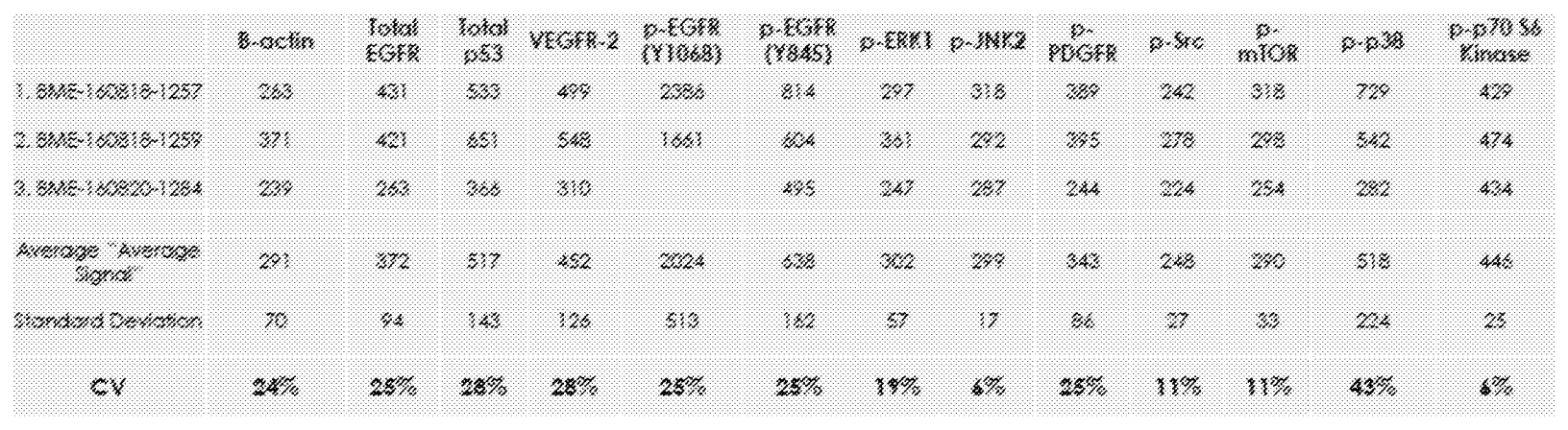

FIG. 10 is a table providing data for inter-assay variability of average protein capture using the controlled release method. As shown by the data, the inter-assay variability is low, with an average variability of 21%.

FIG. 12 is a table summarizing the optimization of substrate pre-coating and the coating composition for a PDMS substrate pre-coated with glutaraldehyde and a coating composition including a lysis composition comprising Triton-X-100 and a crosslinking composition comprising PVA.

FIG. 13 is a schematic diagram depicting an exemplary composition of the disclosure.

FIG. 17A-F is a series of schematic drawings depicting a sequencing protocol for single-bead, single-cell capture with size exclusion wells. A. UV cross-linkable PVA is spin-coated onto the microchamber surface. B. Using a negative photomask, PVA is crosslinked forming a PVA hydrogel on microchamber surface with exception of 10 µM bands not exposed to UV light. C. Exposed PDMS is functionalized with amine groups/glutaraldehyde for antibody immobilization D. Seq-well beads are added to the microchambers and become trapped in the exclusion wells and excess beads are rinsed off. E. Cell suspension is pipetted onto PDMS surface, single cells are captured in cell trap in each microchamber and excess cells are rinsed off. F. Microchambers are sealed with antibody slide and cells are lysed releasing mRNA. mRNA transcripts are hybridized to Drop-Seq beads after 3 hours. Slide is removed from PDMS and beads are removed for off chip sequencing.

DETAILED DESCRIPTION

The disclosure provides compositions and methods for the multiplexed analysis of intracellular protein interactions and signaling within a single cell in a high-throughput format that can simultaneously analyze hundreds of intracellular components of each of a plurality of thousands of cells in parallel. In certain embodiments, the disclosure provides a composition for the controlled release a lysing composition, which upon contacting a cell, disrupts the membrane of the cell and exposes the intracellular components of the cell to a single repeat of a repeating pattern of capture agents. Capture agents of the disclosure specifically bind at least one intracellular component of the cell to form at least one complex. Visualization of the at least one complex (comprising a capture agent and an intracellular component), may indicate or demonstrate protein expression, protein regulation, protein-protein interactions, protein activation, and/or protein signaling events within the cell.

Intracellular Components and Interactions Thereof

Although signal transduction inhibitors can offer clinical benefit for cancer patients, signal flux emanating from oncogenes is often distributed through multiple pathways, potentially underlying the failure of most such inhibitors. Measuring signal flux through multiple pathways, for example, in response to signal transduction inhibitors using the compositions and methods of the disclosure, reveals network interactions that contribute to therapeutic resistance and that could not be predicted by analyzing individual pathways in isolation. Although this illustrative example describes oncogenic pathways, the same principles apply to nearly every cellular process that leads to the development of a disease or disorder of the disclosure. Cellular outcomes are rarely the result of a single signaling pathway, but rather, interactions between multiple pathways.

The compositions and methods of the disclosure are designed to accommodate the cellular and molecular complexity of an in vivo microenvironment, including, for example, a solid tumor microenvironment, by using a highly multiplexed reaction to identify the intracellular components and signaling events within a single cell, while, simultaneously, performing the same analysis on thousands of single cells under identical conditions. Thus, the compositions and methods of the disclosure provide both the detailed analysis that recapitulates the complexity of the intracellular and in vivo microenvironments while providing sufficient statistical power within a single experiment to draw significant conclusions.

Controlled Release

Figure 1:
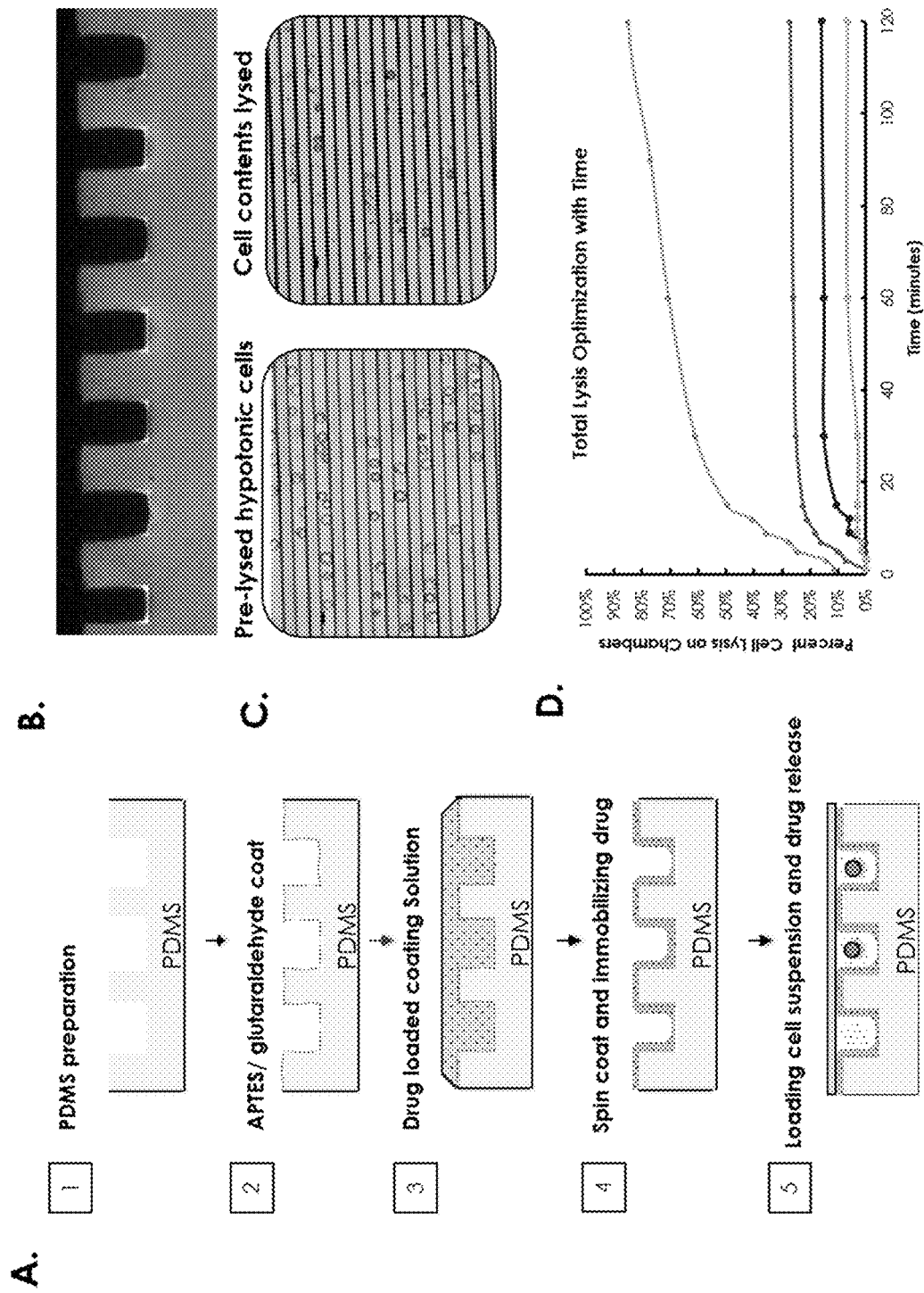
FIG. 1A is a schematic depiction of the processes of coating a substrate of the composition and lysing a single cell within a chamber of the substrate. The process begins by 1) preparing the microchambers for surface functionalization. 2) APTES then glutaraldehyde is coating on the chamber to link the coating to the PDMS microchambers. 3) Lysis composition and/or signaling agent loaded PVA solution is prepared and loaded onto the microchambers. 4) PVA film immobilizes lysis composition and/or signaling agent onto the PDMS chambers by spin coating. 5) Cell suspension is loaded and the surface comprising the plurality of capture agents attached for protein capture.
FIG. 1B is a photograph depicting a substrate of the disclosure including a coating composition comprising Fluorescein IsoThioCyanate (FITC) in order to visualize the coating composition on microchambers. The cross section image was taken showing PVA coat on microchambers.
FIG. 1C is a photograph depicting microchambers of a substrate of the disclosure overloaded with cells to fully illustrate cell lysis within the microchambers at T=0 and T=30 minutes (at which time nearly all of the cells are completely lysed).
FIG. 1D is a graph depicting the total lysis optimization with time. The optimum lysis (top line, orange) was selected showing 70% lysis after 30 minutes.
Figure 2:
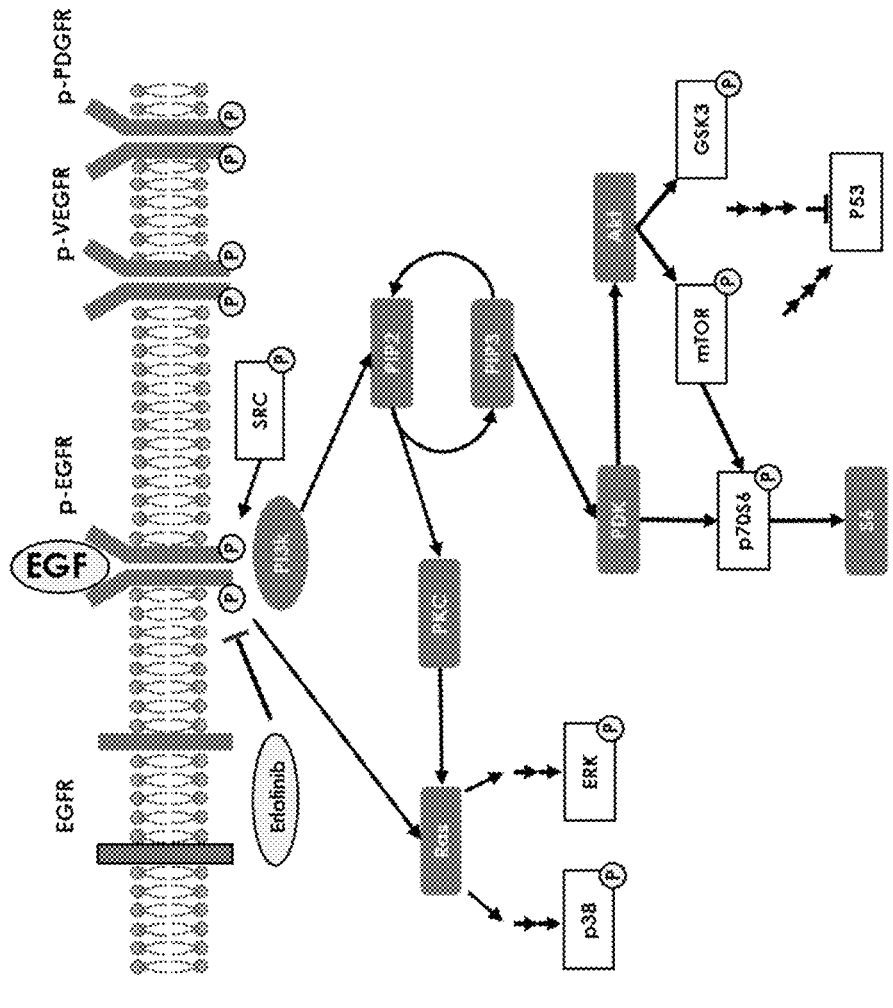
FIG. 2 is a schematic depiction of the signaling pathways in which the components of the 14-plex antibody panel developed for studying EGFR signaling pathway are involved. The highly multiplex panel used by the compositions of the disclosure monitors key intracellular proteins along multiple signal transduction pathways. Signaling agent (drug) effectiveness and resistance via non-genetic (adaptive) mechanisms can be detected within days allowing for clinically actionable insights into the design of combination therapy strategies in, for example, glioblastoma (GBM) patients. The presented panel can be expanded by adding more antibodies spatially (more antibodies per repeat of the repeating pattern of capture agents of the compositions of the disclosure) and spectrally (a wider range of labeled secondary antibodies or more sensitive detection methods).
Figure 3:
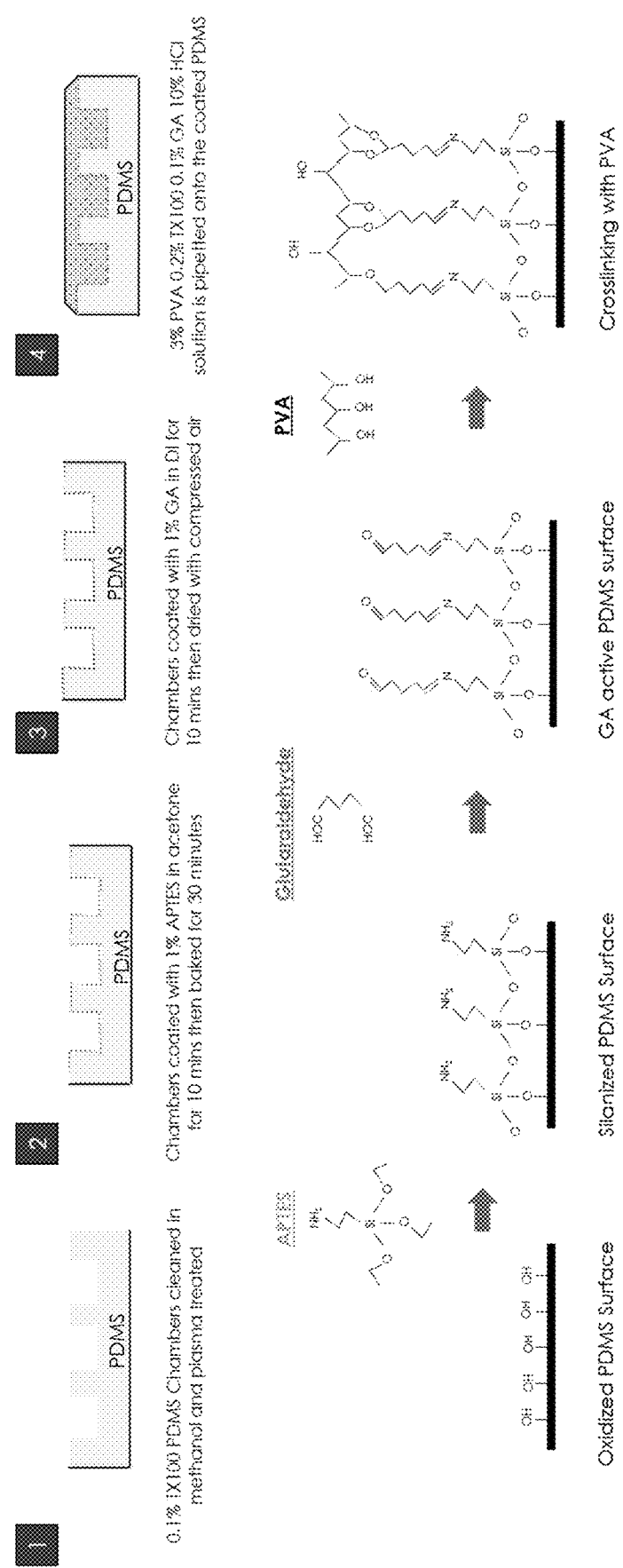
FIG. 3 is a schematic diagram depicting the PDMS/PVA binding chemistry and preparation of an APTES/GA linker of the disclosure. 1) 0.1% Triton X-100 PDMS microchambers are cleaned with methanol before an oxygen plasma treatment. The oxygen plasma is used to modify the PDMS surface in order to introduce polar functional groups which mainly the silanol group (SiOH) required for APTES functionalization. 2) Chambers are then coated with 1% APTES in acetone for 10 minutes, silanizing the PDMS surface and providing an amine group for glutaraldehyde bonding. Samples were baked at 80° C. for 30 minutes to promote condensation and siloxane bond formation. 3) APTES modified PDMS are coated with 1% glutaraldehyde solution for the generation of aldehyde group required for PVA bonding. 4) Glutaraldehyde functionalized surface allows covalent bonding between the PVA coat and the PDMS.
Figure 4:
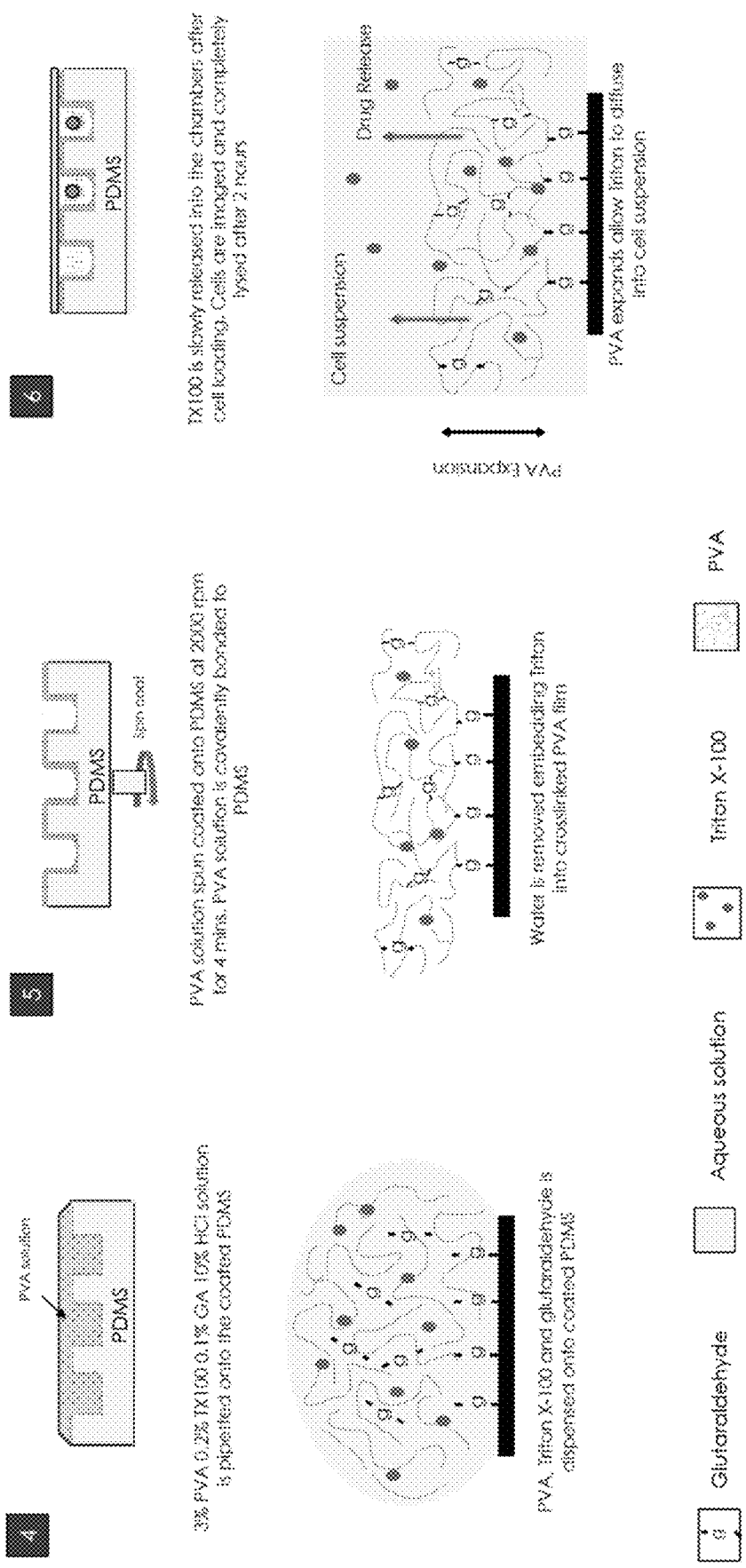
FIG. 4 is a schematic diagram depicting an example of controlled release chemistry and a preparation for single cell lysis according to the methods of the disclosure. 4) Coating solution (PVA, Triton X-100, HCl and free glutaraldehyde) is pipetted onto glutaraldehyde functionalized surface initiating PVA hydrogel formation on the PDMS surface. 5) Liquid is removed via spin coating leaving a thin PVA film across the surface of the PDMS. The now cross linked PVA film is covalently bonded to the PDMS surface immobilizing the triton with the film. 6) Cells are loaded into the coated PDMS chambers and enclosed with the surface comprising the repeating pattern of capture agents (which, in this example, are antibodies). Liquid in the cell suspension diffuses into the hydrogel causing it to expand and slowly release the Triton X-100 into the microchambers, lysing the cells within 30 minutes.
Figure 7:
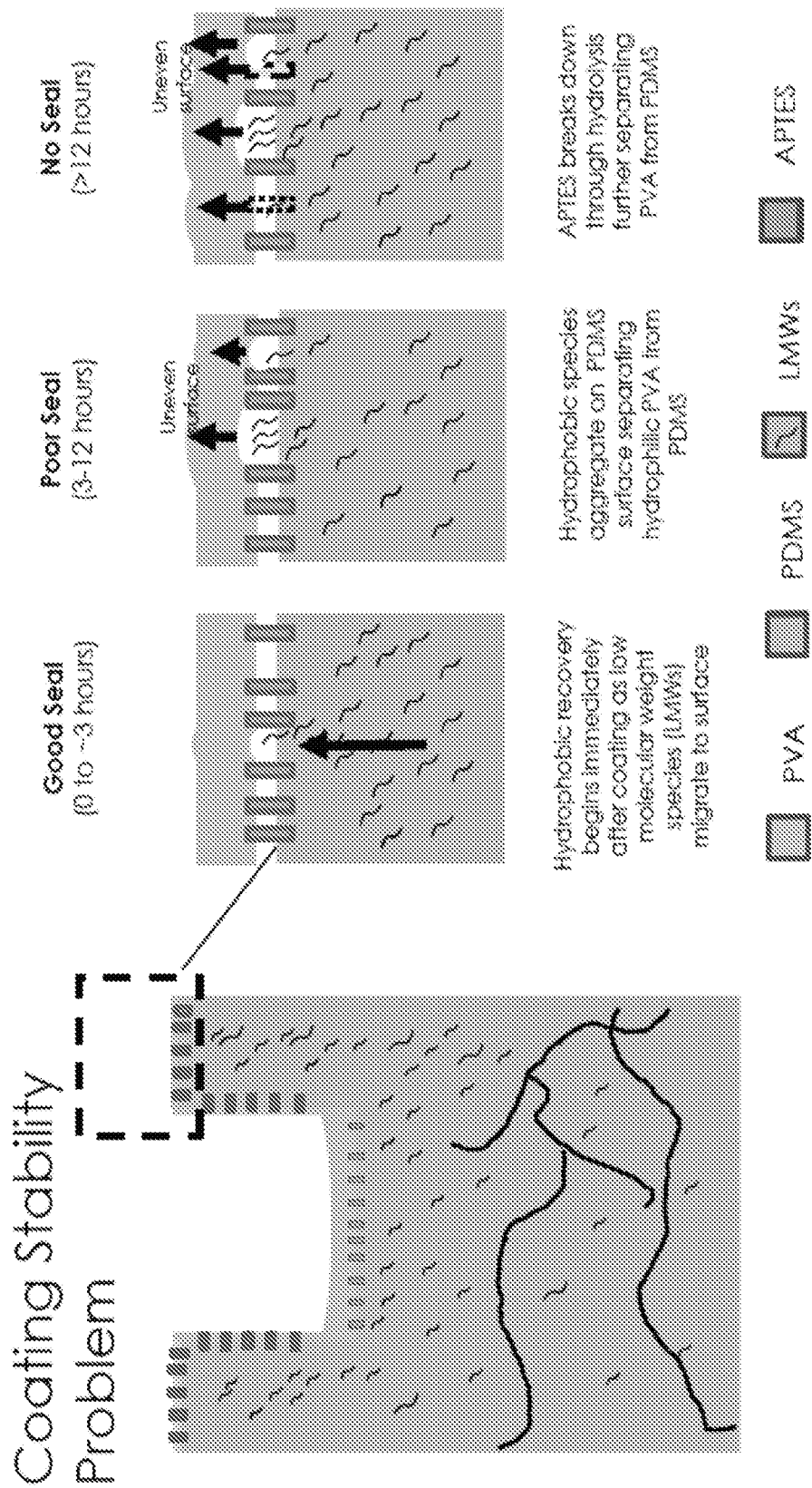
FIG. 7 is a series of schematic diagrams depicting development of a coating composition of the disclosure. Although separation of a hydrophilic crosslinking composition (PVA, for example) from the PDMS-based substrate is desirable for controlled lysis composition and/or signaling agent release, the linker composition, including the functionalization component of the linker composition (in this example, APTES) may be optimized to resist hydrolysis when the coating composition or the intended cell composition is aqueous (contains water). Although APTES provides an adequate seal in this example, the disclosure provides a linker composition, including the functionalization component of the linker composition that will not undergo hydrolysis under these conditions.
Figure 8:
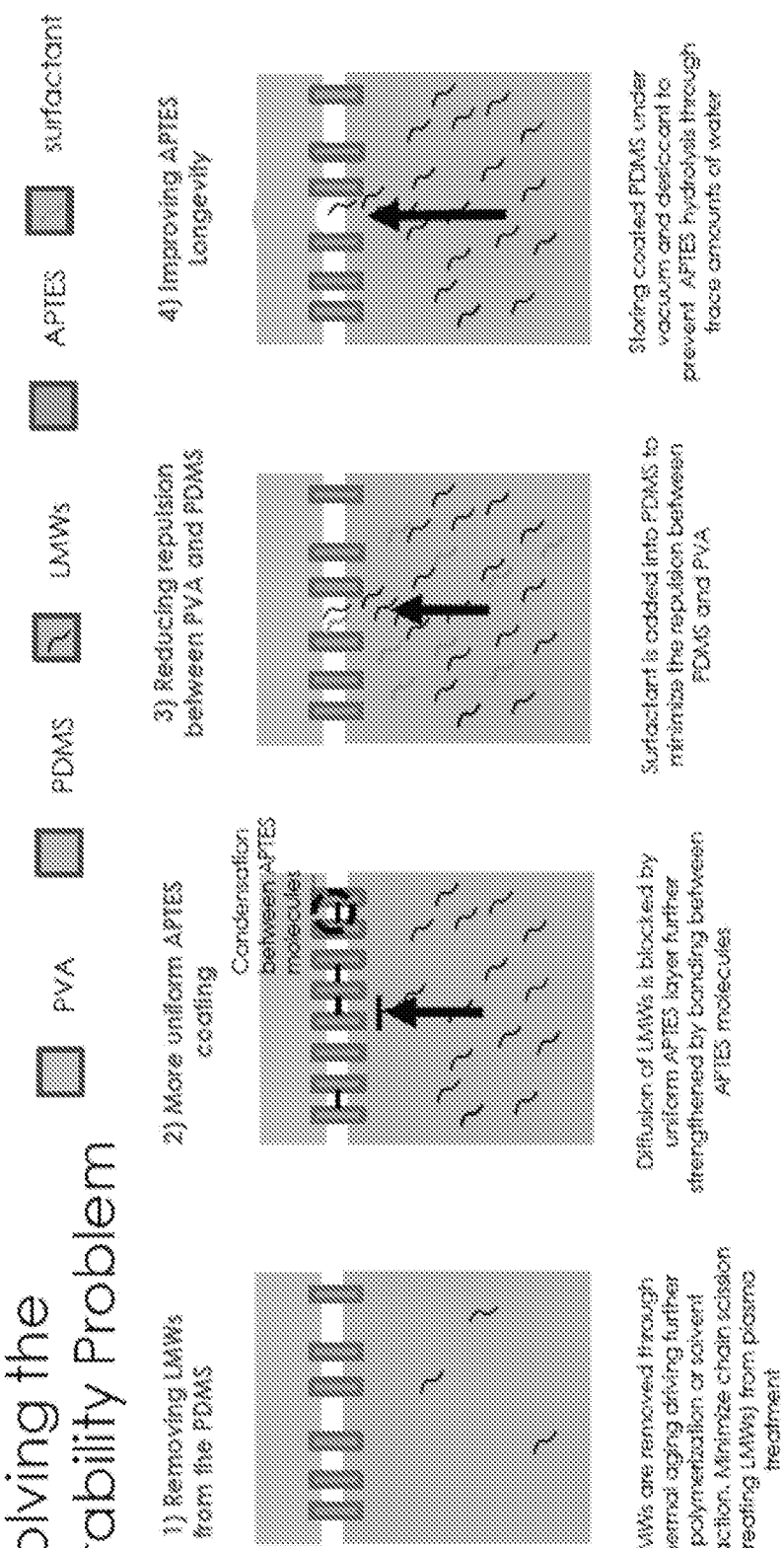
FIG. 8 is a series of schematic diagrams depicting development of a coating composition of the disclosure. In addition to optimizing the linker composition, including the functionalization component of the linker composition to resist hydrolysis in the presence of water, this series of diagrams show alternative methods for increasing stability of the linker composition over longer periods of time. Alternative methods, shown include, but are not limited to, removing low molecular weight (LMW) species from the PDMS substrate, introducing bonds between molecules of the functionalization component (in this example, APTES) to minimize diffusion of LMW species and generate a more uniform coating, adding a surfactant to the PDMS substrate to reduce repulsion between the crosslinking composition and the PDMS substrate, and storing the substrate comprising the coating composition under a vacuum with a desiccant to minimize or prevent degradation of the functionalization component (in this example, hydrolysis of APTES) by trace amounts of water.
Figure 9:
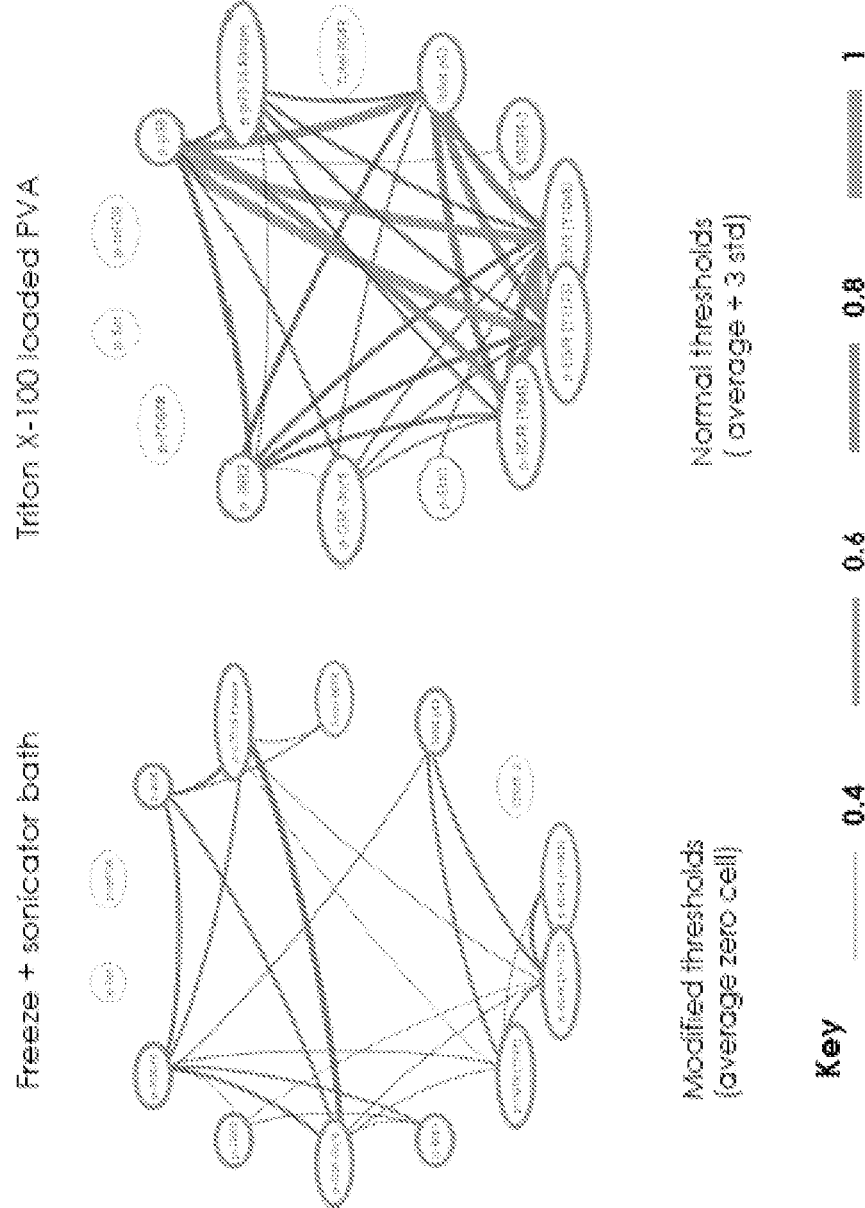
FIG. 9 is a pair of schematic diagrams comparing the signal coordination between a substrate using a combination of freezing and sonication to apply the coating composition to the substrate and a substrate comprising a coating composition including Triton-X-100 loaded PVA. As shown in the diagram, the signal coordination using the substrate comprising a coating composition including Triton-X-100 loaded PVA (the controlled release method) is superior to the alternative.
Figure 11:
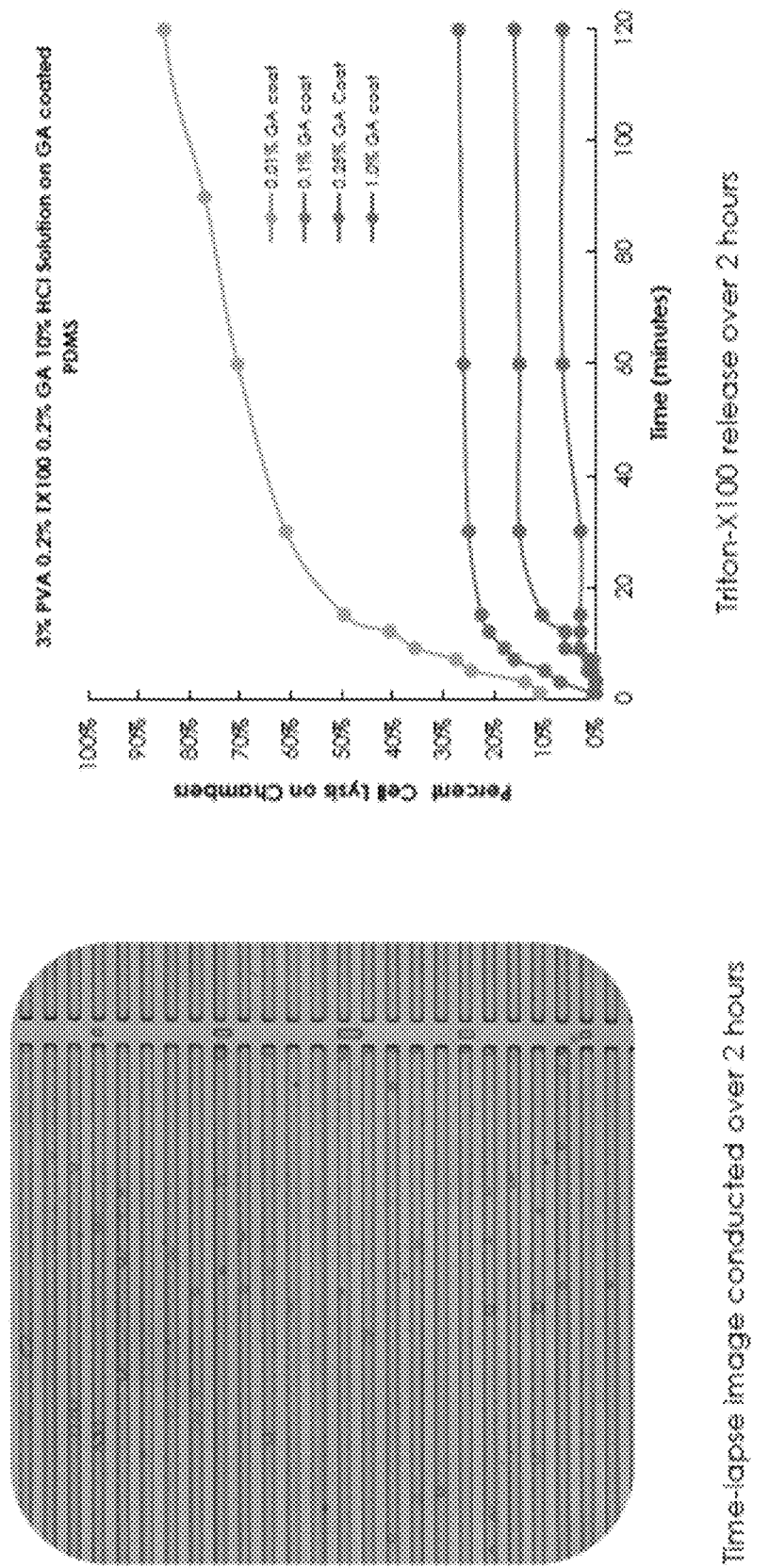
FIG. 11 is a photograph and graph depicting the optimization of the lysis composition. The left panel is a still photograph of time lapse photography performed over a period of two hours for visual confirmation of cell lysis. The right panel is a graph showing the quantitative analysis of this data for a coating composition comprising 3% PVA, 0.2% Triton-X-100, 0.2% Glutaraldehyde, and 10% HCl applied to a PDMS substrate pre-coated with Glutaraldehyde. The top line (0.1% Glutaraldehyde coat) on the PDMS substrate performed better than the (0.1% GA coat, next line down, blue; 0.25% GA coat, second line down, purple; and 1.0% GA coat, bottom line, red). While all concentrations of glutaraldehyde induced cell lysis, the 0.1% Glutaraldehyde pre-coat on the PDMS substrate performed the best.
Figure 14:
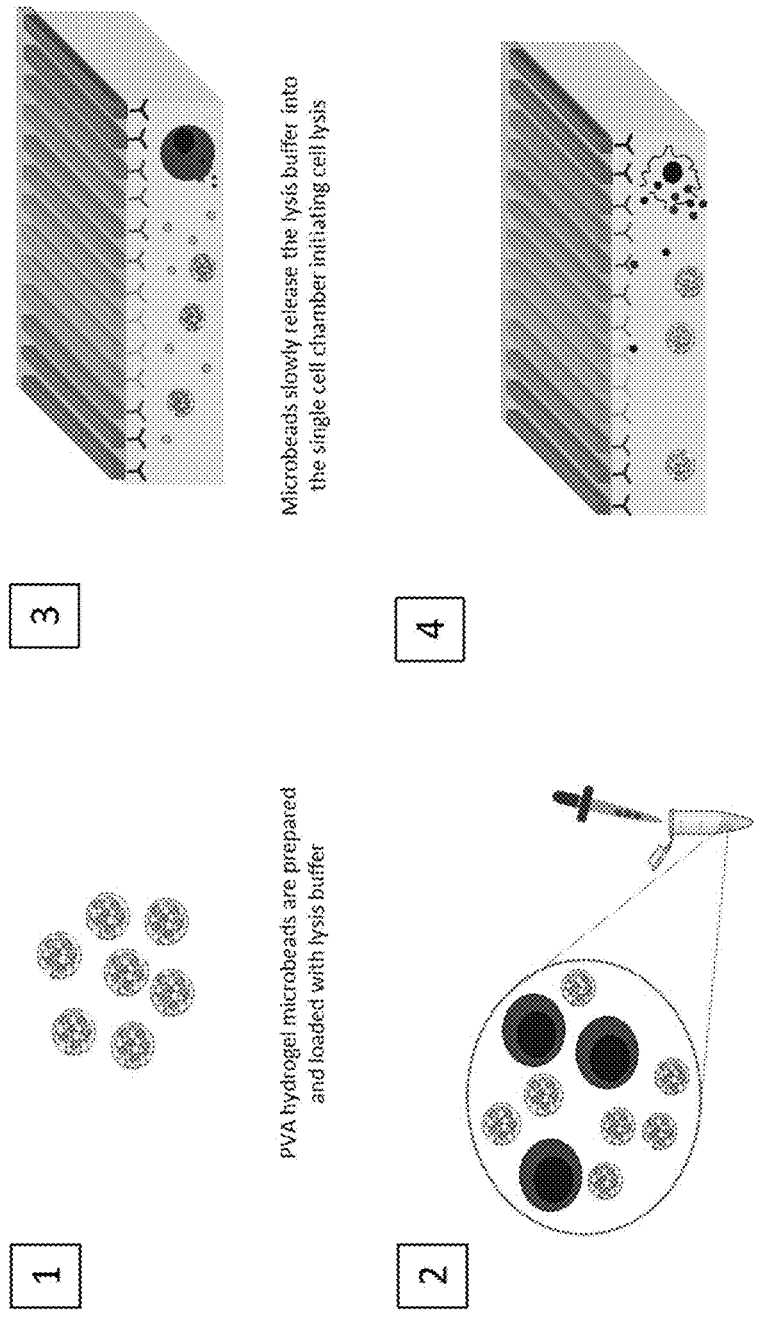
FIG. 14 is a series of schematic diagrams depicting an exemplary process for the preparation of a coating composition of the disclosure. In step 1, a lysis composition and a crosslinking composition are combined to form a plurality of microbeads. In this particular example, the crosslinking composition comprises PVA. In step 2, the coating composition and a cell suspension (comprising dissociated single cells) are combined. An aliquot of the composition from step 2 comprising a single cell and a plurality of microbeads is introduced into at least one chamber of the substrate (and preferably, this step is repeated until each chamber contains a single cell and a plurality of microbeads. Once the composition of step 2 has been distributed among the chambers of the substrate, the surface that releasably couples to the substrate is contacted to the substrate. In step 3, the microbeads release the lysis composition in a controlled manner into the chamber, initiating lysis of the single cell in the same chamber. In step 4, the microbeads have released most of the lysis composition and cell lysis is complete. The intracellular components of the single cell in the chamber are released into the surrounding liquid where these components encounter and specifically bind to the capture agents of the surface.
Figure 15:
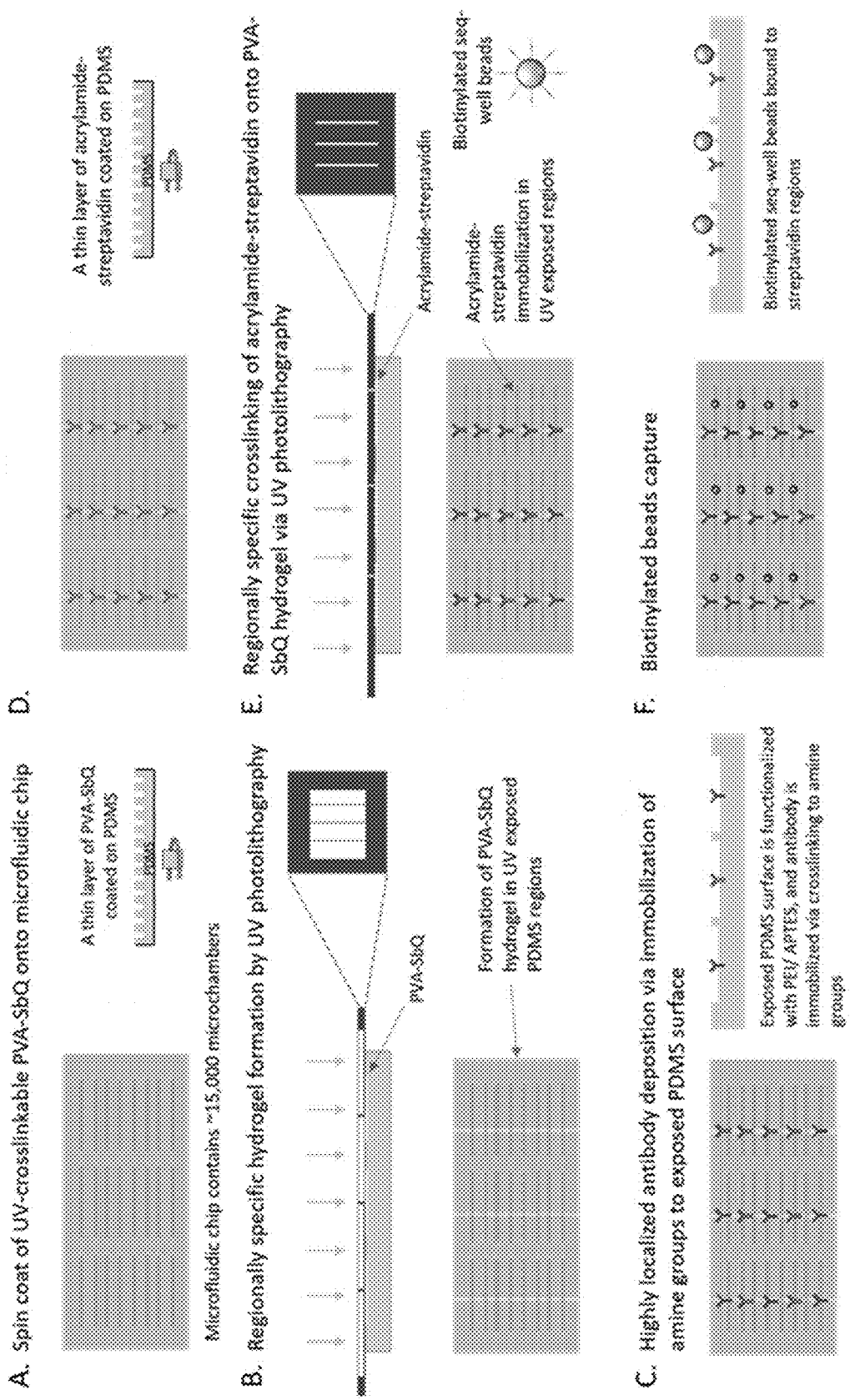
FIG. 15A-L is a series of schematic drawings depicting a sequencing protocol for single bead, single cell capture. A. UV crosslinkable PVA is spin-coated onto the microchamber surface. B. Using a negative photomask, PVA is crosslinked forming a PVA hydrogel on microchamber surface with exception of 10 μM bands not exposed to UV light. C. Exposed PDMS is functionalized with amine groups/glutaraldehyde for antibody immobilization D. Acrylamide-streptavidin is spin-coated onto the surface and E. immobilized into band utilizing a positive photomask. F. Biotinylated seq-well beads are bound to streptavidin functionalized surface. Final consumable consists of 1 bead and 1 cell per microchamber. G. Hydrogel coated PDMS microchambers are soaked in 3% SDS for an hour. During this time, the lysis agent, SDS, is absorbed by the hydrogel. After incubation, microchambers are rinsed with dH$_2$O and then dried with compressed air. H. Cells are resuspended at the appropriate concentration in an RNAse inhibitor solution, and pipetted on to the surface of the microchamber PDMS. The cells are allowed to bind to the capture antibody before excess cells are washed off. I. Once cells are loaded, the microchamber is sealed by the addition of an antibody glass slide and SDS is slowly released from the hydrogel. J. After lysis, the mRNA transcripts hybridize to the poly-T region of the oligos on the capture beads. K. After incubation, the microchamber PDMS is unsealed and the beads are washed off of the microchambers. The beads are collected in a flacon tube and washed before further processing. L. A cDNA library is generated from the beads via template switching-PCR. The cDNA library is then amplified and indexed for NGS.
Figure 15:
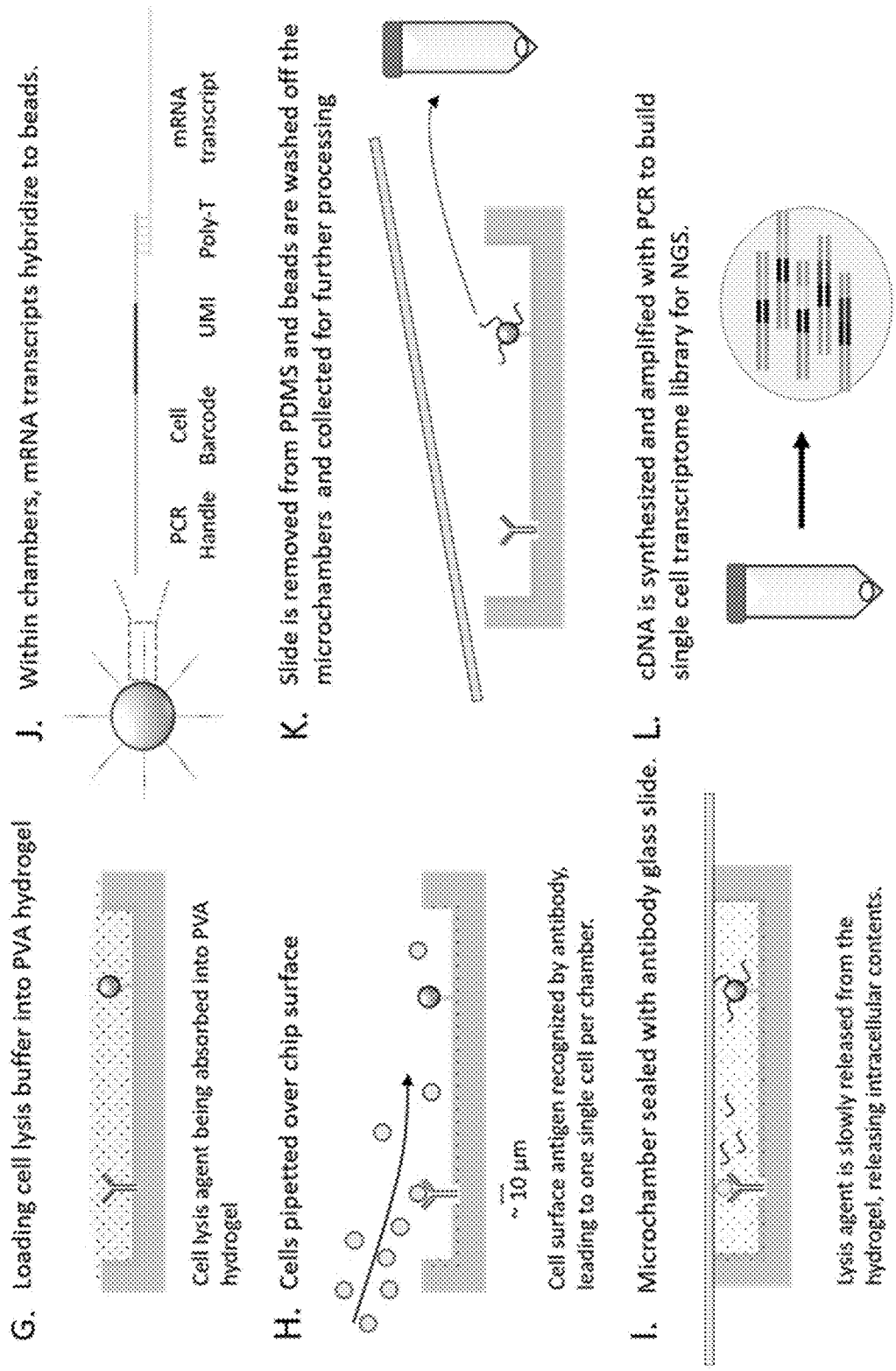
Figure 16:
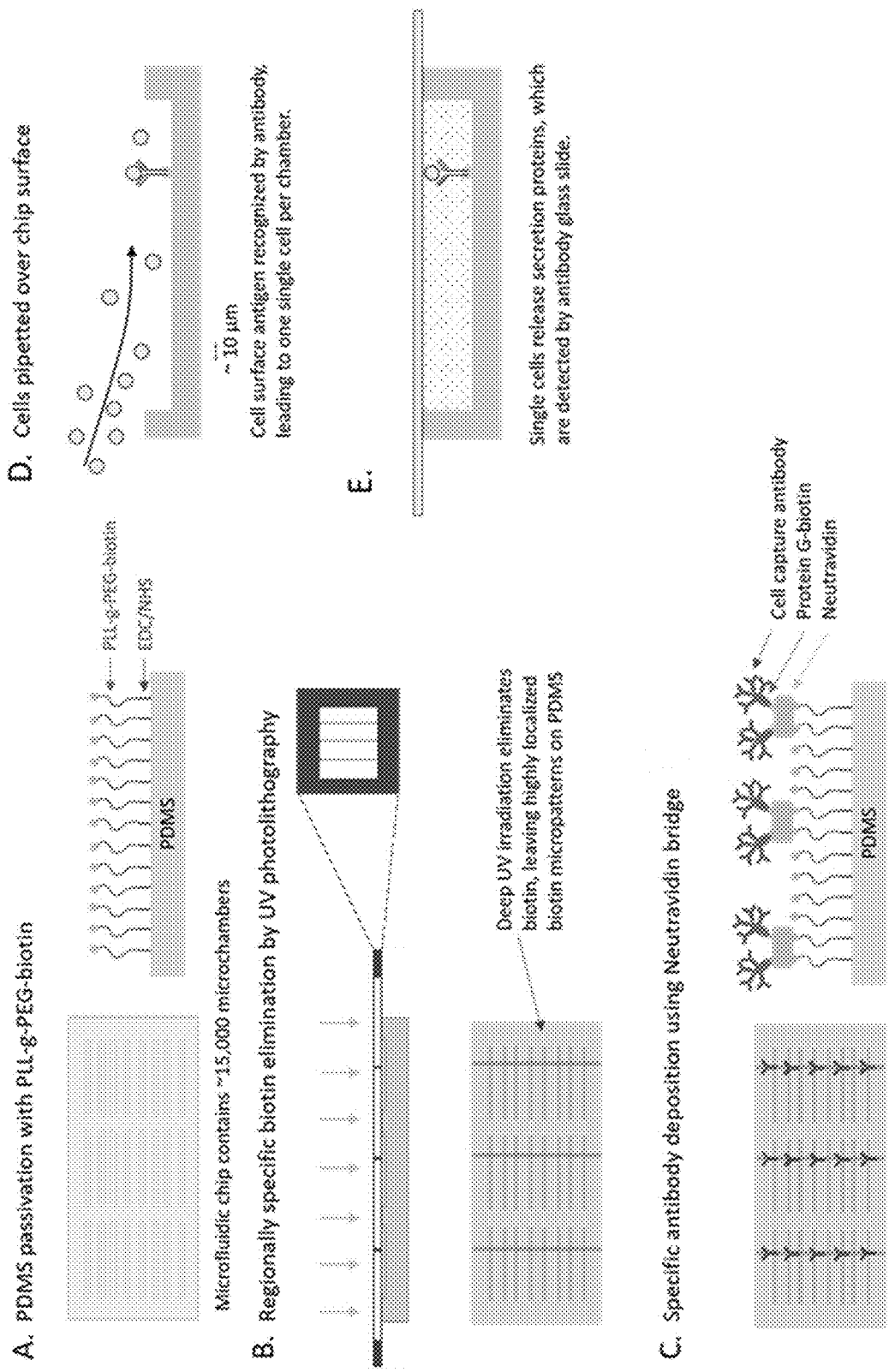
FIG. 16A-E is a series of schematic drawings depicting single-cell capture. A. PLL-g-biotin is spin-coated onto the microchamber surface after PDMS treatment with ECD/NHS. B. Using a negative photomask, PLL-g-PEG-biotin is removed from PDMS surface except for 10 µM bands not exposed to UV light. C. Biotinylated region is functionalized with cell capture antibody via neutravidin/protein-G-biotin D. Cell suspension is pipetted onto PDMS surface, single cells are captured by antibody band in each microchamber and excess cells are rinsed off the microchambers E. Microchambers are sealed with an antibody slide and incubated for 16 hours to capture secreted cytokines.
Figure 18:
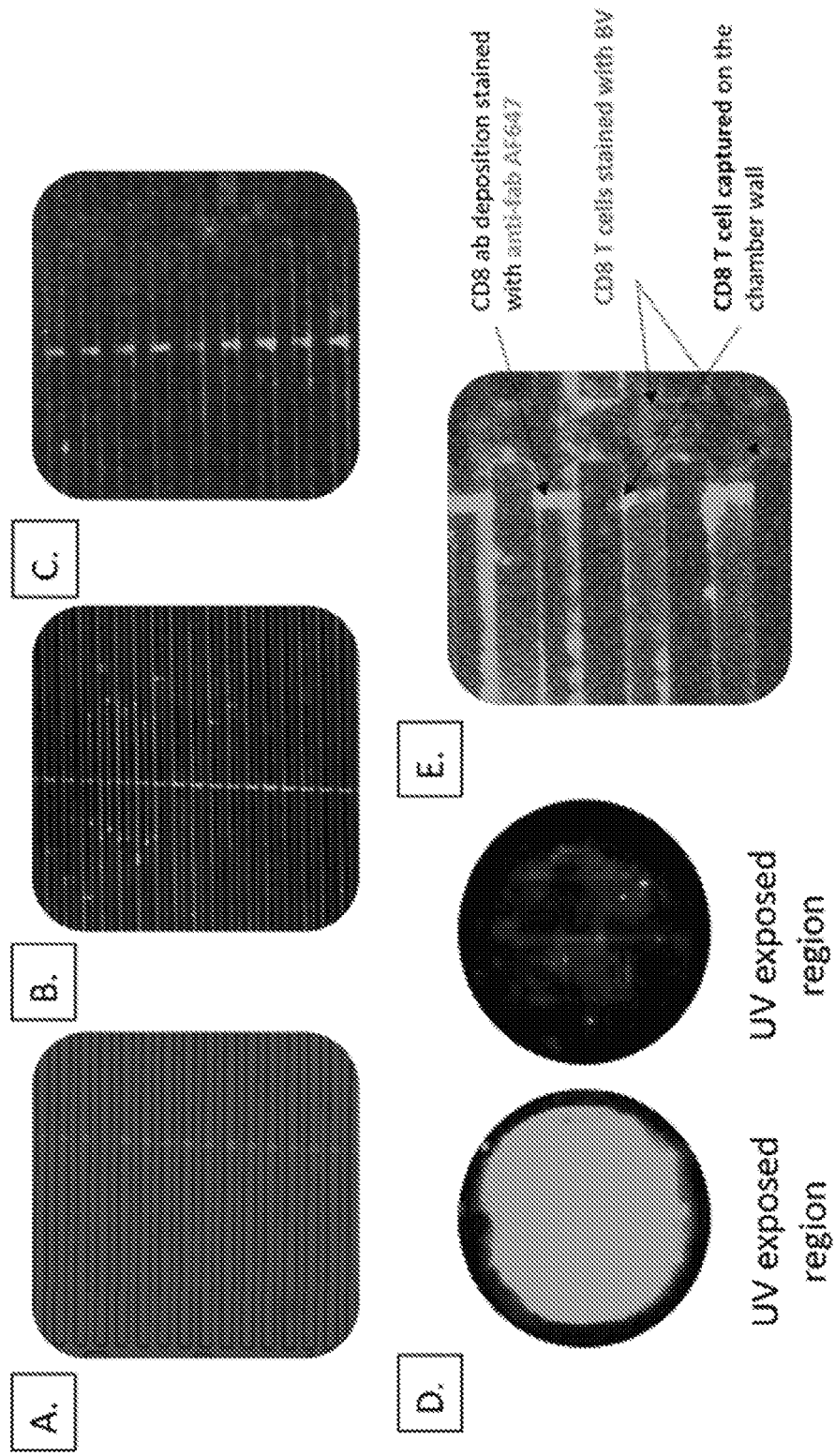
FIG. 18A-E is a series of photographs depicting photolithography development and antibody immobilization chemistry. A. Positive mask photolithography: PDMS microchambers are coated with PLL-g-PEG. Utilizing contact photolithography, PLL-g-PEG is degraded by UV lithography, leaving a discrete band within chambers visualized by FITC-BSA. B. Negative mask photolithography. PDMS microchambers are coated with PLL-g-PEG-biotin. Utilizing contact photolithography, PLL-g-PEG-biotin is degraded by UV lithography, leaving a discrete biotin band within chambers visualized by streptavidin-Alexa Fluor 647 C. Selective antibody deposition. CD8 Antibody band successfully deposited on PDMS surface microchambers (validated with anti-fab Alexa Fluor 647). D. Binding Chemistry. Selective CD8a antibody deposition on non-UV exposed (left) and UV exposed regions (right). E. 5× Microscope image of single CD8+ T cells, stained with a brilliant violet membrane stain, trapped by anti-CD8a antibody bands.
Figure 19:
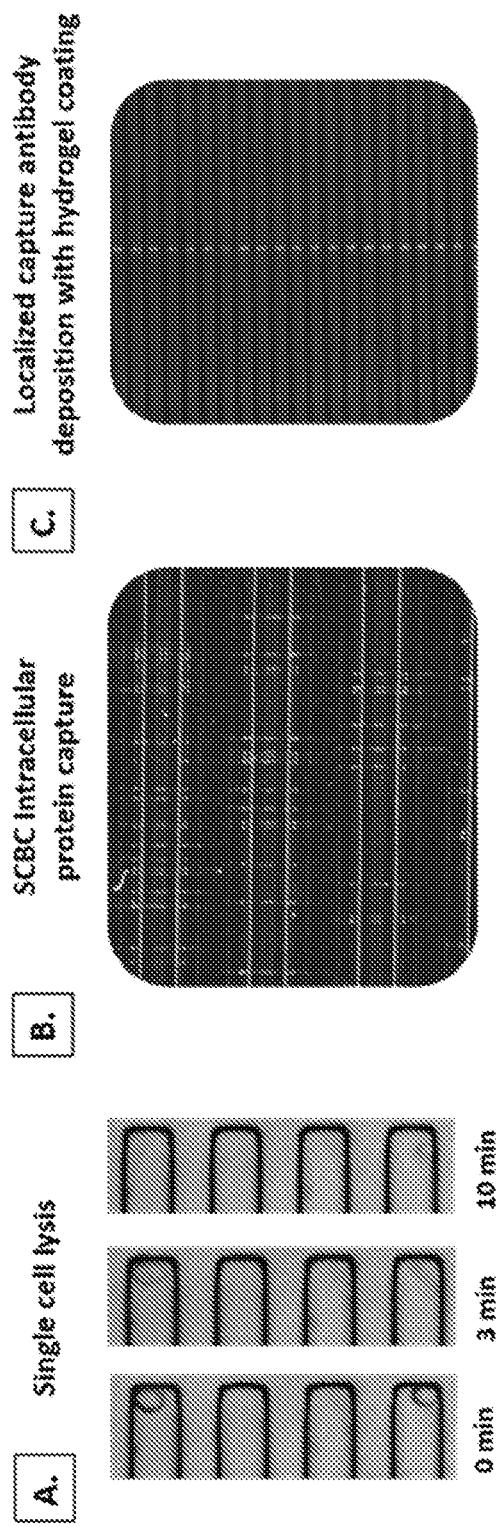
FIG. 19A-C is a series of photographs depicting validation of photo-cross-linkable polymer (SbQ-PVA) optimized for single cell lysis and surface functionalization. A. A thin PVA hydrogel coat was UV crosslinked to the surface of the PDMS microchambers and loaded with lysis buffer. Cells were stained with a brilliant violet cell stain and loaded onto the microchamber PDMS. 5× time lapse images were taken demonstrating that complete cell lysis was achieved after 10 minutes. B. The hydrogel coated microchambers were tested through the simultaneous protein and sequencing capture composition protocol and enabled successful capture of intracellular phosphoproteins. C. UV curable hydrogel enabled region specific antibody deposition by utilizing a negative photomask. Exposed PDMS regions (not covered by hydrogel) were functionalized with anit-CD8a antibody bound by the (3-aminopropyl)triethoxysilane (APTFS)/glutaraldehyde PDMS surface modification.
Figure 20:
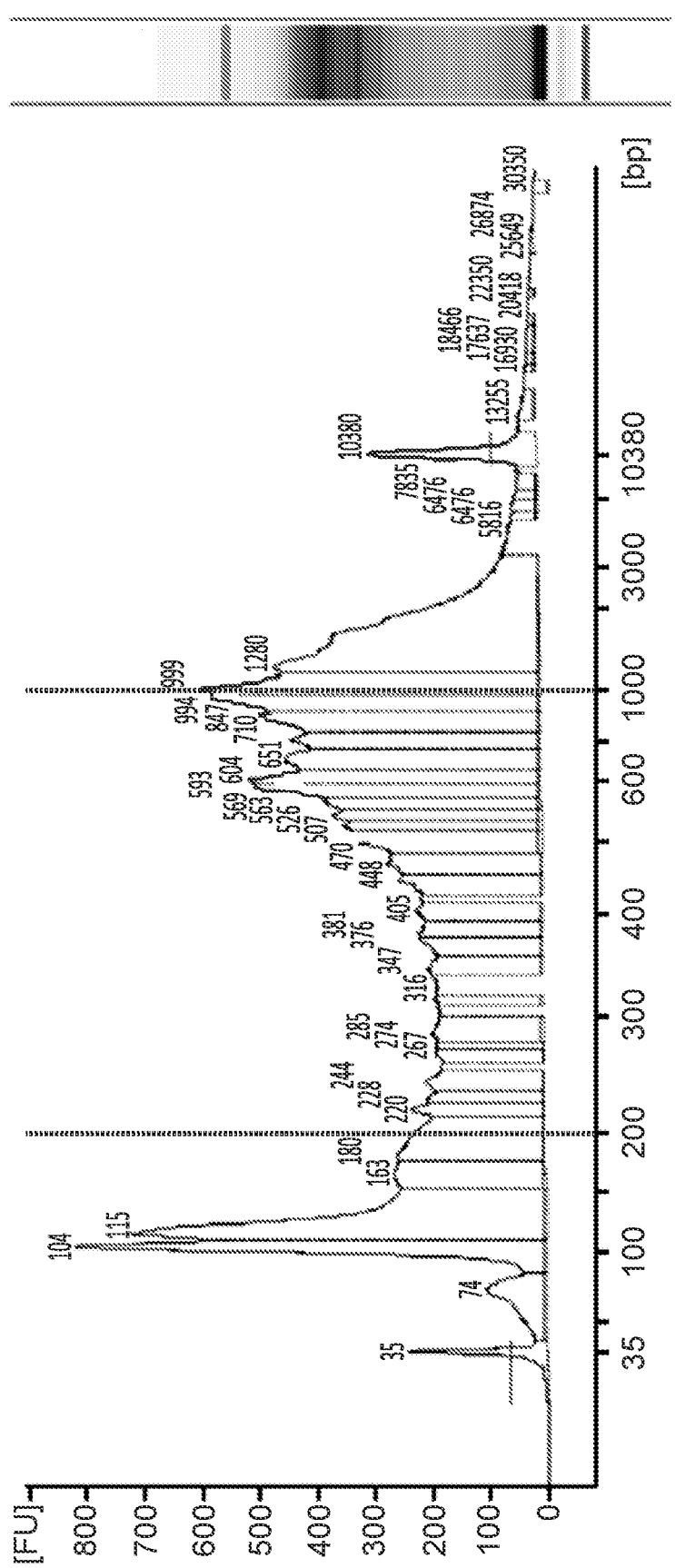
FIG. 20 is a graph of bioanalyzer data showing cDNA library smear with a majority of fragments between 200 and 1000 bp. The data demonstrate the ability of the compositions and methods of the disclosure to i) bind RNA from lysed cells to beads on chip, ii) effectively recover beads from chip, and iii) process recovered beads in a manner to effectively produce a single-cell cDNA library for sequencing.
Figure 21:
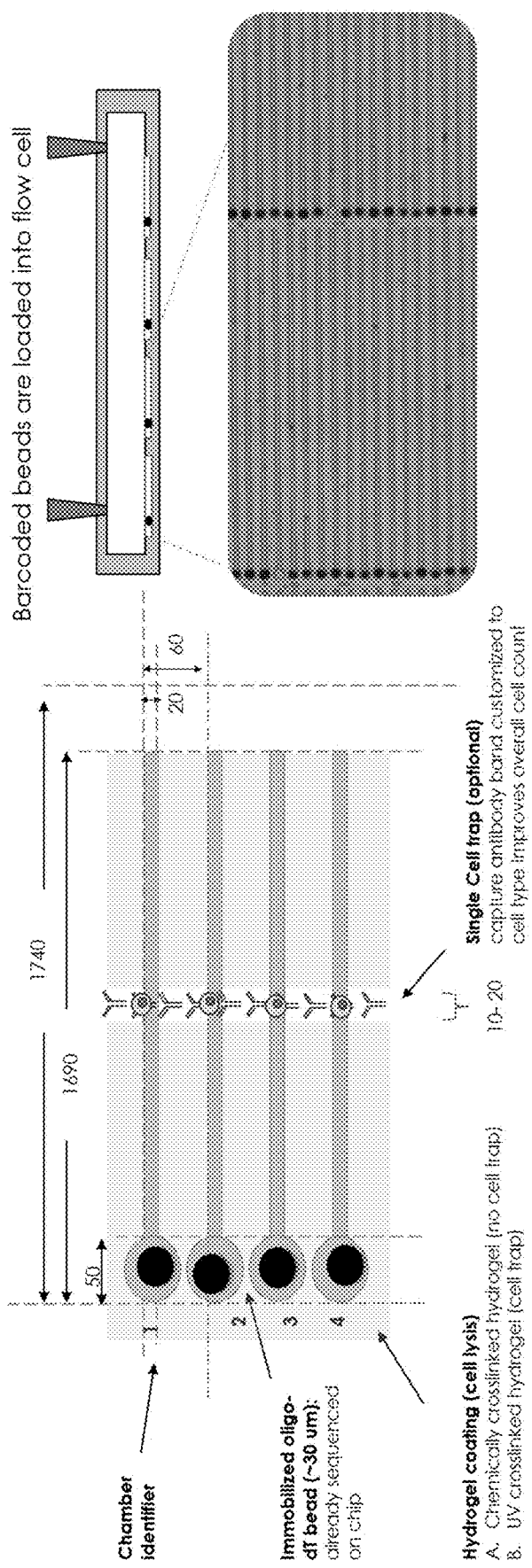
FIG. 21 is a series of schematic diagrams depicting an exemplary proteomic/transcriptomic consumable device of the disclosure. In this embodiment, beads are captured in size specific wells at the end of each microchamber allowing for only one oligo-dT bead per chamber. Surface is coated with hydrogel for controlled lysis buffer release for single cell lysis. Single cell trap can also be incorporated to locate cell capture closer to bead.
Figure 22:
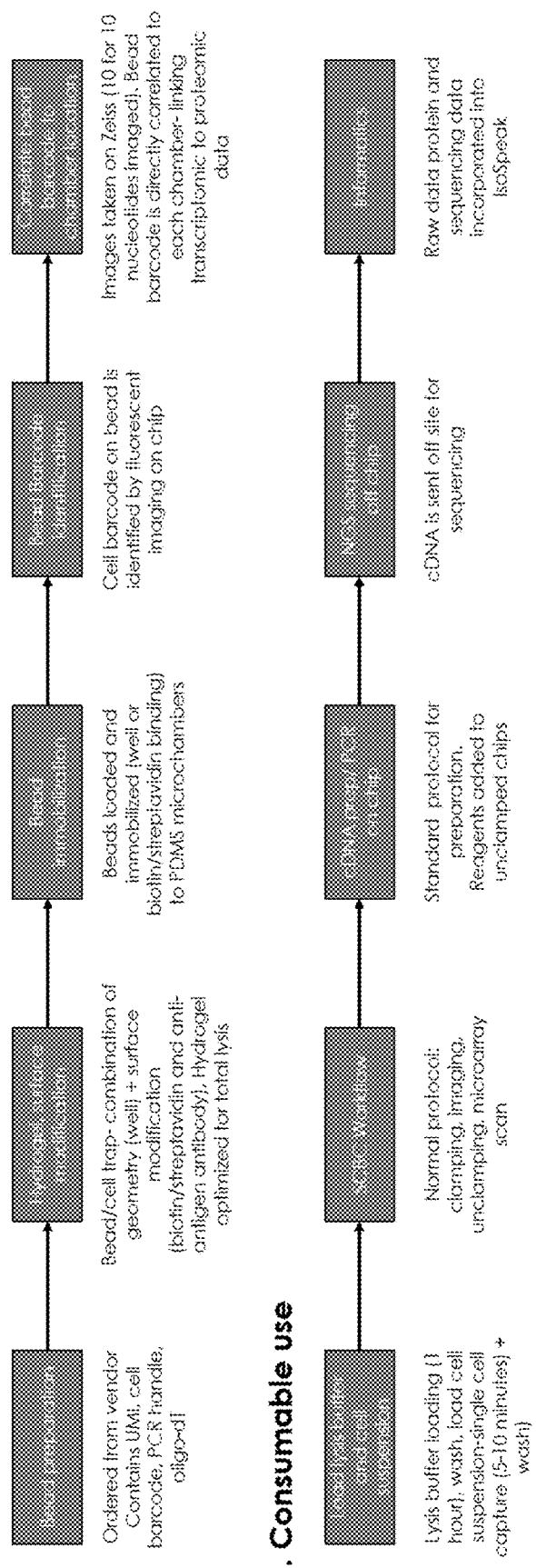
FIG. 22A-B is a pair of schematic diagrams depicting an exemplary full sequencing protocol for consumable preparation (A) and consumable use (B). To summarize, oligo-dT beads are captured and immobilized onto PDMS microchambers. Bead barcode is identified on chip with fluorescently microscopy linking the microchamber (for single cell and protein capture) with the oligo-dT beads (for mRNA capture and downstream sequencing). Microchambers are coated with a drug loaded hydrogel that enables single cell lysis. For the general workflow, cells are loaded onto sequencing consumable and sealed into microchambers with barcode identified beads. Cells are lysed, and mRNA and proteins are captured. Consumable is unsealed where beads are extracted for off chip sequencing and protein data is analyzed using standard ELISA protocol. Final data transcriptomic and proteomic data is linked with an analysis program that is able to bin the single-cell data, for both the transcriptomic information and data points, and in addition, the proteomic information and data points, for simultaneous analysis of DNA, RNA, and proteome from individual cells.
Figure 23:
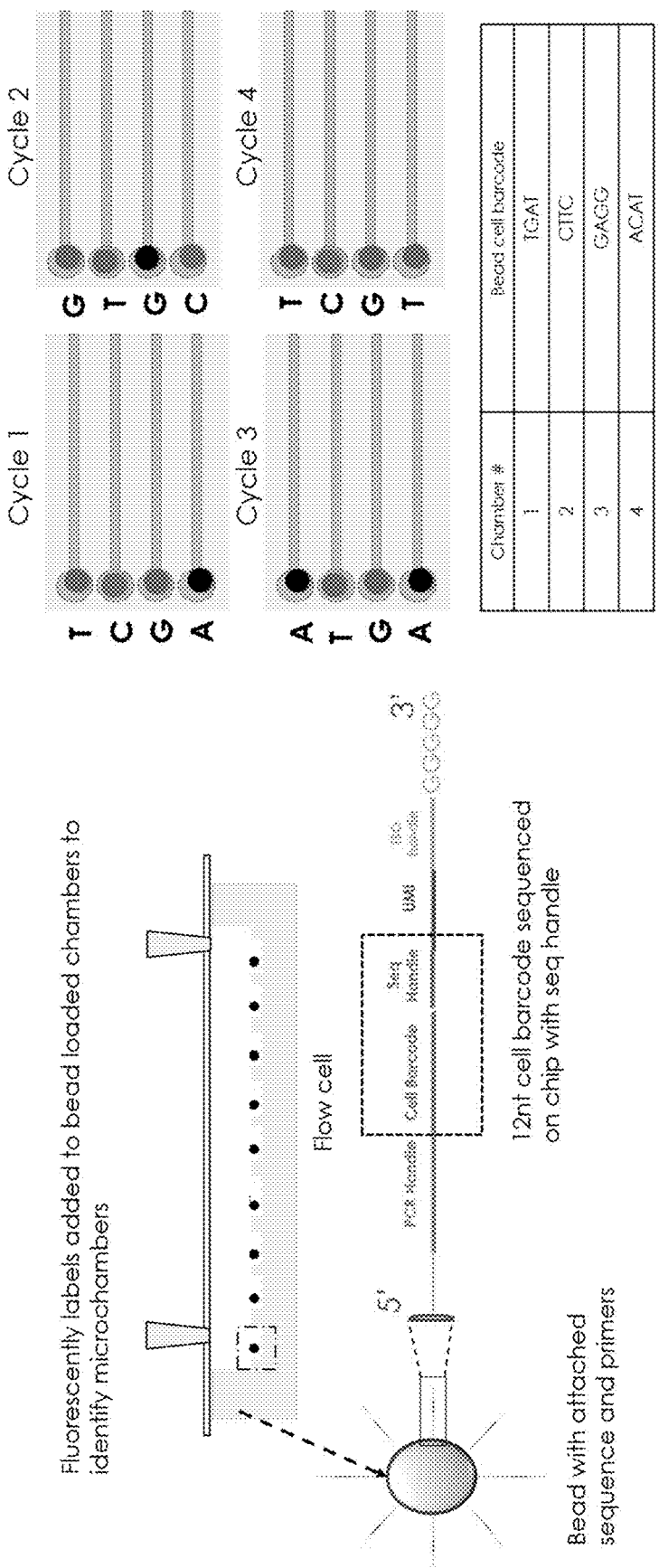
FIG. 23 is a series of schematic diagrams depicting an exemplary embodiment of an on chip sequencing process. Sequence handle is added to oligo-dT beads to allow for cell barcode identification. Beads are loaded into microchamber. Cell barcode is sequenced on chip with fluorescent labels linking the bead cell barcode to a specific chamber.
Figure 24:
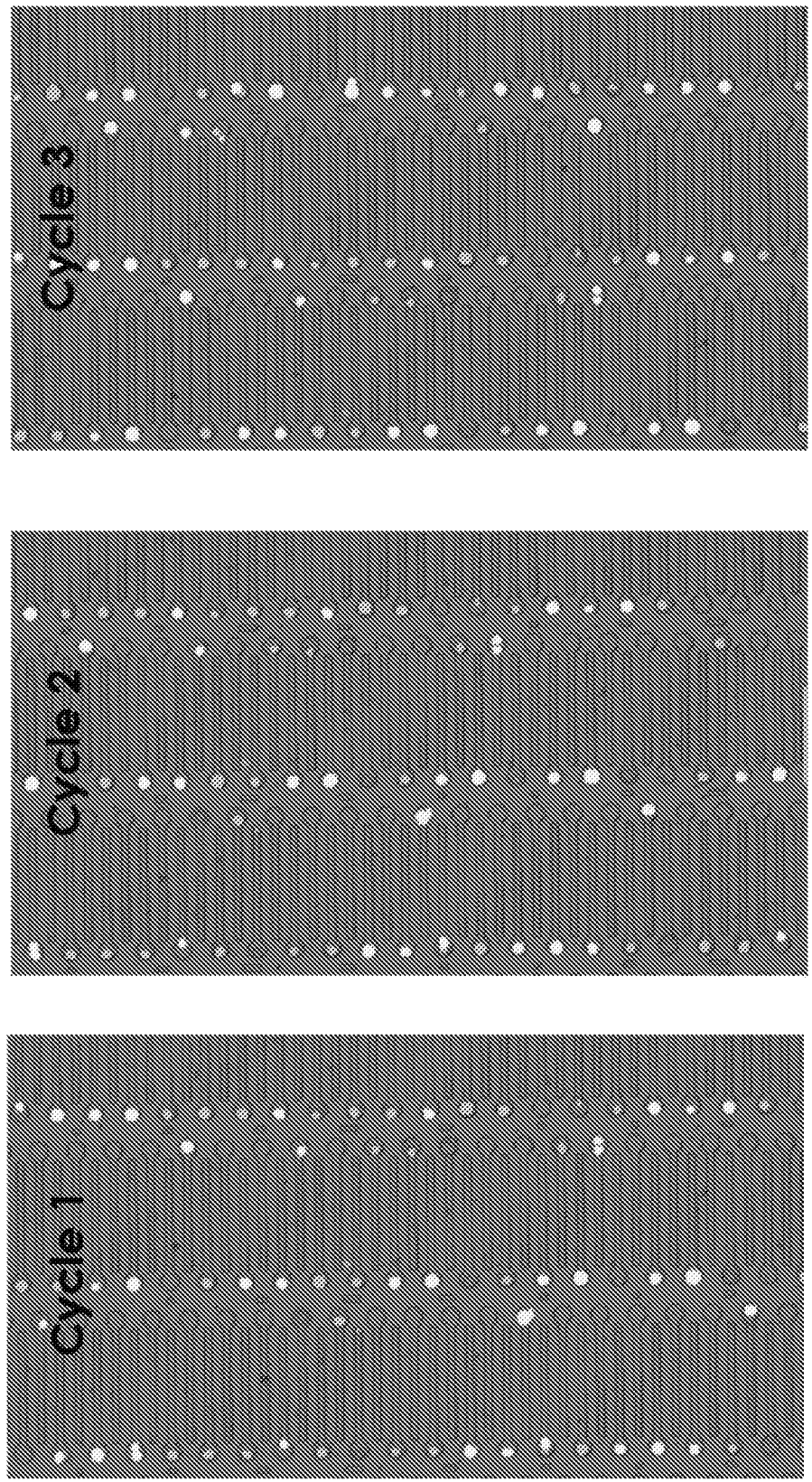
FIG. 24 is a series of exemplary raw images for use in a process of bead identification. AF568 and AF647 labeled tags are flowed to identify T and G nucleotides of cell barcode sequence.
Figure 25:
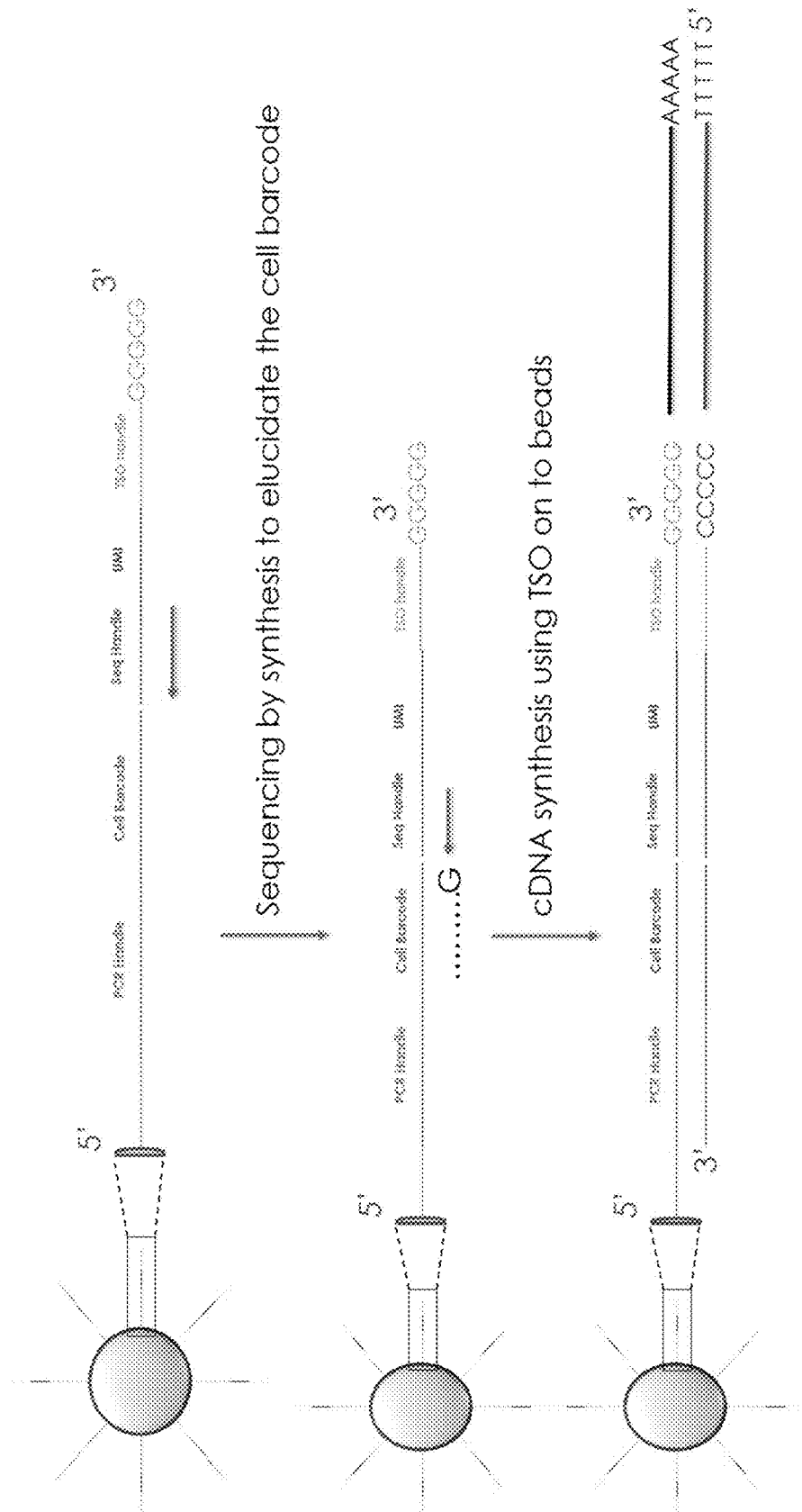
FIG. 25 is a series of schematic diagrams depicting exemplary embodiments of bead chemistry and mRNA capture. Cell barcode is sequenced from sequencing handle for on chip bead identification. Primer and fluorescent labels are removed from oligo-dT beads. cDNA is synthesized from mRNA in the well and captured using template switching oligo on beads.
Figure 26:
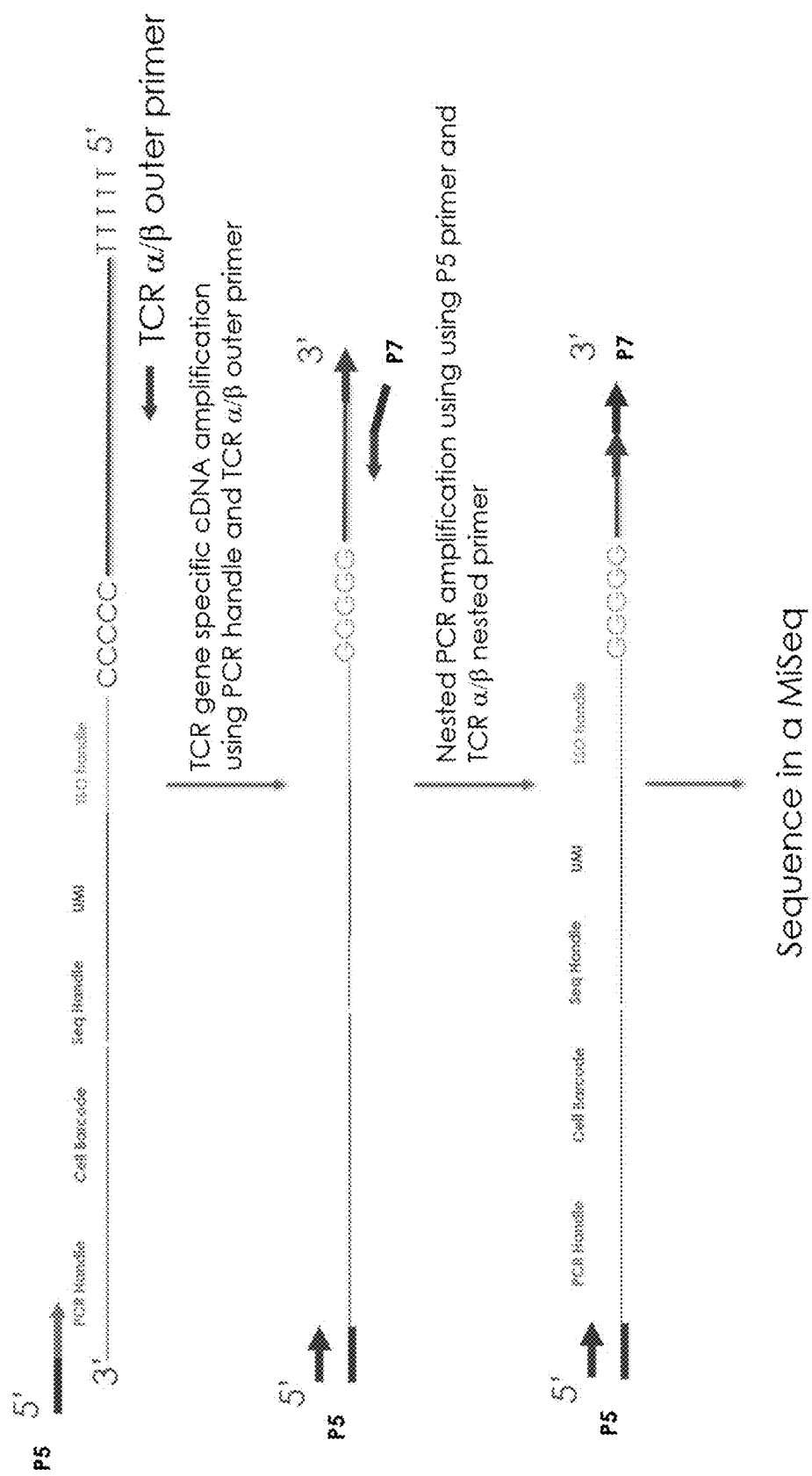
FIG. 26 is a series of schematic diagrams depicting exemplary embodiments of TCR-specific amplification. cDNA captured by oligo-dT beads is selectively amplified using TCR specific primers. Final library is sent to MiSeq for sequencing.
Figure 27:
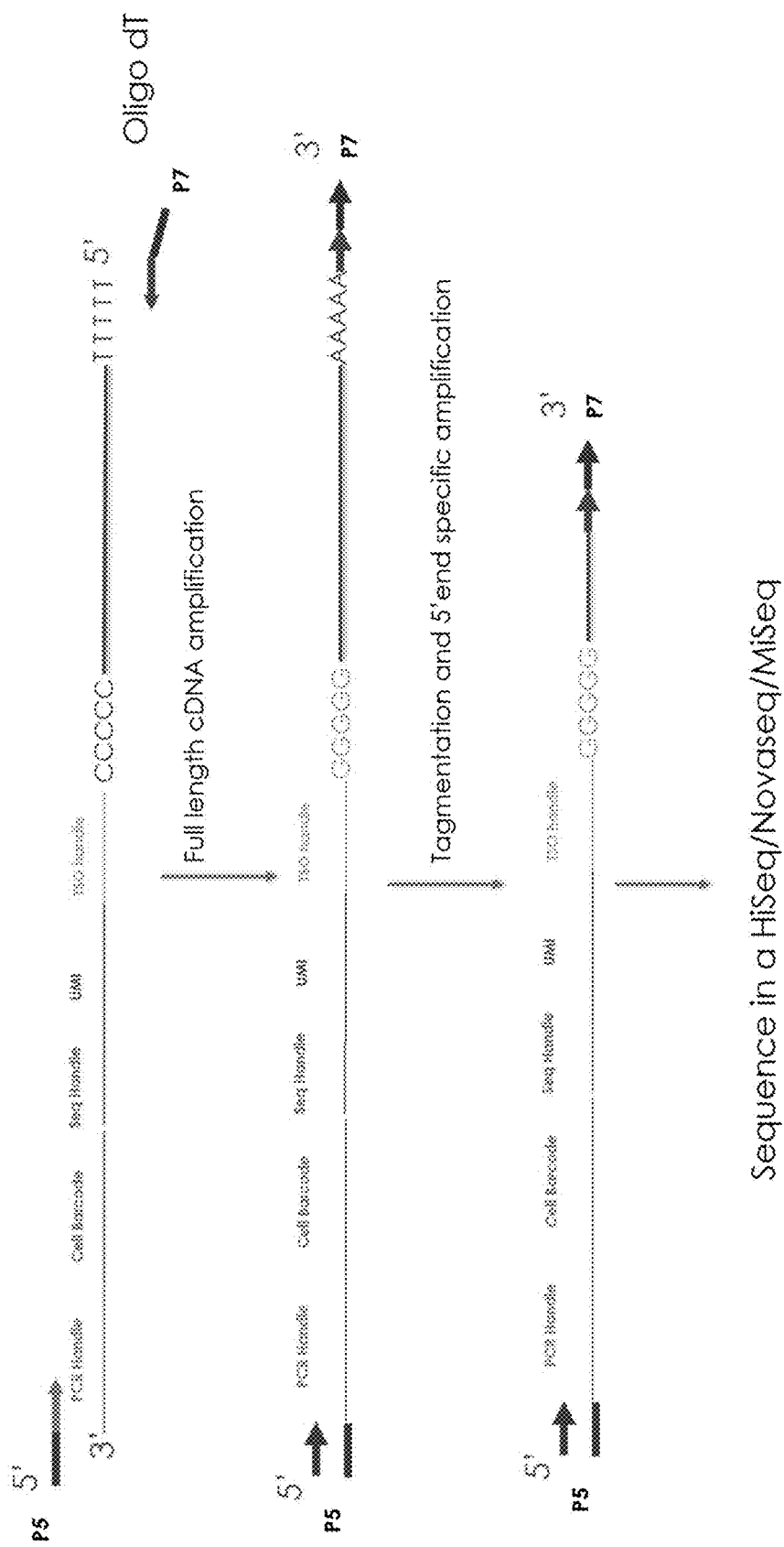
FIG. 27 is a series of schematic diagrams depicting exemplary embodiments of Tag-counting from amplified cDNA. Full length cDNA is amplified for Tag-counting. Final library is sequenced using a HiSeq, NovaSeq or MiSeq.

The coating compositions of the disclosure incorporate a controlled lysis composition and/or signaling agent release technology. The chambers comprise a coating composition that comprises a lysis composition and, optionally, includes a crosslinking composition. The chambers comprise a coating composition that comprises a lysis composition a signaling agent and, optionally, includes at least one crosslinking composition. In certain embodiments the compositions of the disclosure, the crosslinking composition comprises a biocompatible polymer such as PVA (poly (vinyl alcohol). For example, the biocompatible polymer such as PVA may be loaded with the lysis composition (for example, a composition comprising Triton X-100). Upon introducing a desired cell composition (which is preferably a cell suspension) into a chamber of the composition, the crosslinking agent (for example, PVA) contacts a fluid of the cell composition and expands to release the lysis composition into the chambers in a controlled manner (see, FIG. 2B).

The crosslinking composition may be optimized for a controlled release of the lysis composition over a defined period of time. For example, the crosslinking composition may be optimized for a controlled release of the lysis composition over a period of time of at least 1 second, 2 seconds, 3 seconds, 4 seconds, 5 seconds, 6 seconds, 7 seconds, 8 seconds, 9 seconds, 10 seconds, 15 seconds, 20 seconds, 25 seconds, 30 seconds, 35 seconds, 40 seconds, 45 seconds, 50 seconds, 55 seconds, 60 seconds or any number of seconds in between. The crosslinking composition may be optimized for a controlled release of the lysis composition over a period of time of at least 1 minute, 2 minutes, 3 minutes, 4 minutes, 5 minutes, 6 minutes, 7 minutes, 8 minutes, 9 minutes, 10 minutes, 15 minutes, 20 minutes, 25 minutes, 30 minutes, 35 minutes, 40 minutes, 45 minutes, 50 minutes, 55 minutes, 60 minutes or any number of minutes in between. The crosslinking composition may be optimized for a controlled release of the lysis composition over a period of time of at least 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours or any increment of an hour in between.

The crosslinking composition may be optimized for a controlled release of the lysis composition by varying identify and/or concentration of one or more components of the crosslinking composition. For example, a crosslinking composition and/or biocompatible polymer may comprise any monomer unit and may comprise any number of monomers (any molecular weight of the polymer). A crosslinking composition and/or biocompatible polymer may comprise any concentration of polymer molecules. A crosslinking composition and/or biocompatible polymer may crosslink to varying digress forming an either loose matrix or a dense matrix that may increase or decrease escape of a lysis composition from the crosslinking composition, respectively.

The crosslinking composition may be optimized for a controlled release of the lysis composition by varying a mechanism of release of the lysis composition. For example, a crosslinking composition and/or biocompatible polymer may degrade in the presence of a cell composition but not degrade in the absence of a cell composition. In this instance, as a crosslinking composition of the disclosure contacts a cell composition, the controlled degradation of the crosslinking composition results in the release of the lysis composition into the chamber.

The crosslinking composition may be optimized for a controlled release of the lysis composition, either alone, or in combination with, a signaling agent. For example, coating compositions of the disclosure may comprise a signaling agent that activates, inhibits, or alters a signaling pathway of the cell in the chamber. Lysis compositions of the disclosure may comprise a signaling agent that activates, inhibits, or alters a signaling pathway of the cell in the chamber. For example, in a coating composition of the disclosure, a lysis composition may be combined with a first crosslinking composition and a signaling agent may be combined with a second crosslinking composition, wherein the first and second crosslinking compositions are either identical or are uniquely formulated for release of either the lysis composition or the signaling agent at distinct times and/or distinct rates. In certain embodiments of a coating composition of the disclosure, a lysis composition is combined with a first crosslinking composition and a signaling agent is combined with a second crosslinking composition, wherein the first crosslinking composition is added to the substrate as a bottom layer that directly contacts the substrate and the second crosslinking composition is added on top of the first crosslinking composition as a top layer that does not directly contact the substrate. Upon contacting a cell suspension, the top layer (i.e. second crosslinking composition) of the coating composition may degrade or release the signaling agent before the bottom layer (i.e. first crosslinking composition) of the coating composition may degrade or release the lysis composition. The result of this stratified coating composition is a sequential contacting of the cell with the signaling agent followed by a contacting of the cell with the lysis composition. Without requiring moving parts or multiple channels, the compositions of the disclosure can be used to first affect cell signaling and then lyse the cell to expose the intracellular components for immediate analysis.

As an example of the use of a signaling agent of the disclosure, a coating composition of the disclosure may comprise an antigen (as a signaling agent) that stimulates a T cell in the chamber. Upon contact of the cell composition with the coating composition, the crosslinking composition may expand and/or degrade to release the antigen and the lysis composition, either sequentially or simultaneously, to ultimately stimulate and lyse the T cell, exposing the intracellular components and signaling pathways downstream of the antigen receptor that mediate activation of that T cell.

In certain preferred embodiments, the coating composition of the disclosure is optimized for complete single cell lysis within 30 minutes to allow the user sufficient time to image the single cell chambers and lyse the cells fast enough to capture the relevant biology in a repeatable and scalable manner. Compositions of the disclosure comprising a coating composition optimized for controlled release of the lysis composition and complete cell lysis within 30 minutes may further comprise a plurality of capture agents for the detection of, for example, 90 distinct intracellular proteins per single cell and at least 2500 chambers to contain at least 2500 single cells (with a single cell in each chamber).

Consumable Composition

The compositions and methods of the disclosure may be used on a benchtop without computer or robotic control of the multiplexed reaction. The methods of the disclosure comprise introducing a cell composition into the substrate such that a single cell, or a defined number of cells, is introduced into each chamber of the plurality of chambers and allowing the coating composition present in each chamber to release a lysing composition to lyse the cell and expose the intracellular components of each cell to the capture agents on the surface. Once the intracellular components form complexes with the capture agents, the surface may be removed and visualized. Visualization of the intracellular signatures (i.e. the total number of complexes formed between intracellular components and capture agents within a single cell that indicate those intracellular components and pathways involved in any particular cellular process) may be performed using, for example, a fluorescent signal detector. Accordingly, once the cell composition is introduced into the chambers of the substrate, which may be accomplished manually, the methods of the disclosure may be accomplished without additional other "moving parts". While it is possible to remove the surface from the substrate to visualize the complexes of intracellular components bound to capture agents, this step is not required. For example, if the surface is transparent, the capture agents may be visualized through the surface.

The compositions and methods of the disclosure may be used to simultaneously detect hundreds of intracellular components of a single cell while performing this multiplexed analysis on thousands of single cells in parallel. Moreover, visualization of each of the thousands of complex intracellular signatures may be performed simultaneously in a single experiment.

The compositions and methods of the disclosure may be purchased, stored without degradation of the composition, used according to the methods of the disclosure, and discarded. Thus, the compositions of the disclosure are consumable compositions. Furthermore, because the compositions of the disclosure do not require computer control or machine operation for the multiplexed reaction, the compositions of the disclosure may be used without regard to the adaptability of the compositions to any of the user's existing systems. According, the consumable compositions of the disclosure are not only more efficacious than the existing technologies, but also far less expensive to operate.

Compositions

The disclosure provides a composition for the multiplexed detection of a plurality of compounds from single cells comprising an array comprising a plurality of chambers and a plurality of capture agents. Preferred capture agents include antibodies, however, capture agents may include any detectable entity that specifically binds to an intracellular component of the disclosure. The detectable entity may comprise a detectable label, for example. Detectable labels may include, but are not limited to fluorescent labels.

Compositions of the disclosure comprise a plurality of individual chambers, preferably in uniform arrangement. In certain embodiments, at least some of the plurality of individual chambers have a length of greater than 50 µm and, optionally, may be configured to contain an isolated single cell in a sub-nanoliter volume of contents.

Surfaces of the compositions of the disclosure may comprise a plurality of immobilized capture agents, each immobilized capture agent capable of specifically binding to one of the plurality of target intracellular components of the disclosure. Preferably, the immobilized capture agents are attached to the surface in a repeatable pattern, wherein each repeat of the pattern aligns with a chamber of the plurality of chambers.

The substrates and surfaces of the compositions of the disclosure are coupled to form a plurality of enclosed interfaces, each enclosed interface comprising a chamber and at least one repeat of a repeating pattern of a plurality of capture agents such that the contents of each chamber are accessible to each and every capture agent of the at least one repeat of the patterned plurality of capture agents.

Chambers of the substrate may take on any shape and may have any dimension, however, in certain embodiments of the disclosure, the substrate comprises at least 1, 2, 5, 10, 15, 20, 25, 50, 100, 150, 500, 1000, 1500, 2000 or any integer between of chambers. Each chamber may have a depth/height of between 1 µm and 2000 µm, a diameter of between 1 µm and 2000 µm, a width of between 1 µm and 2000 µm and/or a length of between 1 µm and 2000 µm. The distance between any two chambers of the substrate may be between 1 µm and 2000 µm.

In certain embodiments, at least one chamber is a high aspect ratio rectangular well, having dimensions of about 1-2 mm in length and about 5-50 µm in depth.

In certain embodiments, each chamber is rectangular with a length of about 10-2000 µm, a width of about 10-100 µm, and a depth of about 10-100 µm.

In certain embodiments, the plurality of capture agents may comprise between 3 and 500 distinct capture agents, thereby allowing for the detection of between 3 and 500 distinct intracellular components of a single cell. In certain embodiments, the plurality of capture agents may comprise 3 distinct capture agents, thereby allowing for the detection of 3 distinct intracellular components of a single cell. In certain embodiments, the plurality of capture agents may comprise 10 distinct capture agents, thereby allowing for the detection of between 10 distinct intracellular components of a single cell. In certain embodiments, the plurality of capture agents may comprise 50 distinct capture agents, thereby allowing for the detection of between 50 distinct intracellular components of a single cell. In certain embodiments, the plurality of capture agents may comprise 100 distinct capture agents, thereby allowing for the detection of 100 distinct intracellular components of a single cell. In certain embodiments, the plurality of capture agents may comprise 150 distinct capture agents, thereby allowing for the detection of 150 distinct intracellular components of a single cell. In certain embodiments, the plurality of capture agents may comprise 200 distinct capture agents, thereby allowing for the detection of 200 distinct intracellular components of a single cell. In certain embodiments, the plurality of capture agents may comprise 250 distinct capture agents, thereby allowing for the detection of 250 distinct intracellular components of a single cell. In certain embodiments, the plurality of capture agents may comprise 300 distinct capture agents, thereby allowing for the detection of 300 distinct intracellular components of a single cell. In certain embodiments, the plurality of capture agents may comprise 350 distinct capture agents, thereby allowing for the detection of 350 distinct intracellular components of a single cell. In certain embodiments, the plurality of capture agents may comprise 400 distinct capture agents, thereby allowing for the detection of 400 distinct intracellular components of a single cell. In certain embodiments, the plurality of capture agents may comprise 450 distinct capture agents, thereby allowing for the detection of 450 distinct intracellular components of a single cell. In certain embodiments, the plurality of capture agents may comprise 500 distinct capture agents, thereby allowing for the detection of 500 distinct intracellular components of a single cell.

In certain embodiments, the substrate comprises a density of about 200 chambers per cm$^2$ to about 20,000 chambers per cm$^2$.

Multi-Omic Analysis and Discovery Platform

The disclosure provides a quantitative, multi-omic assay capable of capturing intracellular signaling proteins, intracellular cytokine proteins (from, for example, single cancer and immune cells), in conjunction with mRNA transcripts, components of the transcriptome and components of the whole genome, from single cancer cells using a "Simultaneous Protein and Sequencing Capture" device (or composition).

In some embodiments of the simultaneous protein and sequencing capture composition of the disclosure, a single cell and single bead are isolated within an approximately 2 nanoliter volume microchamber that contains an antibody array for the capture and detection of a panel of proteins. The simultaneous protein and sequencing capture composition design permits lysis of each individual trapped cell. Exemplary simultaneous protein and sequencing capture composition of the disclosure can profile a significant panel (up to 90 different phosphoproteins) with approximately 2500 single cells per chip for a statistically representative analysis of a sample cell population. Beads can be cleaved and removed from the chip for further processing. Alternatively, beads can be maintained on-chip for further processing.

The simultaneous protein and sequencing capture composition of the disclosure provide a novel multi-omic platform that enables the simultaneous detection of intracellular phosphoproteins and components the transcriptome for a single cell, with many single cell analyses proceeding in parallel. The multi-omic platform of the disclosure provides a means for users to discover novel correlations and methods of signal flux in a population of cells (including, for example, cancer cells) that is not discoverable otherwise with either of these methods individually (e.g. either of an analysis of intracellular phosphoproteins or an analysis of components of the transcriptome, individually).

The compositions and methods of the disclosure, including the simultaneous protein and sequencing capture composition described herein, incorporate controlled drug release technology into the microchambers of the disclosure. In some embodiments, PDMS microchambers are coated with a biocompatible polymer (for example, a poly (vinyl alcohol) or a PVA), which is loaded with a lysis buffer (SDS). In some embodiments, a single cell is captured per microchamber via binding to a cell capture antibody deposited on a functionalized band in each microchamber. In some embodiments, this functionalized band is 10 μm in width, which allows for the capture of only one cell per chamber. In some embodiments, a PDMS microfluidic chip (e.g. a simultaneous protein and sequencing capture composition of the disclosure) facilitates the lysing of cells in a single cell specific manner. The coating on the chip or on or within a microchamber of the chip may be optimized to allow for complete single cell lysis in under 10 minutes. Complete single cell lysis in under 10 minutes allows the user sufficient time to image the single cell microchambers and lyse the cells with sufficient speed to capture the relevant biology in a repeatable and scalable manner.

Each microchamber of the disclosure is designed to capture one sequencing bead per microchamber by, for example, one of the two following methods: i. each microchamber contains a functionalized streptavidin band for the capture of one sequencing bead per microchamber via a biotinylated oligo. Due to the size of the functionalized streptavidin band (10 μM), only one bead is bound per chamber. The biotin moieties can be cleaved if desired so that bead processing can be done off chip. ii. Each chamber possesses a capture antibody deposited on a functionalized band in conjunction with a size exclusion well so that one cell and one bead are captured per well. In some embodiments, the sequencing beads can range in size between 30 and 40 μm, and, accordingly, the size exclusion well on the microchamber has a diameter of 50 μm or of about 50 μm, thereby allowing for only one bead to fit per well.

DEFINITIONS

Unless otherwise defined, scientific and technical terms used in connection with the disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

The following definitions are useful in understanding the present invention:

The term "antibody" (Ab) as used herein includes monoclonal antibodies, polyclonal antibodies, multispecific antibodies (e.g., bispecific antibodies), and antibody fragments, as long as they exhibit the desired biological activity. The term "immunoglobulin" (Ig) is used interchangeably with "antibody" herein.

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

Capture agents of the disclosure may comprise one or more monoclonal antibodies. The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies.

Monoclonal antibodies contemplated herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. Chimeric antibodies of primary interest herein include antibodies having one or more human antigen binding sequences (e.g., CDRs) and containing one or more sequences derived from a non-human antibody, e.g., an FR or C region sequence. In addition, chimeric antibodies of primary interest herein include those comprising a human variable domain antigen binding sequence of one antibody class or subclass and another sequence, e.g., FR or C region sequence, derived from another antibody class or subclass. Chimeric antibodies of interest herein also include those containing variable domain antigen-binding sequences related to those described herein or derived from a different species, such as a non-human primate (e.g., Old World Monkey, Ape, etc). Chimeric antibodies also include primatized and humanized antibodies.

Capture agents of the disclosure may comprise humanized antibodies. A "humanized antibody" is generally considered to be a human antibody that has one or more amino acid residues introduced into it from a source that is non-human. These non-human amino acid residues are often referred to as "import" residues, which are typically taken from an "import" variable domain. Humanization is traditionally performed by substituting import hypervariable region sequences for the corresponding sequences of a human antibody. Accordingly, such "humanized" antibodies are chimeric antibodies wherein substantially less than an intact human variable domain has been substituted by the corresponding sequence from a non-human species.

A "human antibody" is an antibody containing only sequences present in an antibody naturally produced by a human. However, as used herein, human antibodies may comprise residues or modifications not found in a naturally occurring human antibody, including those modifications and variant sequences described herein. These are typically made to further refine or enhance antibody performance.

Capture agents of the disclosure may comprise intact antibodies. An "intact" antibody is one that comprises an antigen-binding site as well as a CL and at least heavy chain constant domains, CH 1, CH 2 and CH 3. The constant domains may be native sequence constant domains (e.g., human native sequence constant domains) or amino acid sequence variant thereof. Preferably, the intact antibody has one or more effector functions.

Capture agents of the disclosure may comprise an antibody fragment. An "antibody fragment" comprises a portion of an intact antibody, preferably the antigen binding or variable region of the intact antibody. Examples of antibody fragments include Fab, Fab', F(ab')2, and Fv fragments; diabodies; linear antibodies; single-chain antibody molecules; and multispecific antibodies formed from antibody fragments.

Capture agents of the disclosure may comprise a functional fragment or an analog of an antibody. The phrase "functional fragment or analog" of an antibody is a compound having qualitative biological activity in common with a full-length antibody. For example, a functional fragment or analog of an anti-IgE antibody is one that can bind to an IgE immunoglobulin in such a manner so as to prevent or substantially reduce the ability of such molecule from having the ability to bind to the high affinity receptor, FcεRI.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH 1). Each Fab fragment is monovalent with respect to antigen binding, i.e., it has a single antigen-binding site. Pepsin treatment of an antibody yields a single large F(ab')2 fragment that roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments that have hinge cysteines between them. Other chemical couplings of antibody fragments are also known.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

Capture agents of the disclosure may comprise single-chain antibodies (also referred to as scFv). "Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

Capture agents of the disclosure may comprise diabodies. The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

Capture agents of the disclosure may comprise bispecific antibodies. In certain embodiments, antibodies of the present invention are bispecific or multi-specific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen.

Methods for making bispecific antibodies are known in the art. Traditional production of full length bispecific antibodies is based on the co-expression of two immunoglobulin heavy chain-light chain pairs, where the two chains have different specificities. Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low.

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

As used herein, an antibody is said to be "immunospecific," "specific for" or to "specifically bind" an antigen if it reacts at a detectable level with the antigen, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$. Affinity of an antibody for its cognate antigen is also commonly expressed as a dissociation constant KD, and in certain embodiments, an antibody specifically binds to an intracellular component of the disclosure if it binds with a KD of less than or equal to $10^{-4}$ $M^{-1}$, less than or equal to about $10^{-5}$ M, less than or equal to about $10^6$ M, less than or equal to $10^{-7}$ M, or less than or equal to $10^{-8}$ M. Affinities of antibodies can be readily determined using conventional techniques, for example, those described by Scatchard et al. (Ann. N.Y. Acad. Sci. USA 51:660 (1949)).

Cells of the disclosure may be isolated, derived, or prepared from any species, including any mammal. A "mammal" for purposes of treating n infection, refers to any mammal, including humans, domestic and farm animals, and zoo, sports, or pet animals, such as dogs, cats, cattle, horses, sheep, pigs, goats, rabbits, etc. Preferably, the mammal is human.

Cells of the disclosure may be used in a cellular therapy for the treatment of a disease or disorder. "Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal may be successfully "treated" when, after receiving a cellular therapy with a subject cell of the disclosure, the patient shows observable and/or measurable reduction in or absence of one or more of the following: reduction in one or more of the symptoms associated with disease or disorder; reduced morbidity and mortality, and improvement in quality of life issues. The above parameters for assessing successful treatment and improvement in the disease are readily measurable by routine procedures familiar to a physician. Methods of the disclosure may be used to determine the safety and/or efficacy of a cellular therapy before, during or after initiation of treatment of the subject.

Capture agents of the disclosure may be labeled to render them detectable using one or more means. "Label" as used herein refers to a detectable compound or composition that is conjugated directly or indirectly to the capture agent (e.g. an antibody) so as to generate a "labeled" capture agent (e.g. an antibody). The label may be detectable by itself (e.g., a fluorescent label) or, in the case of an enzymatic label, may catalyze chemical alteration of a substrate compound or composition that is detectable.

Capture agents of the disclosure may selectively or specifically identify, capture, and/or quantify intracellular components wherein the intracellular component comprises one or more small molecules. A "small molecule" is defined herein to have a molecular weight below about 500 Daltons.

Capture agents of the disclosure include small molecules.

Capture agents of the disclosure may selectively or specifically identify, capture, and/or quantify intracellular components wherein the intracellular component comprises a DNA molecule, an RNA molecule, or any combination thereof.

Capture agents of the disclosure may include nucleic acids or labeled nucleic acids. The terms "nucleic acid" and "polynucleotide" are used interchangeably herein to refer to single- or double-stranded RNA, DNA, or mixed polymers. Polynucleotides may include genomic sequences, extragenomic and plasmid sequences, and smaller engineered gene segments that express, or may be adapted to express polypeptides.

An "isolated nucleic acid" is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man.

The term "polypeptide" is used in its conventional meaning, i.e., as a sequence of amino acids. The polypeptides are not limited to a specific length of the product. Peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof.

An "isolated polypeptide" is one that has been identified and separated and/or recovered from a component of its natural environment. In preferred embodiments, the isolated polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

A "native sequence" polynucleotide is one that has the same nucleotide sequence as a polynucleotide derived from nature. A "native sequence" polypeptide is one that has the same amino acid sequence as a polypeptide (e.g., antibody) derived from nature (e.g., from any species). Such native sequence polynucleotides and polypeptides can be isolated from nature or can be produced by recombinant or synthetic means.

A polynucleotide "variant," as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences of the invention and evaluating one or more biological activities of the encoded polypeptide as described herein and/or using any of a number of techniques well known in the art.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating one or more biological activities of the polypeptide as described herein and/or using any of a number of techniques well known in the art.

Modifications may be made in the structure of the polynucleotides and polypeptides of the disclosure and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence.

For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences that encode said peptides without appreciable loss of their biological utility or activity.

In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. The substitution of like amino acids can be made effectively on the basis of hydrophilicity. The greatest local average hydrophilicity of a protein, as governed by the hydrophilicity of its adjacent amino acids, correlates with a biological property of the protein.

The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D. C. Vol. 5, Suppl. 3, pp. 345-358; Hein J. (1990) Unified Approach to Alignment and Phylogenes pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information.

"Homology" refers to the percentage of residues in the polynucleotide or polypeptide sequence variant that are identical to the non-variant sequence after aligning the sequences and introducing gaps, if necessary, to achieve the maximum percent homology. In particular embodiments, polynucleotide and polypeptide variants have at least 70%, at least 75%, at least 80%, at least 90%, at least 95%, at least 98%, or at least 99% polynucleotide or polypeptide homology with a polynucleotide or polypeptide described herein.

As used in this specification and the appended claims, the singular forms "a," "an" and "the" include plural references unless the content clearly dictates otherwise.

EXAMPLES

Example 1: Methods of Making Compositions of the Disclosure

A mold for an exemplary 12,000+ chamber PDMS substrate of the disclosure is silicon master etched with the deep-reactive-ion etching (DRIE) method. It was pretreated with trimethylchlorosilane (Sigma-Aldrich) vapor in a vacuum desiccator for 30 minutes to facilitate PDMS release. The wafer was then compressed in an acrylic mold, to form to the shape of the PDMS substrate. The PDMS pre-polymer elastomer base and curing agent, Sylgard 184 (Dow Corning) was mixed completely (parts A and B in a 10:1 ratio) with 0.1% (v/m) Triton X-100 (Sigma-Aldrich and placed in a vacuum desiccator for 30 minutes to remove air bubbles. A surfactant (Triton X-100) was added to the PDMS to minimize long term hydrophobic recovery of the PDMS. The PDMS was injected into the mold using a syringe and the mold was cured in the oven at 80° C. for 1.5 hrs. Resultant chips after PDMS removal from the mold were 25 mm (width)×55 mm (length), and is 4.75 mm in height.

Lysis Composition:

A 3% (v/v) polyvinyl alcohol (PVA) (Mw 146,000-186,000, 99+% Hydrolyzed. Sigma-Aldrich) solution was made in deionized water by constantly mixing at 80° C. for approximately 3 hours. The 3% (v/v) PVA solution was allowed to cool once solution became completely transparent. The 3% (v/v) solution was centrifuged at 300×g for 10 minutes to remove any particulates. Before starting the coating process, 0.2% (v/v) Triton X-100 was added to the PVA solution and mixed with stir bar for 30 minutes at 200 rpm.

Linker Composition:

PDMS chambers were initially cleaned by sonicating for 15 minutes in methanol. Microchambers were dried with compressed air and treated with oxygen plasma (30 s, 40W, 4 cc/min with an AutoGlow 200 produced by Glow Research). Microchambers were then coated with 2% APTES in acetone for 10 minutes at room temperature. Microchambers were rigorously washed with acetone then baked at 80° C. for 30 minutes. The surface amino groups were subsequently reacted with the cross-linker glutaraldehyde (1% in dH2O, 0.1% NaOH, pH 9.2) with a 10 min incubation at room temperature. Microchambers were sonicated (approximately 10 seconds) to removal all air pockets. Samples were rinsed chambers with deionized water, and chamber surface was dried completely with compressed air (60 sec).

Coating Composition:

A PVA coating solution was prepared by adding 0.1% glutaraldehyde and 10% hydrochloric acid to the prepared Triton X-100/PVA solution. Solution was mixed at 100 rpm for 30 seconds and slowly pipetted onto the microchambers to avoid bubbles. Microchambers were then spin coated with coating solution at 2000 rpm for 4 minutes. Samples were then baked for 1 hour at 80 C and vacuum sealed with desiccant to remove residual moisture. Microchambers were removed from vacuum as required for intracellular protein capture.

Cell Loading and Chamber Preparation:

Chambers were removed from vacuum and blocked with 3% BSA for 30 minutes. Target cells were stained with CellTrace Violet stain and loaded onto coated microchambers and enclosed with a surface comprising a repeating pattern of the plurality of capture agents. Cells were incubated for 2 hours. The surface comprising a repeating pattern of the plurality of capture agents was removed for visualization.

Example 2: Multi-Omic Platforms and Methods of Use

Protocol A: Intracellular Dual Band Single Cell/Single Bead Capture Protocol

Fabrication of Microchamber Array Chips:

The mold for the 12,000+ microchamber array PDMS is a silicon master etched with the deep-reactive-ion etching (DRIE) method. It was pretreated with trimethylchlorosilane (Sigma-Aldrich) vapor in a vacuum desiccator for 30 minutes to facilitate PDMS release. The wafer was then compressed in an acrylic mold, to form to the shape of the PDMS chip. The PDMS pre-polymer elastomer base and curing agent, Sylgard 184 (Dow Corning) was mixed completely (parts A and B in a 10:1 ratio) and placed in a vacuum desiccator for 30 minutes to remove air bubbles. The PDMS was injected into the mold using a syringe and the mold was cured in the oven at 80° C. for 1.5 hrs. Resultant chips after PDMS removal from the mold were 25 mm (width)×55 mm (length), and is 4.75 mm in height.

Hydrogel Coating:

the PDMS chip is treated with oxygen plasma, soaked in a 10% (w/v) benzophenone solution in water for 1 minute, rinsed with methanol, and dried with compressed air. PDMS microchambers are covered in 9% PVA-SbQ solution in water, and spin coated for 4 minutes at 2000 rpm to form an even layer. The chip is then covered with a photomask and exposed to deep UV light for 1 hour.

Antibody Deposition:

The PDMS microchamber surface is functionalized by incubation in 1% (3-Aminopropyl)triethoxysilane (APTES) in water for 30 minutes. The PDMS microchambers are then rinsed with water and dried using compressed air followed by incubation in 1% glutaraldehyde in water for 10 minutes. The PDMS microchambers are then rinsed with water and dried using compressed air followed by incubation in 1 mg/ml Protein G in PBS for 30 minutes. The PDMS microchambers are then rinsed with PBS and dried using compressed air followed by incubation in cell capture antibody for 30 minutes. The PDMS microchambers are then rinsed with PBS and dried using compressed air.

Streptavidin Deposition:

Acrylamide-streptavidin solution (1 mg/ml) in PBS is spin coated onto PDMS for 4 minutes at 2000 rpm. This coating is then crosslinked onto PVA-SbQ in a region-specific manner through a photomask after exposed to deep UV light for 1 hour.

Bead Preparation and Loading:

Beads were washed 2× with PBS and then resuspended in PBS at the appropriate concentration. Bead solution was then pipetted onto microchambers and beads were incubated for 30 minutes to allow for binding. After incubation, the microchamber PDMS is rinsed with PBS to remove unbound beads.

Lysis Buffer Loading to Hydrogel:

To load lysis buffer into the hydrogel, coated microchambers are soaked in 3% SDS for 1 hour. The microchamber PDMS is then rinsed with water and dried with compressed air.

Cell Preparation and Loading:

Target cells were stained with CellTrace Violet stain and resuspended in RNAse inhibitor solution (50% PBS, 3% Ficoll PM-400, 10 mM EDTA, 100 mM Tris pH 7.5, 25 mM DTT) at the appropriate concentration before being loaded onto coated microchambers. Cells are allowed to bind and are then rinsed with RNase inhibitor solution to remove unbound cells.

Post-Assay Bead Removal:

After the incubation period is complete, the antibody slide is removed from the microchamber PDMS. The slide and PDMS are both rinsed 10× with PBS+0.1% Triton X-100, which is collected in a 50 mL falcon tube. The microchamber PDMS is then placed in the same falcon tube and QCed to 50 mL with PBS-T. This tube is rotated at room temperature for 10 minutes, then centrifuged at 1000×g for 5 minutes to pellet the beads. After centrifugation, excess PBS-T is aspirated off and the microchamber PDMS is rinsed with 10 mL of PBS-T into the same falcon tube, and then discarded. The falcon tube is spun again at 1000×g for 10 minutes to pellet the beads. After centrifugation, excess PBS-T is aspirated off, leaving about 5 mL. The pellet is resuspended in this same 5 mL and run through a 100 μM filter. Beads are then pelleted at 1000×g for 2 minutes and resuspended in 1 mL of 6×SSC. At this point beads can be processed for cDNA synthesis and NGS.

Protocol B: Intracellular UV-Crosslinkable PVA Single Cell Capture with Size Exclusion Single Bead Capture Fabrication of Microchamber Array Chips:

The mold for the 12,000+ microchamber array PDMS is a silicon master etched with the deep-reactive-ion etching (DRIE) method. It was pretreated with trimethylchlorosilane (Sigma-Aldrich) vapor in a vacuum desiccator for 30 minutes to facilitate PDMS release. The wafer was then compressed in an acrylic mold, to form to the shape of the PDMS chip. The PDMS pre-polymer elastomer base and curing agent, Sylgard 184 (Dow Corning) was mixed completely (parts A and B in a 10:1 ratio) and placed in a vacuum desiccator for 30 minutes to remove air bubbles. The PDMS was injected into the mold using a syringe and the mold was cured in the oven at 80° C. for 1.5 hrs. Resultant chips after PDMS removal from the mold were 25 mm (width)×55 mm (length), and is 4.75 mm in height.

Hydrogel Coating:

the PDMS chip is treated with oxygen plasma, soaked in a 10% (w/v) benzophenone solution in water for 1 minute, rinsed with methanol, and dried with compressed air. PDMS microchambers are covered in 9% PVA-SbQ solution in water, and spin coated for 4 minutes at 2000 rpm to form an even layer. The chip is then covered with a photomask and exposed to deep UV light for 1 hour.

Antibody Deposition:

The PDMS microchamber surface is functionalized by incubation in 1% (3-Aminopropyl)triethoxysilane (APTES) in water for 30 minutes. The PDMS microchambers are then rinsed with water and dried using compressed air followed by incubation in 1% glutaraldehyde in water for 10 minutes. The PDMS microchambers are then rinsed with water and dried using compressed air followed by incubation in 1 mg/ml Protein G in PBS for 30 minutes. The PDMS microchambers are then rinsed with PBS and dried using compressed air followed by incubation in cell capture antibody for 30 minutes. The PDMS microchambers are then rinsed with PBS and dried using compressed air.

Bead Preparation and Loading:

Beads are washed 2× with PBS and then resuspended in PBS at the appropriate concentration. Bead solution is then pipetted onto microchambers and single beads fall into size exclusion wells. After incubation, the microchamber PDMS is rinsed with PBS to remove residual beads.

Lysis Buffer Loading to Hydrogel:

To load lysis buffer into the hydrogel, coated microchambers are soaked in 3% SDS for 1 hour. The microchamber PDMS is then rinsed with dH2O and dried with compressed air.

Cell Preparation and Loading:

Target cells were stained with CellTrace Violet stain and resuspended in RNAse inhibitor solution (50% PBS, 3% Ficoll PM-400, 10 mM EDTA, 100 mM Tris pH 7.5, 25 mM DTT) at the appropriate concentration before being loaded onto coated microchambers. Cells are allowed to bind and are then rinsed with RNase inhibitor solution to remove unbound cells.

Post-Assay Bead Removal:

After the incubation period is complete, the antibody slide is removed from the microchamber PDMS. The slide and PDMS are both rinsed 10× with PBS+0.1% Triton X-100, which is collected in a 50 mL falcon tube. The microchamber PDMS is then placed in the same falcon tube and QCed to 50 mL with PBS-T. This tube is rotated at room temperature for 10 minutes, then centrifuged at 1000×g for 5 minutes to pellet the beads. After centrifugation, excess PBS-T is aspirated off and the microchamber PDMS is rinsed with 10 mL of PBS-T into the same falcon tube, and then discarded. The falcon tube is spun again at 1000×g for 10 minutes to pellet the beads. After centrifugation, excess PBS-T is aspirated off, leaving about 5 mL. The pellet is resuspended in this same 5 mL and run through a 100 uM filter. Beads are then pelleted at 1000×g for 2 minutes and resuspended in 1 mL of 6×SSC. At this point beads can be processed for cDNA synthesis and NGS.

Protocol C: Secretion Proteomics PLL-g-PEG-Biotin Single Cell Capture

Fabrication of Microchamber Array Chips:

The mold for the 12,000+ microchamber array PDMS is a silicon master etched with the deep-reactive-ion etching (DRIE) method. It was pretreated with trimethylchlorosilane (Sigma-Aldrich) vapor in a vacuum desiccator for 30 minutes to facilitate PDMS release. The wafer was then compressed in an acrylic mold, to form to the shape of the PDMS chip. The PDMS pre-polymer elastomer base and curing agent, Sylgard 184 (Dow Corning) was mixed completely (parts A and B in a 10:1 ratio) and placed in a vacuum desiccator for 30 minutes to remove air bubbles. The PDMS was injected into the mold using a syringe and the mold was cured in the oven at 80° C. for 1.5 hrs. Resultant chips after PDMS removal from the mold were 25 mm (width)×55 mm (length), and is 4.75 mm in height.

PLL-g-PEG-Biotin Passivation:

PDMS is washed with 70% Ethanol and dried under air flow. PDMS microchamber surface is functionalized by exposure to oxygen plasma. The PDMS is then soaked in a mixture of 11.5 mg/ml N-(3-Dimethylaminopropyl)-N'-ethylcarbodiimide hydrochloride (EDC) and 19.2 mg/ml N-Hydroxysulfosuccinimide sodium salt (Sulfo-NHS) in a 0.05 M MES+0.5 M NaCl buffer for 15 minutes, rinsed with PBS and water, and incubated in a solution of 0.5 mg/ml of PLL(20)-g[3.5]-PEG(2): poly-L-lysine-g-poly(ethyleneglycol)-biotin (PLL-g-PEG-biotin) in 10 mM HEPES buffer for 3 hours or overnight.

UV Photolithography:

the passivated PDMS surface is covered with a photomask with desired micropatterns, and is exposed to deep UV light for 10 minutes.

Antibody Deposition:

The PDMS chip is incubated in 1% Pluronic® F-127 solution for 30 minutes. The PDMS microchambers are then rinsed with water and dried using compressed air followed by incubation in 114 µg/ml Neutravidin solution for 30 min. The PDMS microchambers are then rinsed with water and dried using compressed air followed by incubation in 1 mg/ml Protein G-Biotin for 30 minutes. The PDMS microchambers are then rinsed with water and dried using compressed air followed by incubation in cell capture antibody for 30 minutes. The PDMS microchambers are then rinsed with water and dried using compressed air.

Cell Preparation and Loading:

Target cells were stained with CellTrace Violet stain and resuspended in PBS at the appropriate concentration before being loaded onto coated microchambers. Cells are allowed to bind and are then rinsed with PBS to remove unbound cells.

INCORPORATION BY REFERENCE

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

OTHER EMBODIMENTS

While particular embodiments of the disclosure have been illustrated and described, various other changes and modifications can be made without departing from the spirit and scope of the disclosure. The scope of the appended claims includes all such changes and modifications that are within the scope of this disclosure.

What is claimed is:

1. A multiplex analysis method for multiplexed analysis of one or more intracellular targets of a single cell, comprising
    contacting a single cell of a biological sample with a surface comprising a plurality of capture agents operatively-linked thereto, wherein:
        each capture agent is configured to specifically bind to a distinct intracellular target,
        the plurality of capture agents form a repeating pattern,
        contacting is performed under conditions sufficient to lyse the single cell to produce a single cell lysate within each chamber of a plurality of chambers of a substrate,
        the substrate is configured to releasably couple with the surface, such that, each chamber of the plurality of chambers is aligned with at least one repeat of the repeating pattern of the plurality of capture agents of the surface; and
        each single cell lysate within each chamber is in fluid communication with the surface;
    incubating the single cell lysate within each chamber for a sufficient time to allow at least one capture agent of the plurality of capture agents to specifically bind to at least one intracellular target to produce a capture agent:target complex; and
    visualizing at least one capture agent:target complex to identify one or more intracellular targets of a single cell in a multiplexed analysis.

2. The method of claim 1, further comprising:
    contacting the at least one capture agent:target complex with a labeled secondary antibody that binds the capture agent and detecting the labeled secondary antibody;
    or
    contacting a first capture agent:target complex with a first labeled secondary antibody that binds the first capture agent,
    contacting a second capture agent:target complex with a second labeled secondary antibody that binds the second capture agent, and
    detecting the first labeled secondary antibody and the second labeled secondary antibody, wherein the first labeled secondary antibody and the second labeled secondary antibody each comprise a distinct label.

3. The method of claim 2, wherein the labeled secondary antibody comprises a fluorescent, gold or silver label.

4. The method of claim 2, further comprises quantifying the at least one intracellular target.

5. The method of claim 4, wherein the quantifying step comprises measuring an intensity and/or a density of the labeled secondary antibody.

6. The method of claim 4, wherein the intracellular target is a phosphoprotein.

7. The method of claim 1, wherein:
    within each chamber of the plurality of chambers the biological sample is in fluid communication with a bead,
    the bead comprises a plurality of capture agents to specifically bind to at least one intracellular target to produce a capture agent:target complex;
    at least one chamber of the plurality of chambers further comprises a functionalized band, and
    at least one of the following is performed:
        sequencing a target of the at least one capture agent:target complex to identify one or more intracellular targets of a single cell in a multiplexed analysis, or
        visualizing at least one capture agent:target complex to identify one or more intracellular targets of a single cell in a multiplexed analysis.

8. The method of claim 7, wherein the bead composition comprises a bead and nucleic acid sequence encoding a barcode, wherein the barcode comprises a sequence encoding a barcode and a sequence encoding a barcode handle and wherein the method comprises sequencing the barcode by synthesizing a cDNA barcode sequence.

9. The method of claim 8, wherein synthesizing the cDNA barcode sequence comprises contacting the sequence encoding the barcode handle, a primer comprising a sequence complementary to a portion of the sequence encoding the barcode handle and a polymerase, under conditions sufficient for hybridization and cDNA synthesis, wherein the contacting produces a cDNA barcode sequence.

10. The method of claim 8, wherein the sequencing step is performed in the chamber.

11. The method of claim 9, wherein the nucleic acid sequence encoding the barcode further comprises one or more of a sequence encoding a PCR handle, a sequence encoding a unique molecular identifier (UMI), a sequence encoding a template switching oligonucleotide (TSO) handle, and a sequence encoding a TSO hybridization site.

12. The method of claim 9, wherein nucleic acid sequence encoding the barcode further comprises, from 5' to 3', a sequence encoding a PCR handle, a sequence encoding a barcode, a sequence encoding a barcode handle, a sequence encoding a unique molecular identifier (UMI), a sequence encoding a template switching oligonucleotide (TSO) handle, and a sequence encoding a TSO hybridization site.

13. The method of claim 8, wherein:
   each bead of a bead composition comprises a unique barcode,
   each bead of each chamber comprises a unique barcode, or
   each bead of the plurality of chambers comprises a unique bar code.

14. The method of claim 8, wherein the sequence encoding the barcode comprises or consists of 12 nucleotides.

15. The method of claim 8, further comprising contacting the nucleic acid sequence encoding the barcode of the bead and a TSO under conditions sufficient for hybridization of the TSO to a portion of the nucleic acid encoding the barcode to produce a nucleic acid/TSO duplex.

\* \* \* \* \*